(12) United States Patent
Van Nest et al.

(10) Patent No.: US 7,183,111 B2
(45) Date of Patent: Feb. 27, 2007

(54) IMMUNOMODULATORY FORMULATIONS AND METHODS FOR USE THEREOF

(75) Inventors: Gary Van Nest, Martinez, CA (US);
Stephen Tuck, Oakland, CA (US);
Karen L. Fearon, Lafayette, CA (US);
Dino Dina, Oakland, CA (US)

(73) Assignee: Dynavax Technologies Corporation, Berkeley, CA (US)

( * ) Notice: Subject to any disclaimer, the term of this patent is extended or adjusted under 35 U.S.C. 154(b) by 28 days.

(21) Appl. No.: 09/927,884

(22) Filed: Aug. 10, 2001

(65) Prior Publication Data

US 2003/0059773 A1 Mar. 27, 2003

Related U.S. Application Data

(63) Continuation-in-part of application No. 09/802,376, filed on Mar. 9, 2001.

(60) Provisional application No. 60/188,557, filed on Mar. 10, 2000.

(51) Int. Cl.
*G01N 33/53* (2006.01)
*C07H 21/02* (2006.01)

(52) U.S. Cl. ..................... 435/975; 536/23.1
(58) Field of Classification Search ................ 435/975; 536/23.1
See application file for complete search history.

(56) References Cited

U.S. PATENT DOCUMENTS

| | | | |
|---|---|---|---|
| 4,458,006 A | 7/1984 | Dönges et al. | |
| 4,458,066 A | 7/1984 | Caruthers et al. | |
| 4,650,675 A | 3/1987 | Borel et al. | |
| 4,849,513 A | 7/1989 | Smith et al. | |
| 4,910,300 A | 3/1990 | Urdea et al. | |
| 4,948,882 A | 8/1990 | Ruth | |
| 5,015,733 A | 5/1991 | Smith et al. | |
| 5,093,232 A | 3/1992 | Urdea et al. | |
| 5,118,800 A | 6/1992 | Smith et al. | |
| 5,118,802 A | 6/1992 | Smith et al. | |
| 5,124,246 A | 6/1992 | Urdea et al. | |
| 5,391,723 A | 2/1995 | Priest | |
| 5,453,496 A | 9/1995 | Caruthers et al. | |
| 5,484,596 A | 1/1996 | Hanna, Jr. et al. | |
| 5,629,158 A | * 5/1997 | Uhlen ........................ | 435/6 |
| 5,663,153 A | 9/1997 | Hutcherson et al. | |
| 5,723,335 A | 3/1998 | Hutcherson et al. | |
| 5,770,434 A | * 6/1998 | Huse .................... | 435/252.33 |
| 5,824,812 A | 10/1998 | Nantz et al. | |
| 5,849,719 A | 12/1998 | Carson et al. | |
| 6,086,901 A | 7/2000 | O'Hagan et al. | |
| 6,174,872 B1 | 1/2001 | Carson et al. | |
| 6,194,388 B1 | 2/2001 | Krieg et al. | |
| 6,207,646 B1 | 3/2001 | Krieg et al. | |
| 6,214,806 B1 | 4/2001 | Krieg et al. | |
| 6,239,116 B1 | 5/2001 | Krieg et al. | |
| 6,306,405 B1 | 10/2001 | O'Hagan et al. | |
| 6,352,975 B1 | 3/2002 | Schreiner et al. | |
| 6,355,267 B1 | 3/2002 | Collins | |
| 6,458,370 B1 | 10/2002 | O'Hagan et al. | |
| 6,465,188 B1 | 10/2002 | Gold et al. | |
| 6,534,062 B2 | 3/2003 | Raz et al. | |
| 6,544,518 B1 | 4/2003 | Friede et al. | |
| 6,558,670 B1 | 5/2003 | Friede et al. | |
| 6,559,129 B1 | 5/2003 | Kasid et al. | |
| 6,562,798 B1 | 5/2003 | Schwartz | |
| 6,589,940 B1 | 7/2003 | Raz et al. | |
| 6,610,661 B1 | 8/2003 | Carson et al. | |
| 6,855,492 B2 | 2/2005 | O'Hagan et al. | |
| 6,884,435 B1 | 4/2005 | O'Hagan et al. | |
| 2001/0046967 A1 | 11/2001 | Van Nest | |
| 2002/0055477 A1 | 5/2002 | Nest et al. | |
| 2003/0022852 A1 | 1/2003 | Nest et al. | |
| 2003/0129251 A1 | 7/2003 | Van Nest et al. | |
| 2003/0133988 A1 | 7/2003 | Fearon et al. | |
| 2003/0175731 A1 | 9/2003 | Fearon et al. | |
| 2003/0199466 A1 | 10/2003 | Fearon et al. | |
| 2003/0216340 A1 | 11/2003 | Nest et al. | |
| 2005/0037403 A1 | 2/2005 | Krieg et al. | |

FOREIGN PATENT DOCUMENTS

| | | |
|---|---|---|
| EP | 0 468 520 A2 | 1/1992 |
| EP | 0 468 520 A3 | 1/1992 |
| WO | WO 96/02555 A1 | 2/1996 |
| WO | WO 97/28259 A1 | 8/1997 |
| WO | WO 98/04740 | 2/1998 |
| WO | WO 98/16247 A1 | 4/1998 |
| WO | WO 98/18810 A1 | 5/1998 |

(Continued)

OTHER PUBLICATIONS

Van Uden et al (Journal of Allergy and Clinical Immunology vol. 104, No. 5, pp. 902-910, Nov. 1999).*

(Continued)

*Primary Examiner*—Mark Navarro
(74) *Attorney, Agent, or Firm*—Morrison & Foerster LLP

(57) ABSTRACT

The invention provides new compositions and methods for immunomodulation of individuals. Immunomodulation is accomplished by administration of immunomodulatory polynucleotide/microcarrier (IMP/MC) complexes. The IMP/MC complexes may be covalently or non-covalently bound, and feature a polynucleotide comprising at least one immunostimulatory sequence bound to a nonbiodegradable microcarrier or nanocarrier.

41 Claims, No Drawings

FOREIGN PATENT DOCUMENTS

| WO | WO 98/37919 A1 | 9/1998 |
|---|---|---|
| WO | WO 98/40100 A1 | 9/1998 |
| WO | WO 98/52581 A1 | 11/1998 |
| WO | WO 98/52962 A1 | 11/1998 |
| WO | WO 98/55495 A2 | 12/1998 |
| WO | WO 98/55495 A3 | 12/1998 |
| WO | WO 98/55609 A1 | 12/1998 |
| WO | WO 99/11275 A2 | 3/1999 |
| WO | WO 99/11275 A3 | 3/1999 |
| WO | WO 99/33488 A2 | 7/1999 |
| WO | WO 99/33488 A3 | 7/1999 |
| WO | WO 99/33868 A2 | 7/1999 |
| WO | WO 99/33868 A3 | 7/1999 |
| WO | WO 99/51259 A2 | 10/1999 |
| WO | WO 99/51259 A3 | 10/1999 |
| WO | WO 99/56755 A1 | 11/1999 |
| WO | WO 99/62923 A2 | 12/1999 |
| WO | WO 99/62923 A3 | 12/1999 |
| WO | WO 00/06588 A1 | 2/2000 |
| WO | WO 00/16804 A1 | 3/2000 |
| WO | WO 00/21556 A1 | 4/2000 |
| WO | WO 00/54803 A2 | 9/2000 |
| WO | WO 00/61161 A2 | 10/2000 |
| WO | WO 00/67023 A1 | 11/2000 |
| WO | WO-01/00231 A2 | 1/2001 |
| WO | WO-01/00231 A3 | 1/2001 |
| WO | WO 01/12223 A2 | 2/2001 |
| WO | WO 01/15726 A2 | 3/2001 |
| WO | WO 01/22972 A2 | 4/2001 |
| WO | WO 01/22990 A2 | 4/2001 |
| WO | WO 01/35991 A2 | 5/2001 |
| WO | WO 01/51500 A1 | 7/2001 |
| WO | WO 01/54720 A1 | 8/2001 |
| WO | WO 01/68077 A2 | 9/2001 |
| WO | WO 01/68078 A2 | 9/2001 |
| WO | WO 01/68103 A2 | 9/2001 |
| WO | WO 01/68116 A2 | 9/2001 |
| WO | WO 01/68117 A2 | 9/2001 |
| WO | WO 01/68143 A2 | 9/2001 |
| WO | WO 01/68144 A2 | 9/2001 |
| WO | WO 01/76642 A1 | 10/2001 |
| WO | WO-03/015816 A1 | 2/2003 |

OTHER PUBLICATIONS

Fearon et al (Eur. J. Immunol. vol. 33, pp. 2114-2122, 2003).*
Asanuma, H. et al., (1995) "Cross-protection against influenza virus infection in mice vaccined by combined nasal/subcutaneous administration" *Vaccine* 13:3-5.
Agrawal et al. (1986). "Efficient methods for attaching non-radioactive labels to the 5'ends of synthetic oligodeoxyribonucleotides," *Nucleic Acids Res.* 14:6227-6245.
Ahmeida, E.T.S. Ben, (1993). "Immunopotentiation of local and systemic humoral immune responses by ISCOMs, liposomes and FCA: role in protection against influenze A in mice,"*Vaccine* 11(13):1302-1309.
Atherton et al. (1981). "Synthesis of a 21-residue fragment of human proinsulin by the polyamide solid phase method," *Hoppe-Seylers Z. Physiol. Chem.* 362:833-839.
Ballas et al. (1996). "Induction of NK activity in murine and human cells by CpG motifs in oligodeoxynucleotides and bacterial DNA," *J.Immunol.* 157:1840-1845.
Benoit et al. (1987). "Peptides. Strategies for antibody production and radioimmunoassays," *Neuromethods* 6:43-72.
Bischoff et al. (1987). "Introduction of 5'-terminal functional groups into synthetic oligonucleotides for selective immobilization," *Analytical Biochemistry* 164:336-344.
Blanks et al. (1988). "An oligodeoxynucleotide affinity column for the isolation of sequence specific DNA binding protein," *Nucleic Acids Res.* 16:10283-10299.

Boujrad et al. (1993). "Inhibition of hormone-stimulated steroidogenesis in cultured Leydig tumor cells by a cholesterol-linked phosphorothioate oligodeoxynucleotide antisense to diazepam-binding inhibitor," *Proc. Natl. Acad. Sci. USA* 90:5728-5731.
Branda et al. (1993)."Immune stimulation by an antisense oligomer complementary to the *rev* gene of HIV-1,"*Biochem. Pharmacol.* 45:2037-2043.
Branda et al. (1996). "Amplification of antibody production by phosphorothioate oligodeoxynucleotides," *J. Lab. Clin. Med.* 128:329-338.
Braun et al. (1988). "Immunogenic duplex nucleic acids are nuclease resistant," *J. Immunol.* 141:2084-2089.
Brazolot Millan et al. (1998) "CpG DNA can induce strong Th1 humoral and cell-mediated immune responses against hepatitis B surface antigen in young mice," *Proc. Natl. Acad. Sci. USA* 95:15553-15558.
Breitendeder et al. (1989). "The gene coding for the major birch pollen allergen *Betvl* is highly homologous to a pea disease resistance response gene," *EMBO J.* 8:1935-1938.
Broide et al. (1998). "Immunostimulatory DNA sequences inhibit IL-5, eosinophilic inflammation, and airway hyperresponsiveness in mice," *J. Immunol.* 161:7054-7062.
Broide et al. (1999) "DNA-based immunization for asthma," *Int. Arch. Allergy Immunol.* 118:453-456.
Carson et al. (1997). "Oligonucleotide adjuvants for T helper 1 (Th1)-specific vaccination," *J. Exp. Med.* 186:1621-1622.
Chace et al. (1997). "Bacterial DNA-induced NK cell IFN-γ production is dependent on macrophage secretion of IL-12," *Clin. Immunol. and Immunopathol.* 84:185-193.
Chaturvedi et al. (1996). "Stabilization of triple-stranded oligonucleotide complexes: use of probes containing alternating phosphodiester and stereo-uniform cationic phosphoramidate linkages," *Nucleic Acids Res.* 24:2318-2323.
Chen et al. (1999). "Enhanced protection against a lethal influenza virus challenge by immunization with both hemagglutinin- and neuraminidase-expressing DNAs,"*Vaccine* 17:653-659.
Chu et al. (1997). "CpG oligodeoxynucleotides act as adjuvants that switch on T helper 1 (Th1) immunity," *J. Exp. Med.* 186:1623-1631.
Chua et al. (1988). "Sequence analysis of cDNA coding for a major house dust mite allergen, *Der p* 1 homology with cysteine proteases," *J. Exp. Med.* 167:175-182.
Chua et al. (1990). "Expression of *Dermatophagoides pteronyssinus* allergen, *Der p* II, in *Escherichia coli* and the binding studies with human IgE," *Int. Arch. Allergy Appl. Immunol.* 91:124-129.
Connolly, Bernard A. (1985)."Chemical synthesis of oligonucleotides containing a free sulphydryl group and subsequent attachment of thiol specific probes," *Nucleic Acids Res.* 13:4485-4502.
Connolly, Bernard A. (1987). "The synthesis of oligonucleotides containing a primary amino group at the 5'-terminus," *Nucleic Acids Res.* 15:3131-3139.
Corey et al. (1987). "Generation of a hybrid sequence-specific single-stranded deoxyribonuclease," *Science* 238:1401-1403.
Cowdery et al. (1996). "Bacterial DNA induces NK cells to produce IFN-γ*in vivo*and increases the toxicity of lipopolysaccharides," *J. Immunol.* 156:4570-4575.
de Martino et al. (1999). "Low IgG3 and high IgG4 sublass levels in children with advanced human immunodeficiency virus-type 1 infection and elevated IgE levels," *Ann. Allergy Asthma Immunol.* 83:160-164.
Elkins et al., (1999) "Bacterial DNA comprising CpG motifs stimulates lymphocyte-dependent protection of mice against lethal infection with intracellular bacteria" *J. Immunol.* 162:2291-2298.
Elsayed et al. (1991). "The structural requirements of epitopes with IgE binding capacity demonstrated by three major allergens from fish, egg and tree pollen," *Scand. J. Clin. Lab. Invest.* 51(Suppl. 204):17-31.
Fornadley, John (1998). "Allergy immunotherapy," *Otolaryngol. Clin. North Am.* 31:111-127.
Gao et al., (1995). "Circularization of oligonucleotides by disulfide bridge formation," *Nucleic Acids Res.* 23(11):2025-2029.

Geoghegan et al. (1992). "Site-directed conjugation of nonpeptide groups to peptides and proteins via periodate oxidation of a 2-amino alcohol. Application to modification at N-terminal serine," *Bioconjug. Chem.* 3:138-146.

Godard et al. (1995) "Antisense effects of cholesterol-oligodeoxynucleotide conjugates associated with poly(alkylcyanoacrylate) nanoparticles" *Eur. J. Biochem.* 232:404-410.

Goodchild, John (1990). "Conjugates of oligonucleotides and modified oligonucleotides: A review of their synthesis and properties" *Bioconjug. Chem.* 1(3):165-187.

Govorkova and Smirnov (1997). "Cross-protection of mice immunized with different influenza A (H2) strains and challenged with viruses of the same HA subtype," *Acta Virol.* 41:251-257.

Grabarek et al., "Zero-length crosslinking procedure with the use of active esters" (1990) *Anal. Biochem.* 185:131-135.

Gramzinski et al., "Immune response to a hepatitis B DNA vaccine in aotus monkeys: A comparison of vaccine formulation, route, and method of administration" (1998) *Mol. Med.* 4:109-118.

Granoff, Dan M. (1993). "Effect of immunity to the carrier protein on antibody responses to *Haemophilus influenzae* type b conjugate vaccines," *Vaccine* 11(1):S46-S51.

Haralambidis et al. (1990). "The synthesis of polyamide-oligonucleotide conjugate molecules," *Nucleic Acids Res.* 18:493-499.

Haralambidis et al. (1990). "The preparation of polyamide-oligonucleotide probes containing multiple non-radioactive labels," *Nucleic Acids Res.* 18:501-505.

Horner et al. (1998). "Rapid communication: Immunostimulatory DNA is a potent mucosal adjuvant," *Cell Immunol.* 190:77-82.

Jäger et al. (1988). "Oligonucleotide N-alkylphosphoramidates: Synthesis and binding to polynucleotides," *Biochem.* 27:7237-7246.

Jakob et al. (1998). "Activation of cutaneous dendrific cells by CpG-containing oligodeoxynucleotides: A role for dendritic cells in the augmentation of Th1 responses by immunostimulatory DNA," *J. Immunol.* 161:3042-3049.

Kandimalla, E.R. et al., (2001) "Effect of chemical modifications of cytosine and guanine in a CpG-motif of oligonucleotides: structure-immunostimulatory activity relationships" *Biorg. Med. Chem.* 9:807-813.

Kataoka et al. (1992). "Antitumor activity of synthetic oligonucleotides with sequences from cDNA encoding proteins of *Mycobacterium bovis* BCG," *Jpn. J. Cancer Res.* 83:244-247.

Kikuta, K. et al., (1990) Cross-protection against influenza B type virus infection by intranasal inoculation of the HA vaccines combined with cholera toxin B subunit *Vaccine* 8:595-599.

Kimura et al. (1994). "Binding of oligoguanylate to scavenger receptors is required for oligonucleotides to augment NK cell activity and induce IFN," *J. Biochem.* (Tokyo) 116:991-994.

Kline et al. (1997). "Immune redirection by CpG oligonucleotides conversion of a Th2 response to a Th1 response in a murine model of asthma," *J. Invest. Med.* 45(3):282A.

Klinman et al. (1996). "CpG motifs present in bacterial DNA rapidly induce lymphocytes to secrete interleukin 6, interleukin 12, and interferon γ," *Proc. Natl. Acad. Sci. USA* 93:2879-2883.

Klinman et al., (1997). "Contribution of CpG motifs to the immunogenicity of DNA vaccines," *J. Immunol.* 158:3635-3639.

Kodihalli et al., (1997). "Cross-protection among lethal H5N2 influenza viruses induced by DNA vaccine to the hemagglutinin,"*J. Virol.* 71(5):3391-3396.

Kovarik et al. (1999). "CpG oligodeoxynucleotides can circumvent the Th2 polarization of neonatal responses to vaccines but may fail to fully redirect Th2 responses established by neonatal priming," *J. Immunol.* 162:1611-1617.

Kremsky et al. (1987). "Immobilization of DNA via oligonucleotides containing an aldehyde or carboxylic acid group at the 5' terminus,"*Nucleic Acids Res.* 15:2891-2909.

Krieg, Arthur M. (1996). "Lymphocyte activation by CpG dinucleotide motifs in prokaryotic DNA," *Trends in Microbiology* 4:73-77.

Krieg, Arthur M. (1998). "Leukocyte stimulation by oligodeoxynucleotides" Chapter 24 in *Applied Antisense Oligonucleotide Technology*. C.A. Stein et al. eds. Wiley-Liss, Inc.: pp. 431-448.

Krieg et al. (1989). "A role for endogenous retroviral sequences in the regulation of lymphocyte activation," *J. Immunol.* 143:2448-2451.

Kreig et al. (1995). "CpG motifs in bacterial DNA trigger direct B-cell activation" *Nature* 374:546-549.

Krieg et al. (1996). "Oligodeoxynucleotide modifications determine the magnitude of B cell stimulation by CpG motifs,"*Antisense & Nucleic Acid Drug Dev.* 6:133-139.

Krieg et al., (1998). "The role of CpG dinucleotides in DNA vaccines" *Trends Microbiol.* 6:23-27.

Krieg et al., "CpG DNA induces sustained IL-12 expression in vivo and resistance to *Listeria monocytogenes* challenge" (1998) *J. Immunol.* 161:2428-2434.

Krieg et al., "Sequence motifs in adenoviral DNA block immune activation by stimulatory CpG motifs" (1998) *Proc. Natl. Acad. Sci. USA* 95:12631-12636.

Krieg et al., (1999) "CpG DNA: a novel immunomodulator" *Trends Microbiol.* 7(2):64-65.

Latimer et al., "Specificity of monoclonal antibodies produced against phosphorothioate and ribo modified DNAs" (1995) *Mol. Immunol.* 32:1057-1064.

Lea et al., "Cloning and sequencing of cDNAs encoding the human sperm protein, Sp17" (1996) *Biochim. Biophys. Acta* 1307-263-266.

Leclerc et al., (1997) "The preferential induction of a TH1 immune response by DNA-based immunization is mediated by the immunostimulatory effect of plasmid DNA" *Cell. Immunol.* 179:97-106.

Liang, Hua et al. (1996). "Activation of human B cells by phosphoroghioate oligodeoxynucleotides," *J. Clin. Invest.* 98(5):1119-1129.

Lipford et al., "Immunostimulatory DNA: sequence-dependent production of potentially harmfull or useful cytokines" (1997) *Eur. J. Immunol.* 27:3420-3426.

Lipford et al, "CpG-containing synthetic oligonucleotides promote B and cytotoxic T cell responses to protein antigen: a new class of vaccine adjuvants" (1997) *Eur. J. Immunol.* 27:2340-2344.

Liu et al., "Immunostimulatory CpG oligodeoxynucleotides enhance the immune response to vaccine strategies involving granulocyte-macrophage colony-stimulating factor" (1998) *Blood* 92:3730-3736.

Macfarlane et al., "Unmethylated CpG-containing oligodeoxynucleotides inhibit apoptosis in WEHI 231 B lymphocytes induced by several agents: evidence for blockade of apoptosis at a distal signalling step" (1997) *Immunology* 91:586-593.

Malley, Arthur, "The immune response of offspring mice from mothers immunized during pregnancy with protein antigens" (1989) *J. Reprod. Immunol.* 16:173-186.

Manzel et al., (1999) "Lack of immune stimulation by immobilized CpG-oligodeoxynucleotide" *Antisense Nucl. Acid Drug Dev.* 9:459-464.

Martin-Orozco et al., "Enhancement of antigen-presenting cell surface molecules involved in cognate interactions by immunostimulatory DNA sequences" (1999) *Intnl Immunol.* 11(7):1111-1118.

Mbawuike et al., "Influenza: A subtype cross-protection after immunization of outbred mice with a purified chimeric $NS_1/HA_2$ influenza virus protein" (1994) *Vaccine* 12(14):1340-1348.

McCluskie et al., "Cutting edge: CpG DNA is a potent enhancer of systemic and mucosal immune responses against hepatitis B surface antigen with intranasal administration to mice" (1998) *J. Immunol.* 161(9):4463-4466.

Miller et al., "Syntheses and properties of adenine and thymine nucleoside alkyl phosphotriesters, the neutral analogs of dinucleoside monophosophates" (1971) *JACS* 93:6657-6665.

Mitragotri et al., "Ultrasound-mediated transdermal protein delivery" (1995) *Science* 269:850-853.

Mojcik et al., "Administration of a phosphorothioate oligonucleotide antisense to murine endogenous retroviral MCF env causes immune effects *in vivo* in a sequence-specific manner" (1993) *Clin. Immuno. and Immunopathol.* 67:130-136.

Moldoveanu et al., "CpG DNA, a novel immune enhancer for systemic and mucosal immunization with influenza virus" (1998) *Vaccine* 16:1216-1224.

Nelson et al. (1989) "A new and versatile reagent for incorporating multiple primary aliphatic amines into synthetic oligonucleotides" *Nucleic Acids Res.* 17(18):7179-7186.

Nelson et al., "N3'→P5' oligodeoxyribonucleotide phosphoramidates: A new method of synthesis based on a phosphoramidite amino-exchange reaction," (1997) *J. Org. Chem.* 62:7278-7287.

O'Shannessy et al., "Specific conjugation reactions of the oligosaccharide moieties of immunoglobulins" (1985) *J. Applied Biochem.* 7:347-355.

Pertmer et al., "Influenza virus nucleoprotein-specific immunoglobulin G subclass and cytokine responses elicited by DNA vaccination are dependent on the route of vector DNA delivery" (1996) *J. Virol.* 70:6119-6125.

Peyrottes et al., "Oligodeoxynucleoside phosphoramidates ($P-NH_2$): synthesis and thermal stability of duplexes with DNA and RNA targets" (1996) *Nucleic Acids Res.* 24:1841-1848.

Pisetsky, David S., "The immunologic properties of DNA" (1996a) *J. Immunol.* 156:421-423.

Pisetsky, David S., "Immune activation by bacterial DNA: A new genetic code" (1996b) *Immunity* 5:303-310.

Pisetsky et al., "Stimulation of murine lymphocyte proliferation by a phosphorothioate oligonucleotide with antisense activity for herpes simplex virus" (1994) *Life Sci.* 54:101-107.

Pisetsky et al., "Immunological properties of bacterial DNA DNA vaccines: A new era in vaccinology" (1995) *Ann. N. Y. Acad. Sci.*, 772:152-163.

Rafnar et al., "Cloning of *Amb a I* (antigen E), the major allergen family of short ragweed pollen" (1991) *J. Biol. Chem.* 266:1229-1236.

Raz et al., "Intradermal gene immunization: The possible role of DNA uptake in the induction of cellular immunity to viruses" (1994) *Proc. Natl. Acad. Sci. USA* 91:9519-9523.

Raz et al., "Preferential induction of a $Th_1$ immune response and inhibition of specific IgE antibody formation by plasmid DNA immunization" (1996) *Proc. Natl. Acad. Sci. USA* 93:5141-5145.

Redford et al., "Cyclosporin A enhances IL-12 production by CpG motifs in bacterial DNA and synthetic oligodeoxynucleotides" (1998) *J. Immunol.* 161:3930-3935.

Rogers et al., "Recombinant *Fel d* I: Expression, purification, IgE binding and reaction with cat-allergic human T cells" (1993) *Mol. Immunol.* 30:559-568.

Roget et al., "Synthesis and use of labelled nucleoside phosphoramidite building blocks bearing a reporter group: biotinyl, dinitrophenyl, pyrenyl and dansyl" (1989) *Nucleic Acids Res.* 17:7643-7651.

Romagnani, S. (2000) T-cell subsets (Th1 versus Th2)*Ann. Allergy Asthma Immunol.* 85:9-18.

Roman et al., "Immunostimulatory DNA sequences function as T helper-1-promoting adjuvants" (1997) *Nature Medicine* 3:849-854.

Ruth, Jerry L., "Oligodeoxynucleotides with reporter groups attached to the base" (1991) *Oligonucleotides and Analogues: A Practical Approach,* Eckstein, ed., IRL Press, pp. 255-282.

Sato et al., "Immunostimulatory DNA sequences necessary for effective intradermal gene immunization" (1996) *Science* 273:352-354.

Schacht et al., (1996) "Biomedical applications of degradable polyphosphazenes" *Biotechnol. Bioeng.* 52:102-108.

Scherle et al., "Functional analysis of influenza specific helper T cell clones *in vivo*" (1986) *J. Exp. Med.* 164:1114-1128.

Scherle et al. "Differential ability of B cells specific for external vs. internal influenza virus proteins to respond to help from influenza virus-specific T-cell clones *in vivo*" (1988) Proc. Natl. Acad. Sci. USA 85:4446-4450.

Schultz et al., "Oligo-2'- fluoro-2'-deoxynucleotide N3'→P5' phosphoramidates: synthesis and properties" (1996) *Nucleic Acids Res.* 24:2966-2973.

Schwartz et al., "CpG motifs in bacterial DNA cause inflammation in the lower respiratory tract" (1997) *J. Clin. Invest.* 100:68-73.

Shimada et al., "*In vivo* augmentation of natural killer cell activity with a deoxyribonucleic acid fraction of BCG" (1986) *Jpn. J. Cancer Res.* 77:808-816.

Sinha et al., "Oligonucleotides with reporter groups attached to the 5'-terminus" (1991) *Oligonucleotide Analogues: A Practical Approach,* Eckstein, ed., IRL Press, pp. 185-210.

Sonehara et al., "Hexamer palindromic oligonucleotides with 5'-CG-3' motif(s) induce production of interferon" (1996) *J. Interferon and Cytokine Res.* 16:799-803.

Sparwasser et al., "Macrophages sense pathogens via DNA motifs: induction of tumor necrosis factor-α-mediated shock" (1997) *Eur. J. Immunol.* 27:1671-1679.

Spiegelberg et al., "Inhibition of IgE formation and allergic inflammation by allergen gene immunization and by CpG motif immunostimulatory oligodeoxynucleotides" (1998) *Allergy* 53:93-97.

Spiegelberg et al., "Inhibition of allergic inflammation in the lung by plasmid DNA allergen immunization" (1999) *Pediatric Pulmonology* Suppl. 18:118-121.

Stacey et al., "Macrophages ingest and are activated by bacterial DNA" (1996) *J. Immunol.* 157:2116-2122.

Staros et al., "Enhancement by *N*-hydroxysulfosuccinimide of water-soluble carbodiimide-mediated coupling reactions" (1986) *Anal. Biochem.* 156:220-222.

Stein et al., "Chapter 11: Non-antisense effects of oligodeoxynucleotides" (1997) *Antisense Technology,* C. Lichtenstein and W. Nellen, eds., IRL Press, pp. 241-264.

Stirchak et al., "Uncharged stereoregular nucleic acid analogs: 2. Morpholino nucleoside oligomers with carbamate internucleoside linkages" (1989) *Nucleic Acids Res.* 17:6129-6141.

Tamura et al., "Superior cross-protective effect of nasal vaccination to subcutaneous inoculation with influenza hemagglutinin vaccine" (1992) *Eur. J. Immunol.* 22:477-481.

Tamura et al., "Formulation of inactivated influenza vaccines for providing effective cross-protection by intranasal vaccination in mice" (1994) *Vaccine* 12:310-316.

Tokunaga et al., "Synthetic oligonucleotides with particular base sequences from the cDNA encoding proteins of *Mycobacterium bovis* BCG induce interferons and activate natural killer cells" (1992) *Microbiol. Immunol.* 36:55-66.

Tung et al., "Preparation of oligonucleotide-peptide conjugates" (1991) *Bioconjug. Chem.* 2:464-465.

Verthelvi, D. et al., (Feb. 15, 2001) "Human peripheral blood cells differentially recognize and respond to two distinct CpG motifs" *J. Immunol.*166(4):2372-2377.

Wang et al., "Circular RNA oligonucleotides. Synthesis, nucleic acid binding properties, and a comparison with circular DNAs" (1994) *Nucleic Acids Res.* 22:2326-2333.

Warner et al., "Laboratory methods. Construction and evaluation of an instrument for the automated synthesis of oligodeoxyribonucleotides" (1984) *DNA* 3:401-411.

Weeratna et al. (1998) "Brief Communication: Reduction of antigen expression from DNA vaccinnes by coadministered oligodeoxynucleotides" *Antisense & Nucleic Acid Drug Development* 8:351-356.

Weiner et al., "Immunostimulatory oligodeoxynucleotides containing the CpG motif are effective as immune adjuvants in tumor antigen immunization"(1997) *Proc. Natl. Acad. Sci. USA* 94:10833-10837.

Widhe, M. et al. (1998). "IgG subclasses in lyme borreliosis: A study of specific IgG subclass distribution in an interferon-γ-predominated disease," *Scand. J. Immunol.* 47:575-581.

Wooldridge et al., "Immunostimulatory oligodeoxynucleotides containing CpG motifs enhance the efficacy of monoclonal antibody therapy of lymphoma" (1997) *Blood* 89:2994-2998.

Yamamoto et al., "Unique palindromic sequences in synthetic oligonucleotides are required to induce INF and augment INF-mediated natural killer activity" (1992) *J. Immunol.* 148:4072-4076.

Yamamoto et al. (1994) "Ability of oligonucleotides with certain palindromes to induce interferon production and augment natural killer cell activity is associated with their base length" *Antisense Research and Development* 4:119-122.

Yamamoto et al., "Synthetic oligonucleotides with certain palindromes stimulate interferon production of human peripheral blood lymphocytes in vitro" (1994) *Jpn. J. Cancer Res.* 85:775-779.

Yanagawa et al., "Analysis of superhelical structures of nucleic acid-lipid conjugates by image processing" (1988) *Nucleic Acids Symp. Series* 19:189-192.

Yi et al. (1996) "IFN-γ promotes IL-6 and IgM secretion in response to CpG motifs in bacterial DNA and oligonucleotides" *J. Immunol.* 156:558-564.

Yi et al., "CpG DNA rescue from anti-IgM-induced WEHI-231 B lymphoma apoptosis via modulation of IκBα and IκBβ and sustained activation of nuclear factor-κB/c-Rel" (1998) *J. Immunol.* 160:1240-1245.

Yi et al., "CpG motifs in bacterial DNA activate leukocytes through the pH-dependent generation of reactive oxygen species" (1998) *J. Immunol.* 160:4755-4761.

Yi et al., "CpG oligodeoxynucleotides rescue mature spleen B cells from spontaneous apoptosis and promote cell cycle entry" (1998) *J. Immunol.* 160:5898-5906.

Yi et al., "Cutting edge: Rapid induction of mitogen-activated protein kinases by immune stimulatory CpG DNA" (1998) *J. Immunol.* 161:4493-4497.

Zhao et al., "Effect of different chemically modified oligodeoxynucleotides on immune stimulation" (1996) *Biochem. Pharmacol.* 51:173-182.

Zon, Gerald, "Oligonucleoside phosphorothioates" Protocols for Oligonucleotides and Analogs, Chapter 8 in *Methods in Molecular Biology*, vol. 20 (1993) pp. 165-189.

Zimmerman et al., "Cutting edge: CpG oligodeoxynucleotides trigger protective and curative Th1 responses in lethal murine leishmaniasis" (1998) J. Immunol. 3627-3630.

Zuckermann et al., "Efficient methods for attachment of thiol specific probes to the 3'-ends of synthetic oligodeoxyribonucleotides" (1987) *Nucleic Acids Res.* 15:5305-5321.

Bhatt et al., Nucleosides & Nucleotides (1999) 18(6&7):1297-1299.

Fritz et al., Journal of Colloid and Interface Science (1997) 195:272-288.

Lewis et al., Journal of Drug Targeting (1998) 5(4):291-302.

Schwab et al., Proc. Natl. Acad. Sci. USA (1994) 91:10460-10464.

Agrawal, S. et al. (2000). *Molecular Med. Today* 6:72-81.

Busquets et al. (2003). *Current Drug Targets* 4:633-642.

Crooke, S. (1998). Chapters 1 and 2 in *Antisense Research and Application*, S. Crooke, ed., Springer-Verlag, pp. 1-50.

Fix et al. (2002). *FEBS Letters* 516:109-112.

Li et al. (1993). *Biochimica et Biophysica Acta* 1166:145-153.

Peracchi, A. et al. (2004). *Rev. Med. Virol.* 14:47-64.

Stayton, P.S. et al. (2000). *J. Controlled Release* 65:203-220.

Aderem, A. et al. (Dec. 22, 2000). "How do you see CG?," *Cell* 103:993-996.

Gursel, I. et al. (2001). "Sterically Stabilized Cationic Liposomes Improve the Uptake and Immunostimulatory Activity of CpG Oligonucleotides," *Immunology* 167:3324-3328.

International Search Report mailed on Feb. 11, 2002 for PCT Application No. PCT/US01/07848 filed Mar. 12, 2001, three pages.

International Search Report mailed on Aug. 27, 2002 for PCT Application No. PCT/US01/25364 filed Aug. 12, 2001, four pages.

International Search Report mailed on Feb. 11, 2002 for PCT Application No. PCT/US01/07843 filed Mar. 12, 2001, three pages.

Kato, D. et al. (2003). "The Design of Polymer Microcarrier Surfaces for Enhanced Cell Growth," *Biomaterials* 24:4253-4264.

Kazzaz, J. et al. (2000). "Novel Anionic Microparticles are a Potent Adjuvant for the Induction of Cytotoxic T Lymphocytes Against Recombinant p55 gag From HIV-1," *J. Controlled Release* 67:347-356.

Klinman, D.M. et al. (2004). "Use CpG Oligodeoxynucleotides as Immune Adjuvants," *Immunological Reviews* 199:201-216.

Kofler, N. et al. (1996). "Preparation and Characterization of Poly-(D,L-lactide-co-glycolide) and Poly-(L-lactic acid) Microspheres with Entrapped Pneumotropic Barterial Antigens.," *J. Immunological Methods* 192:25-35.

Krieg, A.M. (2002). "CpG motifs in Bacterial DNA and Their Immune Effects," *Annual Review Immunology* 20:709-760.

Lefeber, D.J. et al. (Dec. 2003), "Th1-directing Ajuvants Increase the Immunogenicity of Oligosaccharide-protein Conjugate Vaccines Related to *Streptococcus pneumonise* Type 3," *Infection and Immunity* 71(12):6915-6920.

Maloy, K.J. et al. (1994). "Induction of Mucosal and Systemic Immune Responses by Immunization with Ovalbumin Entrapped in Poly(lactide-co-glycolide) Microparticles," *Immunology* 81:661-667.

Nellore, R.V. et al. (Sep.-Oct. 1992). "Evaluation of Biodegradable Microspheres as Vaccine Adjuvant for Hepatitis B Surface Antigen," *J. Parenteral Science and Technology* 46(5):176-180.

O'Hagan, D.T. et al. (2000). "Microparticles in MF59, a Potent Adjuvant Combination for a Recombinant Protein Vaccine Against HIV-1," *Vaccine* 18:1793-1801.

O'Hagan, D.T. et al. (2000). "Recent Developments in Adjuvants for Vaccines Against Infectious Diseases," *Biomolecular Engineering* 18:69-85.

O'Hagan, D.T. et al. (2000). "Synergistic Adjuvant Activity of Immunostimulatory DNA and Oil/water Emulsions for Immunization with HIV p55 gag Antigen," *Vaccine* 20:3389-3398.

Plenat, F. (Jun. 1996). "Animal Models of Antisense Oligonucleotides: Lessons for use in Humans," *Molecular Medicine Today* 2(6):250-257.

Ponchel, G. et al. (1998). "Specific and Non-specific Bioadhesive Particulate Systems for Oral Delivery to the Gastrointestinal Tract," *Advanced Drug Delivery Reviews* 34:191-219.

Ryan, E.J. et al. (Aug. 2001). "Immunomodulators and Delivery Systems for Vaccination by Mucosal Routes," *Trends in Biotechnology* 19(8):293-304.

Singh, M. et al. (Nov. 1999). "Advances in Vaccines Adjuvants," *Nature Biotechnology* 17:1075-1081.

Singh, M. et al. (Jan. 18, 2000). "Cationic Microparticles: A Potent Delivery System for DNA Vaccines," *PNAS* 97(2):811-816.

Uhlmann, E. et al. (2003). "Recent Advances in the Development of Immunostimulatory Oligonucleotides," *Current Opinion in Drug Discovery and Development* 6(2):204-217.

Weeratna, R.D. et al. (2000). "CpG DNA Induces Stronger Immune Responses with less Toxicity than Other Adjuvants," *Vaccine* 18:1755-1762.

Du Bois, R.M. (Oct. 21, 1999). "Interferon Gamma-1b for the Treatment of Idiopathic Pulmonary Fibrosis," *New England Journal of Medicine* 341(17):1302-1304.

\* cited by examiner

IMMUNOMODULATORY FORMULATIONS AND METHODS FOR USE THEREOF

CROSS-REFERENCE TO RELATED APPLICATIONS

This application is a continuation-in-part of copending U.S. application Ser. No. 09/802,376, filed Mar. 9, 2001, which in turn claims the priority benefit of U.S. Provisional application 60/188,557, filed Mar. 10, 2000, each of which is hereby incorporated herein by reference in its entirety.

TECHNICAL FIELD

The present invention relates to immunomodulatory compositions comprising an immunostimulatory oligonucleotide sequence (ISS). In particular, the invention relates to immunomodulatory compositions comprising an ISS bound to a nonbiodegradable microparticle. It also relates to the administration of the polynucleotide/microcarrier complex to modulate at least one immune response.

BACKGROUND ART

The type of immune response generated to infection or other antigenic challenge can generally be distinguished by the subset of T helper (Th) cells involved in the response. The Th1 subset is responsible for classical cell-mediated functions such as delayed-type hypersensitivity and activation of cytotoxic T lymphocytes (CTLs), whereas the Th2 subset functions more effectively as a helper for B-cell activation. The type of immune response to an antigen is generally influenced by the cytokines produced by the cells responding to the antigen. Differences in the cytokines secreted by Th1 and Th2 cells are believed to reflect different biological functions of these two subsets. See, for example, Romagnani (2000) *Ann. Allergy Asthma Immunol.* 85:9–18.

The Th1 subset may be particularly suited to respond to viral infections, intracellular pathogens, and tumor cells because it secretes IL-2 and IFN-γ, which activate CTLs. The Th2 subset may be more suited to respond to free-living bacteria and helminthic parasites and may mediate allergic reactions, since IL-4 and IL-5 are and helminthic parasites and may mediate allergic reactions, since IL-4 and IL-5 are known to induce IgE production and eosinophil activation, respectively. In general, Th1 and Th2 cells secrete distinct patterns of cytokines and so one type of response can moderate the activity of the other type of response. A shift in the Th1/Th2 balance can result in an allergic response, for example, or, alternatively, in an increased CTL response.

For many infectious diseases, such as tuberculosis and malaria, Th2-type responses are of little protective value against infection. Proposed vaccines using small peptides derived from the target antigen and other currently used antigenic agents that avoid use of potentially infective intact viral particles, do not always elicit the immune response necessary to achieve a therapeutic effect. The lack of a therapeutically effective human immunodeficiency virus (HIV) vaccine is an unfortunate example of this failure. Protein-based vaccines typically induce Th2-type immune responses, characterized by high titers of neutralizing antibodies but without significant cell-mediated immunity.

Moreover, some types of antibody responses are inappropriate in certain indications, most notably in allergy where an IgE antibody response can result in anaphylactic shock. Generally, allergic responses also involve Th2-type immune responses. Allergic responses, including those of allergic asthma, are characterized by an early phase response, which occurs within seconds to minutes of allergen exposure and is characterized by cellular degranulation, and a late phase response, which occurs 4 to 24 hours later and is characterized by infiltration of eosinophils into the site of allergen exposure. Specifically, during the early phase of the allergic response, allergen cross-links IgE antibodies on basophils and mast cells, which in turn triggers degranulation and the subsequent release of histamine and other mediators of inflammation from mast cells and basophils. During the late phase response, eosinophils infiltrate into the site of allergen exposure (where tissue damage and dysfunction result).

Antigen immunotherapy for allergic disorders involves the subcutaneous injection of small, but gradually increasing amounts, of antigen. Such immunization treatments present the risk of inducing IgE-mediated anaphylaxis and do not efficiently address the cytokine-mediated events of the allergic late phase response. Thus far, this approach has yielded only limited success.

Administration of certain DNA sequences, generally known as immunostimulatory sequences or "ISS," induces an immune response with a Th1-type bias as indicated by secretion of Th1-associated cytokines. Administration of an immunostimulatory polynucleotide with an antigen results in a Th1-type immune response to the administered antigen. Roman et al. (1997) *Nature Med.* 3:849–854. For example, mice injected intradermally with *Escherichia coli* (*E. coli*) β-galactosidase (β-Gal) in saline or in the adjuvant alum responded by producing specific IgG1 and IgE antibodies, and CD4$^+$ cells that secreted IL-4 and IL-5, but not IFN-γ, demonstrating that the T cells were predominantly of the Th2 subset. However, mice injected intradermally (or with a tyne skin scratch applicator) with plasmid DNA (in saline) encoding β-Gal and containing an ISS responded by producing IgG2a antibodies and CD4$^+$ cells that secreted IFN-γ, but not IL-4 and IL-5, demonstrating that the T cells were predominantly of the Th1 subset. Moreover, specific IgE production by the plasmid DNA-injected mice was reduced 66–75%. Raz et al. (1996) *Proc. Natl. Acad. Sci. USA* 93:5141–5145. In general, the response to naked DNA immunization is characterized by production of IL-2, TNFα and IFN-γ by antigen-stimulated CD4$^+$ T cells, which is indicative of a Th1-type response. This is particularly important in treatment of allergy and asthma as shown by the decreased IgE production. The ability of immunostimulatory polynucleotides to stimulate a Th1-type immune response has been demonstrated with bacterial antigens, viral antigens and with allergens (see, for example, WO 98/55495).

ISS-containing oligonucleotides bound to microparticles (SEPHAROSE® beads) have previously been shown to have immunostimulatory activity in vitro (Liang et al., (1996), *J. Clin. Invest.* 98:1119–1129). However, recent results show that ISS-containing oligonucleotides bound to gold, latex and magnetic particles are not active in stimulating proliferation of 7TD1 cells, which proliferate in response to ISS-containing oligonucleotides (Manzel et al. (1999) *Antisense Nucl. Acid Drug Dev.* 9:459–464).

Other references describing ISS include: Krieg et al. (1989) *J. Immunol.* 143:2448–2451; Tokunaga et al. (1992) *Microbiol. Immunol.* 36:55–66; Kataoka et al. (1992) *Jpn. J. Cancer Res.* 83:244–247; Yamamoto et al. (1992) *J. Immunol.* 148:4072–4076; Mojcik et al. (1993) *Clin. Immuno. and Immunopathol.* 67:130–136; Branda et al. (1993) *Biochem. Pharmacol.* 45:2037–2043; Pisetsky et al. (1994) *Life Sci.* 54(2):101–107; Yamamoto et al. (1994a) *Antisense Research and Development.* 4:119–122; Yamamoto et al. (1994b) *Jpn. J. Cancer Res.* 85:775–779; Raz et al. (1994)

Proc. Natl. Acad. Sci. USA 91:9519–9523; Kimura et al. (1994) J. Biochem. (Tokyo) 116:991–994; Krieg et al. (1995) Nature 374:546–549; Pisetsky et al. (1995) Ann. N.Y. Acad. Sci. 772:152–163; Pisetsky (1996a) J. Immunol. 156:421–423; Pisetsky (1996b) Immunity 5:303–310; Zhao et al. (1996) Biochem. Pharmacol. 51:173–182; Yi et al. (1996) J. Immunol. 156:558–564; Krieg (1996) Trends Microbiol. 4(2):73–76; Krieg et al. (1996) Antisense Nucleic Acid Drug Dev. 6:133–139; Klinman et al. (1996) Proc. Natl. Acad. Sci. USA. 93:2879–2883; Raz et al. (1996); Sato et al. (1996) Science 273:352–354; Stacey et al. (1996) J. Immunol. 157:2116–2122; Ballas et al. (1996) J. Immunol. 157:1840–1845; Branda et al. (1996) J. Lab. Clin. Med. 128:329–338; Sonehara et al. (1996) J. Interferon and Cytokine Res. 16:799–803; Klinman et al. (1997) J. Immunol. 158:3635–3639; Sparwasser et al. (1997) Eur. J. Immunol. 27:1671–1679; Roman et al. (1997); Carson et al. (1997) J. Exp. Med. 186:1621–1622; Chace et al. (1997) Clin. Immunol. and Immunopathol. 84:185–193; Chu et al. (1997) J. Exp. Med. 186:1623–1631; Lipford et al. (1997a) Eur. J. Immunol. 27:2340–2344; Lipford et al. (1997b) Eur. J. Immunol. 27:3420–3426; Weiner et al. (1997) Proc. Natl. Acad. Sci. USA 94:10833–10837; Macfarlane et al. (1997) Immunology 91:586–593; Schwartz et al. (1997) J. Clin. Invest. 100:68–73; Stein et al. (1997) Antisense Technology, Ch. 11 pp. 241–264, C. Lichtenstein and W. Nellen, Eds., IRL Press; Wooldridge et al. (1997) Blood 89:2994–2998; Leclerc et al. (1997) Cell. Immunol. 179:97–106; Kline et al. (1997) J. Invest. Med. 45(3):282A; Yi et al. (1998a) J. Immunol. 160:1240–1245; Yi et al. (1998b) J. Immunol. 160:4755–4761; Yi et al. (1998c) J. Immunol. 160:5898–5906; Yi et al. (1998d) J. Immunol. 161:4493–4497; Krieg (1998) Applied Antisense Oligonucleotide Technology Ch. 24, pp. 431–448, C. A. Stein and A. M. Krieg, Eds., Wiley-Liss, Inc.; Krieg et al. (1998a) Trends Microbiol. 6:23–27; Krieg et al. (1998b) J. Immuno. 161:2428–2434; Krieg et al. (1998c) Proc. Natl. Acad. Sci. USA 95:12631–12636; Spiegelberg et al. (1998) Allergy 53(45S):93–97; Homer et al. (1998) Cell Immunol. 190: 77–82; Jakob et al. (1998) J. Immunol. 161:3042–3049; Redford et al. (1998) J. Immunol. 161:3930–3935; Weeratna et al. (1998) Antisense & Nucleic Acid Drug Development 8:351–356; McCluskie et al. (1998) J. Immunol. 161(9): 4463–4466; Gramzinski et al. (1998) Mol. Med. 4:109–118; Liu et al. (1998) Blood 92:3730–3736; Moldoveanu et al. (1998) Vaccine 16: 1216–1224; Brazolot Milan et al. (1998) Proc. Natl. Acad. Sci. USA 95:15553–15558; Briode et al. (1998) J. Immunol. 161:7054–7062; Briode et al. (1999) Int. Arch. Allergy Immunol. 118:453–456; Kovarik et al. (1999) J. Immunol. 162:1611–1617; Spiegelberg et al. (1999) Pediatr. Pulmonol. Suppl. 18:118–121; Martin-Orozco et al. (1999) Int. Immunol. 11:1111–1118; EP 468,520; WO 96/02555; WO 97/28259; WO 98/16247; WO 98/18810; WO 98/37919; WO 98/40100; WO 98/52581; WO 98/55495; WO 98/55609 and WO 99/11275. See also Elkins et al. (1999) J. Immunol. 162:2291–2298, WO 98/52962, WO 99/33488, WO 99/33868, WO 99/51259 and WO 99/62923. See also Zimmermann et al. (1998) J. Immunol. 160:3627–3630; Krieg (1999) Trends Microbiol. 7:64–65; U.S. Pat. Nos. 5,663,153, 5,723,335, 5,849,719 and 6,174, 872. See also WO 99/56755, WO 00/06588, WO 00/16804; WO 00/21556; WO 00/67023 and WO 01/12223. See also Verthelyi et al. (2001) J. Immunol. 166:2372–2377; WO 00/54803; WO 00/61161; WO 00/54803; WO 01/15726; WO 01/22972; WO 01/22990; WO 01/35991; WO 01/51500; WO 01/54720; U.S. Pat. Nos. 6,194,388, 6,207, 646, 6,214,806, 6,239,116.

Additionally, Godard et al. (1995) Eur. J. Biochem. 232: 404–410, discloses cholesterol-modified antisense oligonucleotides bound to poly(isohexylcyanoacrylate) nanoparticles.

All patents, patent applications, and publications cited herein are hereby incorporated by reference in their entirety.

DISCLOSURE OF THE INVENTION

The invention relates to new compositions and methods for modulating immune responses in individuals, particularly human individuals.

In one aspect, the invention relates to compositions which comprise immunomodulatory polynucleotide/microcarrier (IMP/MC) complexes. An IMP/MC complex comprises a polynucleotide comprising an immunostimulatory sequence (IMP) linked to a nonbiodegradable microcarrier (MC) with the proviso that if MC is gold, latex or magnetic, the linkage is other than via biotin/avidin (or biotin/strepavidin). The IMP may be covalently or non-covalently linked to the microcarrier in the complex, and the IMP may be modified to facilitate complex formation. Microcarriers used in IMP/MC complexes maybe liquid phase microcarriers or solid phase microcarriers. Microcarriers are generally less than about 150, 120 or 100 µm in size, and may be about 10 nm to about 10 µm or about 25 nm to 5 µm in size. In certain embodiments, the compositions of the invention comprise an IMP/MC complex and a pharamceutically acceptable excipient. In certain embodiments, the compositions of the invention comprise an antigen-free IMP/MC complex, i.e., an IMP/MC complex not linked to an antigen (either directly or indirectly). In certain embodiments, the IMP/MC complex further comprises an antigen.

In another aspect, the invention relates to methods of modulating an immune response in an individual, comprising administering to an individual an IMP/MC complex in an amount sufficient to modulate an immune response in said individual. Immunomodulation according to the methods of the invention may be practiced on individuals including those suffering from a disorder associated with a Th2-type immune response (e.g., allergies or allergy-induced asthma), individuals receiving vaccines such as therapeutic vaccines (e.g., vaccines comprising an allergy epitope, a mycobacterial epitope, or a tumor associated epitope) or prophylactic vaccines, individuals with cancer, individuals having an infectious disease and individuals at risk of exposure to an infectious agent.

In a further aspect, the invention relates to methods of increasing interferon-gamma (IFN-γ) in an individual, comprising administering an effective amount of an IMP/MC complex to the individual. Administration of an IMP/MC complex in accordance with the invention increases IFN-γ in the individual. Suitable subjects for these methods include those individuals having idiopathic pulmonary fibrosis (IPF), scleroderma, cutaneous radiation-induced fibrosis, hepatic fibrosis including schistosomiasis-induced hepatic fibrosis, renal fibrosis as well as other conditions which may be improved by administration of IFN-γ.

In another aspect, the invention relates to methods of increasing IFN-α in an individual, comprising administering an effective amount of an IMP/MC complex to the individual. Administration of an IMP/MC complex in accordance with the invention increases IFN-α levels in the individual. Suitable subjects for these methods include those individuals having disorders which respond to the administration of IFN-α, including viral infections and cancer.

In another aspect, the invention relates to methods of ameliorating one or more symptoms of an infectious disease, comprising administering an effective amount of an IMP/MC complex to an individual having an infectious disease. Administration of an IMP/MC complex in accordance with the invention ameliorates one or more symptoms of the infectious disease. The infectious diseases which may be treated in accordance with the invention include infectious diseases caused by a cellular pathogen (e.g., a mycobacterial disease, malaria, leishmaniasis, toxoplasmosis, schistosomiasis or clonorchiasis), and may include or exclude viral diseases.

The invention further relates to kits for carrying out the methods of the invention. The kits of the invention comprise a container comprising an IMP/MC complex (or as described herein, materials for production of IMP/MC complexes) and optionally include instructions for use of IMP/MC complex in immunomodulation of an individual, for example when the individual suffers from a disorder associated with a Th2-type immune response (e.g., allergies or allergy-induced asthma), is receiving vaccines such as therapeutic vaccines (e.g., vaccines comprising an allergy epitope, a mycobacterial epitope, or a tumor associated epitope) or prophylactic vaccines, suffers from cancer, suffers from an infectious disease or is at risk of exposure to an infectious agent.

The polynucleotide of the IMP/MC complexes of the invention comprises the sequence 5'-C G-3'. In certain embodiments, the polynucleotide of the IMP/MC complex comprises the sequence 5'-T C G-3'. In certain embodiments, the polynucleotide of the IMP/MC complex comprises the sequence 5'-CG-3' and further comprises the sequence 5'-TCG-3'. In certain embodiments, the polynucleotide of the IMP/MC complex is 7 nucleotides in length.

MODES OF PRACTICING THE INVENTION

We have discovered new compositions and methods for modulating immune responses in individuals, including and particularly humans. The compositions of the invention comprise an immunomodulatory polynucleotide (IMP) complexed with a nonbiodegradable microcarrier (MC). We have found that immunomodulatory polynucleotides combined with nanometer-scale microcarriers (50 and 200 nm diameter beads) efficiently modulate immune cells, including human cells. IMPs combined with small microcarriers (approximately 1 to 4.5 µm, less than 2.0 µm or about 1.5 µm diameter) also immunomodulated human cells. Our discovery is of particular interest because human cells, as is known in the art, can be more resistant to immunomodulation by IMPs than cells from commonly used laboratory animals, such as mice.

The IMP/MC complexes may include or exclude an antigen. In some embodiments, the invention provides compositions comprising antigen-free IMP/MC complexes, i.e., IMP/MC complexes not linked to an antigen (directly or indirectly). In other embodiments, the invention provides compositions comprising IMP/MC complexes mixed with one or more antigens. In other embodiments, the invention provides compositions comprising IMP/MC complexes linked to antigen.

We have further found that covalently linked IMP/MC complexes comprising nonbiodegradable nanocarrier particles are highly active immunomodulators. Prior teaching in the art indicates that immunostimulatory oligonucleotides tightly bound to nonbiodegradable microparticles and nanoparticles are not effective (Manzel et al., supra). In view of this understanding in the art, we believe that our results would be surprising and unexpected to one of skill in the art.

The immunomodulatory polynucleotide/microcarrier (IMP/MC) complexes of the invention may be covalently or non-covalently linked, and comprise a microcarrier (e.g., a carrier of less than about 10 µm size) that is insoluble in water. Microcarriers may be solid phase (e.g., polystyrene beads) or liquid phase (e.g., liposomes, micelles, or oil droplets in an oil and water emulsion). The IMP may be modified to allow or augment binding to the MC (e.g., by incorporation of a free sulfhydryl for covalent crosslinking or addition of a hydrophobic moiety such as cholesterol for hydrophobic bonding).

The invention provides new compositions comprising an IMP covalently linked to a nonbiodegradable microcarrier to form a covalent IMP/MC complex. Linkage between the IMP and MC may be direct (e.g., via disulfide bond between sulfhydryls on the IMP and MC) or the constituents may be linked by a crosslinking moiety of one or more atoms separating the bonds to the IMP and MC.

Also provided are compositions comprising an IMP non-covalently linked to a microcarrier to provide a non-covalent IMP/MC complex. Non-covalent IMP/MC complexes generally comprise an IMP that has been modified to allow binding to the microcarrier (e.g., by addition of a cholesterol moiety to the IMP to allow hydrophobic binding to oil or lipid based microcarrier).

The invention also provides methods for modulating an immune response in an individual by administering an IMP/MC complex to the individual.

Further provided are kits for practicing the methods of the invention. The kits comprise any of the IMP/MC complexes and/or components for the IMP/MC complex in suitable packaging and may also contain instructions for administering an IMP/MC complex for immunomodulation in a subject.

General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, *Molecular Cloning: A Laboratory Manual*, second edition (Sambrook et al., 1989); *Oligonucleotide Synthesis* (M. J. Gait, ed., 1984); *Animal Cell Culture* (R. I. Freshney, ed., 1987); *Handbook of Experimental Immunology* (D. M. Weir & C. C. Blackwell, eds.); *Gene Transfer Vectors for Mammalian Cells* (J. M. Miller & M. P. Calos, eds., 1987); *Current Protocols in Molecular Biology* (F. M. Ausubel et al., eds., 1987); *PCR: The Polymerase Chain Reaction*, (Mullis et al., eds., 1994); *Current Protocols in Immunology* (J. E. Coligan et al., eds., 1991); *The Immunoassay Handbook* (D. Wild, ed., Stockton Press NY, 1994); *Bioconjugate Techniques* (Greg T. Hermanson, ed., Academic Press, 1996); and *Methods of Immunological Analysis* (R. Masseyeff, W. H. Albert, and N. A. Staines, eds., Weinheim: VCH Verlags gesellschaft mbH, 1993).

Definitions

As used herein, the singular form "a", "an", and "the" includes plural references unless indicated otherwise. For example, "an" ISS includes one or more ISS.

As used interchangeably herein, the terms "polynucleotide" and "oligonucleotide" include single-stranded DNA (ssDNA), double-stranded DNA (dsDNA), single-stranded RNA (ssRNA) and double-stranded RNA (dsRNA), modified oligonucleotides and oligonucleosides or combinations thereof. The oligonucleotide can be linearly or circularly configured, or the oligonucleotide can contain both linear and circular segments. Oligonucleotides are polymers of nucleosides joined, generally, through phosphoester linkages, although alternate linkages, such as phosphorothioate esters may also be used in oligonucleotides. A nucleoside consists of a purine (adenine or guanine or inosine or derivative thereof) or pyrimidine (thymine, cytosine or uracil, or derivative thereof) base bonded to a sugar. The four nucleoside units (or bases) in DNA are called deoxyadenosine, deoxyguanosine, deoxythymidine, and deoxycytidine. A nucleotide is a phosphate ester of a nucleoside.

The instant disclosure uses single letters to indicate bases of a nucleotide sequence, where A is adenine, G is guanine, C is cytosine, T is thymine, U is uracil, I is inosine, R is a purine, and Y is a pyrimidine.

The term "ISS" as used herein refers to polynucleotide sequences, alone and/or complexed with MC, that effect a measurable immune response as measured in vitro, in vivo and/or ex vivo. Examples of measurable immune responses include, but are not limited to, antigen-specific antibody production, secretion of cytokines, activation or expansion of lymphocyte populations such as NK cells, CD4+ T lymphocytes, CD8+ T lymphocytes, B lymphocytes, and the like. Preferably, the ISS sequences preferentially activate a Th1-type response. A polynucleotide for use in the invention contains at least one ISS. As used herein, "ISS" is also a shorthand term for an ISS-containing polynucleotide.

The term "immunomodulatory polynucleotide" or "IMP", as used herein, refers to a polynucleotide comprising at least one ISS. In certain embodiments, the IMP is an ISS.

The term "nonbiodegradable", as used herein, refers to a microcarrier which is not degraded or eroded under normal mammalian physiological conditions. Generally, a microcarrier is considered nonbiodegradable if it not degraded (i.e., loses less than 5% of its mass and/or average polymer length) after a 72 hour incubation at 37° C. in normal human serum.

The term "microcarrier" refers to a particulate composition which is insoluble in water and which has a size of less than about 150, 120 or 100 µm, preferably less than about 50–60 µm, preferably less than about 10 µm, preferably less than about 5, 2.5, 2 or 1.5 µm. Microcarriers include "nanocarriers", which are microcarriers have a size of less than about 1 µm, preferably less than about 500 nm. Microcarriers include solid phase particles such a particles formed from biocompatible naturally occurring polymers, synthetic polymers or synthetic copolymers, although microcarriers formed from agarose or cross-linked agarose may be included or excluded from the definition of microcarriers herein. Solid phase microcarriers are formed from polymers or other materials which are non-erodible and/or non-degradable under mammalian physiological conditions, such as polystyrene, polypropylene, silica, ceramic, polyacrylamide, gold, latex, hydroxyapatite, dextran, and ferromagnetic and paramagnetic materials. Microcarriers may also be oil or lipid based, such liposomes, iscoms (immune-stimulating complexes, which are stable complexes of cholesterol, and phospholipid, adjuvant-active saponin) without antigen, or droplets or micelles found in oil-in-water or water-in-oil emulsions. Microcarriers are typically spherical in shape, but microcarriers which deviate from spherical shape are also acceptable (e.g., ellipsoidal, rod-shaped, etc.). Due to their insoluble nature (with respect to water), microcarriers are filterable from water and water-based (aqueous) solutions.

The "size" of a microcarier is generally the "design size" or intended size of the particles stated by the manufacturer. Size may be a directly measured dimension, such as average or maximum diameter, or may be determined by an indirect assay such as a filtration screening assay. Direct measurement of microcarrier size is typically carried out by microscopy, generally light microscopy or scanning electron microscopy (SEM), in comparison with particles of known size or by reference to a micrometer. As minor variations in size arise during the manufacturing process, microcarriers are considered to be of a stated size if measurements show the microcarriers are ± about 5–10% of the stated measurement. Size characteristics may also be determined by dynamic light scattering. Alternately, microcarrier size may be determined by filtration screening assays. A microcarrier is less than a stated size if at least 97% of the particles pass through a "screen-type" filter (i.e., a filter in which retained particles are on the surface of the filter, such as polycarbonate or polyethersulfone filters, as opposed to a "depth filter" in which retained particles lodge within the filter) of the stated size. A microcarrier is larger than a stated size if at least about 97% of the microcarrier particles are retained by a screen-type filter of the stated size. Thus, at least about 97% microcarriers of about 10 µm to about 10 nm in size pass through a 10 µm pore screen filter and are retained by a 10 nm screen filter.

As above discussion indicates, reference to a size or size range for a microcarrier implicitly includes approximate variations and approximations of the stated size and/or size range. This is reflected by use of the term "about" when referring to a size and/or size range, and reference to a size or size range without reference to "about" does not mean that the size and/or size range is exact.

The term "immunomodulatory polynucleotide/microcarrier complex" or "IMP/MC complex" refers to a complex of an ISS-containing polynucleotide comprising a 5'-CG-3' sequence and a microcarrier of the invention. The components of the complex may be covalently or non-covalently linked. Non-covalent linkages may be mediated by any non-covalent bonding force, including by hydrophobic interaction, ionic (electrostatic) bonding, hydrogen bonds and/or van der Waals attractions. In the case of hydrophobic linkages, the linkage is generally via a hydrophobic moiety (e.g., cholesterol) covalently linked to the IMP.

As used herein, "immunomodulatory" can refer to the polynucleotide and/or the complex. Thus, IMP/MC complex may exhibit immunomodulatory activity even when the polynucleotide of the IMP/MC complex has a sequence that, if presented as a polynucleotide alone, does not exhibit comparable immunomodulatory activity. In some embodiments, when presented alone, a polynucleotide of an IMP/MC complex does not have "isolated immunomodulatory activity," or has "inferior isolated immunomodulatory activity," (i.e., when compared to the IMP/MC complex). The "isolated immunomodulatory activity" of a polynucleotide is determined by measuring the immunomodulatory activity of the isolated polynucleotide having the same nucleic acid backbone (e.g., phosphorothioate, phosphodiester, chimeric) using standard assays which indicate at least one aspect of an immune response, such as those described herein.

The term "immunomodulatory" or "modulating an immune response" as used herein includes immunostimulatory as well as immunosuppressive effects. Immunomodulation is primarily a qualitative alteration in an overall immune response, although quantitative changes may also occur in conjunction with immunomodulation. An immune response that is immunomodulated according to the present invention is one that is shifted towards a "Th1-type" immune response, as opposed to a "Th2-type" immune response. Th1-type responses are typically considered cellular immune system (e.g., cytotoxic lymphocytes) responses, while Th2-type responses are generally "humoral", or antibody-based. Th1-type immune responses are normally characterized by "delayed-type hypersensitivity" reactions to an antigen, and can be detected at the biochemical level by increased levels of Th1-associated cytokines such as IFN-γ, IL-2, IL-12, and TNF-β, as well as IFN-α and IL-6, although IL-6 may also be associated with Th2-type responses as well. Th1-type immune responses are generally associated with the production of cytotoxic lymphocytes (CTLs) and low levels or transient production of antibody. Th2-type immune responses are generally associated with higher levels of antibody production, including IgE production, an absence of or minimal CTL production, as well as expression of Th2-associated cytokines such as IL-4. Accordingly, immunomodulation in accordance with the invention may be recognized by, for example, an increase in IFN-γ and/or a decrease in IgE production in an individual treated in accordance with the methods of the invention as compared to the absence of treatment.

The term "conjugate" refers to a complex in which an ISS-containing polynucleotide and an antigen are linked. Such conjugate linkages include covalent and/or non-covalent linkages.

The term "antigen" means a substance that is recognized and bound specifically by an antibody or by a T cell antigen receptor. Antigens can include peptides, proteins, glycoproteins, polysaccharides, complex carbohydrates, sugars, gangliosides, lipids and phospholipids; portions thereof and combinations thereof. The antigens can be those found in nature or can be synthetic. Antigens suitable for administration with ISS include any molecule capable of eliciting a B cell or T cell antigen-specific response. Preferably, antigens elicit an antibody response specific for the antigen. Haptens are included within the scope of "antigen." A hapten is a low molecular weight compound that is not immunogenic by itself but is rendered immunogenic when conjugated with an immunogenic molecule containing antigenic determinants. Small molecules may need to be haptenized in order to be rendered antigenic. Preferably, antigens of the present invention include peptides, lipids (e.g. sterols, fatty acids, and phospholipids), polysaccharides such as those used in Hemophilus influenza vaccines, gangliosides and glycoproteins.

"Adjuvant" refers to a substance which, when added to an immunogenic agent such as antigen, nonspecifically enhances or potentiates an immune response to the agent in the recipient host upon exposure to the mixture.

The term "peptide" are polypeptides that are of sufficient length and composition to effect a biological response, e.g. antibody production or cytokine activity whether or not the peptide is a hapten. Typically, the peptides are at least six amino acid residues in length. The term "peptide" further includes modified amino acids (whether or not naturally or non-naturally occurring), such modifications including, but not limited to, phosphorylation, glycosylation, pegylation, lipidization and methylation.

"Antigenic peptides" can include purified native peptides, synthetic peptides, recombinant proteins, crude peptide extracts, or peptides in a partially purifed or unpurified active state (such as peptides that are a part of attenuated or inactivated viruses, cells, micro-organisms, or fragments of such peptides). An "antigenic peptide" or "antigen polypeptide" accordingly means all or a portion of a polypeptide which exhibits one or more antigenic properties. Thus, for example, an "Amb a 1 antigenic polypeptide" or "Amb a 1 polypeptide antigen" is an amino acid sequence from Amb a 1, whether the entire sequence, a portion of the sequence, and/or a modification of the sequence, which exhibits an antigenic property (i.e., binds specifically to an antibody or a T cell receptor).

A "delivery molecule" or "delivery vehicle" is a chemical moiety which facilitates, permits, and/or enhances delivery of an IMP/MC complex to a particular site and/or with respect to particular timing. A delivery vehicle may or may not additionally stimulate an immune response.

An "allergic response to antigen" means an immune response generally characterized by the generation of eosinophils and/or antigen-specific IgE and their resultant effects. As is well-known in the art, IgE binds to IgE receptors on mast cells and basophils. Upon later exposure to the antigen recognized by the IgE, the antigen cross-links the IgE on the mast cells and basophils causing degranulation of these cells, including, but not limited to, histamine release. It is understood and intended that the terms "allergic response to antigen", "allergy", and "allergic condition" are equally appropriate for application of some of the methods of the invention. Further, it is understood and intended that the methods of the invention include those that are equally appropriate for prevention of an allergic response as well as treating a pre-existing allergic condition.

As used herein, the term "allergen" means an antigen or antigenic portion of a molecule, usually a protein, which elicits an allergic response upon exposure to a subject. Typically the subject is allergic to the allergen as indicated, for instance, by the wheal and flare test or any method known in the art. A molecule is said to be an allergen even if only a small subset of subjects exhibit an allergic (e.g., IgE) immune response upon exposure to the molecule. A number of isolated allergens are known in the art. These include, but are not limited to, those provided in Table 1 herein.

The term "desensitization" refers to the process of the administration of increasing doses of an allergen to which the subject has demonstrated sensitivity. Examples of allergen doses used for desensitization are known in the art, see, for example, Fornadley (1998) *Otolaryngol. Clin. North Am.* 31:111–127.

"Antigen-specific immunotherapy" refers to any form of immunotherapy which involves antigen and generates an antigen-specific modulation of the immune response. In the allergy context, antigen-specific immunotherapy includes, but is not limited to, desensitization therapy.

An "individual" is a vertebrate, preferably a mammal, more preferably a human. Mammals include, but are not limited to, humans, primates, farm animals, sport animals, rodents and pets. Vertebrates also include, but are not limited to, birds (i.e., avian individuals) and reptiles (i.e., reptilian individuals).

An "effective amount" or a "sufficient amount" of a substance is that amount sufficient to effect beneficial or desired results, including clinical results, and, as such, an "effective amount" depends upon the context in which it is being applied. In the context of administering a composition that modulates an immune response to an antigen, an effective amount of an IMP/MC complex is an amount sufficient to achieve such a modulation as compared to the immune response obtained when the antigen is administered alone. An effective amount can be administered in one or more administrations.

The term "co-administration" as used herein refers to the administration of at least two different substances sufficiently close in time to modulate an immune response. Preferably, co-administration refers to simultaneous administration of at least two different substances.

"Stimulation" of an immune response, such as Th1 response, means an increase in the response, which can arise from eliciting and/or enhancement of a response.

An "IgE associated disorder" is a physiological condition which is characterized, in part, by elevated IgE levels, which may or may not be persistent. IgE associated disorders include, but are not limited to, allergy and allergic reactions, allergy-related disorders (described below), asthma, rhinitis, conjunctivitis, urticaria, shock, *Hymenoptera* sting allergies, and drug allergies, and parasite infections. The term also includes related manifestations of these disorders. Generally, IgE in such disorders is antigen-specific.

An "allergy-related disorder" means a disorder resulting from the effects of an antigen-specific IgE immune response. Such effects can include, but are not limited to, hypotension and shock. Anaphylaxis is an example of an allergy-related disorder during which histamine released into the circulation causes vasodilation as well as increased permeability of the capillaries with resultant marked loss of plasma from the circulation. Anaphylaxis can occur systemically, with the associated effects experienced over the entire body, and it can occur locally, with the reaction limited to a specific target tissue or organ.

The term "viral disease", as used herein, refers to a disease which has a virus as its etiologic agent. Examples of viral diseases include hepatitis B, hepatitis C, influenza, acquired immunodeficiency syndrome (AIDS), and herpes zoster.

As used herein, and as well-understood in the art, "treatment" is an approach for obtaining beneficial or desired results, including clinical results. For purposes of this invention, beneficial or desired clinical results include, but are not limited to, alleviation or amelioration of one or more symptoms, diminishment of extent of disease, stabilized (i.e., not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

"Palliating" a disease or disorder means that the extent and/or undesirable clinical manifestations of a disorder or a disease state are lessened and/or time course of the progression is slowed or lengthened, as compared to not treating the disorder. Especially in the allergy context, as is well understood by those skilled in the art, palliation may occur upon modulation of the immune response against an allergen(s). Further, palliation does not necessarily occur by administration of one dose, but often occurs upon administration of a series of doses. Thus, an amount sufficient to palliate a response or disorder may be administered in one or more administrations.

An "antibody titer", or "amount of antibody", which is "elicited" by an IMP/MC complex refers to the amount of a given antibody measured at a time point after administration of IMP/MC complex.

A "Th1-associated antibody" is an antibody whose production and/or increase is associated with a Th1 immune response. For example, IgG2a is a Th1-associated antibody in mouse. For purposes of this invention, measurement of a Th1-associated antibody can be measurement of one or more such antibodies. For example, in human, measurement of a Th1-associated antibody could entail measurement of IgG1 and/or IgG3.

A "Th2-associated antibody" is an antibody whose production and/or increase is associated with a Th2 immune response. For example, IgG1 is a Th2-associated antibody in mouse. For purposes of this invention, measurement of a Th2-associated antibody can be measurement of one or more such antibodies. For example, in human, measurement of a Th2-associated antibody could entail measurement of IgG2 and/or IgG4.

To "suppress" or "inhibit" a function or activity, such as cytokine production, antibody production, or histamine release, is to reduce the function or activity when compared to otherwise same conditions except for a condition or parameter of interest, or alternatively, as compared to another condition. For example, an IMP/MC complex administered with an antigen or including an antigen which suppresses histamine release reduced histamine release as compared to, for example, histamine release induced by antigen alone.

As used herein, the term "comprising" and its cognates are used in their inclusive sense; that is, equivalent to the term "including" and its corresponding cognates.

COMPOSITIONS OF THE INVENTION

The invention provides new compositions for modulating immune response in individuals. The new compositions are immunomodulatory polynucleotide/microcarrier (IMP/MC) complexes which comprise an ISS-containing polynucleotide complexed to a nonbiodegradable micro carrier. IMP/MC complexes may be covalent complexes, in which the IMP portion of the complex is covalently bonded to the MC, either directly or via a linker (i.e., indirectly), or they may be non-covalent complexes.

Immunomodulatory Polynucleotides

In accordance with the present invention, the immunomodulatory polynucleotide comprises the sequence 5'-cytosine, guanine-3', can contain at least one ISS, and can contain multiple ISSs. The ISSs can be adjacent within the polynucleotide, or they can be separated by additional nucleotide bases within the polynucleotide. Accordingly, an IMP may contain combinations of any one or more ISS described herein, including those with modifications. In certain embodiments, the IMP consists of an ISS. The IMP affects a measurable immune response, as measured in vitro, in vivo and/or ex vivo, when complexed with a microcarrier. In some embodiments, the IMP is not active or, in some embodiments, is less active, as measured in vitro, in vivo and/or ex vivo, when uncomplexed.

The ISS can be of any length greater than 6 bases or base pairs and generally comprises the sequence 5'-cytosine, guanine-3', preferably greater than 15 bases or base pairs, more preferably greater than 20 bases or base pairs in length. As is well-known in the art, the cytosine of the 5'-cytosine, guanine-3' sequence is generally unmethylated, especially at the C-5 position. As the term "ISS" conveys and is defined, an ISS effects an immune response and as such, in certain embodiments, methylation of the cytosine may be permitted, for example, at the N-4 position. An ISS may also comprise the sequence 5'-purine, purine, C, G, pyrimidine, pyrimidine, C, G-3'. An ISS may also comprise the sequence 5'-purine, purine, C, G, pyrimidine, pyrimidine, C, C-3'. As indicated in polynucleotide sequences below, an ISS may comprise (i.e., contain one or more of) the sequence 5'-T, C, G-3'. Accordingly, an ISS may comprise 5'-CG-3' and/or 5'-TCG-3'. In some embodiments, an ISS may comprise the sequence 5'-C, G, pyrimidine, pyrimidine, C, G-3' (such as 5'-CGTTCG-3'). In some embodiments, an ISS may comprise the sequence 5'-C, G, pyrimidine, pyrimidine, C, G, purine, purine-3'. In some embodiments, an ISS comprises the sequence 5'-purine, purine, C, G, pyrimidine, pyrimidine-3' (such as 5'-AACGTT-3').

In some embodiments, an ISS may comprise the sequence 5'-purine, T, C, G, pyrmidine, pyrimidine-3'.

In some embodiments, the ISS comprises any of the following sequences:

GACGCTCC; GACGTCCC; GACGTTCC; GACGCCCC; AGCGTTCC; AGCGCTCC; AGCGTCCC; AGCGCCCC; AACGTCCC; AACGCCCC; AACGTTCC; AACGCTCC; GGCGTTCC; GGCGCTCC; GGCGTCCC; GGCGCCCC; GACGCTCG; GACGTCCG; GACGCCCG; GACGTTCG; AGCGCTCG; AGCGTTCG; AGCGTCCG; AGCGCCCG; AACGTCCG; AACGCCCG; AACGTTCG; AACGCTCG; GGCGTTCG; GGCGCTCG; GGCGTCCG; GGCGCCCG.

In some embodiments, the ISS comprises any of the following sequences:

GACGCT; GACGTC; GACGTT; GACGCC; GACGCU; GACGUC; GACGUU; GACGUT; GACGTU; AGCGTT; AGCGCT; AGCGTC; AGCGCC; AGCGUU; AGCGCU; AGCGUC; AGCGUT; AGCGTU; AACGTC; AACGCC; AACGTT; AACGCT; AACGUC; AACGUU; AACGCU; AACGUT; AACGTU; GGCGTT; GGCGCT; GGCGTC; GGCGCC; GGCGUU; GGCGCU; GGCGUC; GGCGUT; GGCGTU.

In some embodiments, the ISS comprises any of the following sequences:

GABGCT; GABGTC; GABGTT; GABGCC; GABGCU; GABGUC; GABGUU; GABGUT; GABGTU; AGBGTT; AGBGCT; AGBGTC; AGBGCC; AGBGUU; AGBGCU; AGBGUC; AGBGUT; AGBGTU; AABGTC; AABGCC; AABGTT; AABGCT; AABGUC; AABGUU; AABGCU; AABGUT; AABGTU; GGBGTT; GGBGCT; GGBGTC; GGBGCC; GGBGUU; GGBGCU; GGBGUC; GGBGUT; GGBGTU, where B is 5-bromocytosine.

In some embodiments, the ISS comprises any of the following sequences:

GABGCTCC; GABGTCCC; GABGTTCC; GABGCCCC; AGBGTTCC; AGBGCTCC; AGBGTCCC; AGBGCCCC; AABGTCCC; AABGCCCC; AABGTTCC; AABGCTCC; GGBGTTCC; GGBGCTCC; GGBGTCCC; GGBGCCCC; GABGCTCG; GABGTCCG; GABGCCCG; GABGTTCG; AGBGCTCG; AGBGTTCG; AGBGTCCG; AGBGCCCG; AABGTCCG; AABGCCCG; AABGTTCG; AABGCTCG; GGBGTTCG; GGBGCTCG; GGBGTCCG; GGBGCCCG; GABGCTBG; GABGTCBG; GABGCCBG; GABGTTBG; AGBGCTBG; AGBGTTBG; AGBGTCBG; AGBGCCBG; AABGTCBG; AABGCCBG; AABGTTBG; AABGCTBG; GGBGTTBG; GGBGCTBG; GGBGTCBG; GGBGCCBG, where B is 5-bromocytosine In some embodiments, the ISS comprises any of the following sequences:

GABGCUCC; GABGUCCC; GABGUTCC; GABGTUCC; GABGUUCC; AGBGUUCC; AGBGTUCC; AGBGUTCC; AGBGCUCC; AGBGUCCC; AABGUCCC; AABGUUCC; AABGUTCC; AABGTUCC; AABGCUCC; GGBGUUCC; GGBGUTCC; GGBGTUCC; GGBGCUCC; GGBGUCCC; GABGCUCG; GABGUCCG; GABGUUCG; GABGUTCG; GABGTUCG; AGBGCUCG; AGBGUUCG; AGBGUTCG; AGBGTUCG; AGBGUCCG; AABGUCCG; AABGUUCG; AABGUTCG; AABGTUCG; AABGCUCG; GGBGUUCG; GGBGUTCG; GGBGTUCG; GGBGCUCG; GGBGUCCG; GABGCUBG; GABGUCBG; GABGUUBG; GABGUTBG; GABGTUBG; AGBGCUBG; AGBGUUBG; AGBGUCBG; AGBGUTBG; AGBGTUBG; AABGUCBG; AABGUUBG; AABGUTBG; AABGTUBG; AABGCUBG; GGBGUUBG; GGBGUTBG; GGBGTUBG; GGBGCUBG; GGBGUCBG, where B is 5-bromocytosine.

In some embodiments, the immunomodulatory polynucleotide comprises the sequence 5'-TGACTGTGAACGT-TCGAGATGA-3' (SEQ ID NO:1). In other embodiments, the ISS comprises any of the sequences:

5'-TGACCGTGAACGTTCGAGATGA-3'; (SEQ ID NO:2)

5'-TCATCTCGAACGTTCCACAGTCA-3'; (SEQ ID NO:3)

5'-TGACTGTGAACGTTCCAGATGA-3'; (SEQ ID NO:4)

5'-TCCATAACGTTCGCCTAACGTTCGTC-3'; (SEQ ID NO:5)

5'-TGACTGTGAABGTTCCAGATGA-3', where B is 5-bromocytosine; (SEQ ID NO:6)

5'-TGACTGTGAANGTTCGAGATGA-3', where B is 5-bromocytosine; (SEQ ID NO:7)

5'-TGACTGTGAANGTTNGAGATGA-3', where B is 5-bromocytosine; (SEQ ID NO:8)

5'-TCGAGCGTTCT-3'; (SEQ ID NO:12)

5'-ATCGACTCTCGAGCGTTCTC-3' and (SEQ ID NO:13)

5'-TCGTCGTTTTGTCGTTTTGTCGTT-3'. (SEQ ID NO:14)

In some embodiments, an IMP (or ISS) can be 7 bases (or base pairs) or more. Accordingly, in some embodiments, the ISS comprises the sequence 5'-TCGX$_1$X$_2$X$_3$X$_4$-3' or 5'-UCGX$_1$X$_2$X$_3$X$_4$-3' wherein X$_1$, X$_2$, X$_3$, X$_4$ are nucleotides. In some embodiments, the ISS comprises any of the following sequences: 5'-TCGTTTT-3'; 5'-TCGAAAA-3'; 5'-TCGCCCC-3'; 5'-TCGGGGG-3'; 5'-TCGUUUU-3'; 5'-TCGIIII-3'; 5'-UCGTTTT-3'; 5'-UCGAAAA-3';

5'-UCGCCCC-3'; 5'-UCGGGGG-3'; 5'-UCGUUUU-3'; 5'-UCGIIII-3'. In some embodiments, the ISS comprises the sequence 5'-$X_1$TCG$X_2X_3X_4$-3' or 5'-$X_1$UCG$X_2X_3X_4$-3', wherein $X_1$, $X_2$, $X_3$, $X_4$ are nucleotides. In some embodiments, the ISS comprises any of the following sequences: 5'-TTCGTTT-3'; 5'-ATCGATT-3'; 5'-TUCGTTT-3'; 5'-AUCGATT-3'. In some embodiments, the ISS comprises the sequence 5'-$X_1X_2$TCG$X_3X_4$-3' or 5'-$X_1X_2$UCG$X_3X_4$-3', wherein $X_1$, $X_2$, $X_3$, $X_4$ are nucleotides. In some embodiments, the ISS comprises any of the following sequences: 5'-TTTCGTT-3'; 5'-AATCGAT-3'; 5'-TTUCGTT-3'; 5'-AAUCGAT-3'.

In some embodiments, the ISS comprises the sequence 5'-TCGTCG$X_1$-3', wherein $X_1$ is a nucleotide. In some embodiments, the ISS comprises any of the following sequences: 5'-TCGTCGA-3'; 5'-TCGTCGC-3'; 5'-TCGTCGG-3'; 5'-TCGTCGT-3'; 5'-TCGTCGU-3'; 5'-TCGTCGI-3'. In some embodiments, the ISS comprises the sequence 5'-TCGUCG$X_1$-3', 5'-UCGTCG$X_1$-3', or 5'-UCGUCG$X_1$-3', wherein $X_1$ is a nucleotide. In some embodiments, the ISS comprises any of the following sequences:

```
5'-TCGUCGA-3';  5'-TCGUCGC-3';  5'-TCGUCGG-3';

5'-TCGUCGT-3';  5'-TCGUCGU-3';  5'-TCGUCGI-3';

5'-UCGTCGA-3';  5'-UCGTCGC-3';  5'-UCGTCGG-3';

5'-UCGTCGT-3';  5'-UCGTCGU-3';  5'-UCGTCGI-3';

5'-UCGUCGA-3';  5'-UCGUCGC-3';  5'-UCGUCGG-3';

5'-UCGUCGT-3';  5'-UCGUCGU-3';  5'-UCGUCGI-3'.
```

In some embodiments, the ISS comprises the sequence 5'-T mC G$X_1X_2X_3X_4$-3' or 5'-U mC G$X_1X_2X_3X_4$-3', wherein $X_1$, $X_2$, $X_3$, $X_4$ are nucleotides and wherein mC is a modified cytosine as described herein. In some embodiments, the ISS comprises the sequence 5'-$X_1$T mC G$X_2X_3X_4$-3' or 5'-$X_1$U mC G$X_2X_3X_4$-3', wherein $X_1$, $X_2$, $X_3$, $X_4$ are nucleotides. In some embodiments, the ISS comprises the sequence 5'-$X_1X_2$T mC G$X_3X_4$-3' or 5'-$X_1X_2$U mC G$X_3X_4$-3', wherein $X_1$, $X_2$, $X_3$, $X_4$ are nucleotides.

In some embodiments, the ISS comprises the sequence 5'-T mC GTCG$X_1$-3', 5'-T mC GUCG$X_1$-3', 5'-U mC GTCG$X_1$-3' or 5'-U mC GUCG$X_1$-3', wherein $X_1$ is a nucleotide. In some embodiments, the ISS comprises the sequence 5'-TCGT mC G$X_1$-3', 5'-UCGT mC G$X_1$-3', 5'-TCGU mC G$X_1$-3' or 5'-UCGU mC G$X_1$-3', wherein $X_1$ is a nucleotide. In some embodiments, the ISS comprises the sequence 5'-T mC GT mC G$X_1$-3', 5'-U mC GT mC G$X_1$-3', 5'-T mC GU mC G$X_1$-3' or 5'-U mC GU mC G$X_1$-3', wherein $X_1$ is a nucleotide. As described herein, a modified cytosine (mC) includes addition of an electron-withdrawing moiety to C-5 and/or C-6 of a cytosine, including, but not limited to, C-5 halogenated cytosine, such as 5-bromocytosine.

Thus, in some embodiments, the ISS comprises any of the following sequences:

```
5'-TBGTTTT-3';  5'-TBGAAAA-3';  5'-TBGCCCC-3';

5'-TBGGGGG-3';  5'-TBGUUUU-3';  5'-TBGIIII-3';

5'-TBGTCGA-3';  5'-TBGTCGC-3';  5'-TBGTCGG-3';
```

-continued

```
5'-TBGTCGT-3';  5'-TBGTCGU-3';  5'-TBGTCGI-3';

5'-TCGTBGA-3';  5'-TCGTBGC-3';  5'-TCGTBGG-3';

5'-TCGTBGT-3';  5'-TCGTBGU-3';  5'-TCGTBGI-3';

5'-TBGTBGA-3';  5'-TBGTBGC-3';  5'-TBGTBGG-3';

5'-TBGTBGT-3',  5'-TBGTBGU-3';  5'-TBGTBGI-3';
``` where B is 5-bromocytosine.

In some embodiments, the polynucleotide of the IMP/MC consists of the sequence 5'-TCG$X_1X_2X_3X_4$-3' or 5'-UCG$X_1X_2X_3X_4$-3' wherein $X_1$, $X_2$, $X_3$, $X_4$ are nucleotides. In some embodiments, the polynucleotide of the IMP/MC consists of any of the following sequences:

```
5'-TCGTTTT-3';  5'-TCGAAAA-3';  5'-TCGCCCC-3';

5'-TCGGGGG-3';  5'-TCGUUUU-3';  5'-TCGIIII-3';

5'-UCGTTTT-3';  5'-UCGAAAA-3';  5'-UCGCCCC-3';

5'-UCGGGGG-3';  5'-UCGUUUU-3';  5'-UCGIIII-3'.
```

In some embodiments, the polynucleotide of the IMP/MC consists of the sequence 5'-$X_1$TCG$X_2X_3X_4$-3' or 5'-$X_1$UCG$X_2X_3X_4$-3', wherein $X_1$, $X_2$, $X_3$, $X_4$ are nucleotides. In some embodiments, the polynucleotide of the IMP/MC consists of any of the following sequences: 5'-TTCGTTT-3'; 5'-ATCGATT-3'; 5'-TUCGTTT-3'; 5'-AUCGATT-3'.

In some embodiments, the polynucleotide of the IMP/MC consists of the sequence 5'-$X_1X_2$TCG$X_3X_4$-3' or 5'-$X_1X_2$UCG$X_3X_4$-3', wherein $X_1$, $X_2$, $X_3$, $X_4$ are nucleotides. In some embodiments, the polynucleotide of the IMP/MC consists of any of the following sequences: 5'-TTTCGTT-3'; 5'-AATCGAT-3'; 5'-TTUCGTT-3'; 5'-AAUCGAT-3'.

In some embodiments, the polynucleotide of the IMP/MC consists of the sequence 5'-TCGTCG$X_1$-3', wherein $X_1$ is a nucleotide. In some embodiments, the polynucleotide of the IMP/MC consists of the sequence 5'-TCGTCGA-3'; 5'-TCGTCGC-3'; 5'-TCGTCGG-3'; 5'-TCGTCGT-3'; 5'-TCGTCGU-3'; 5'-TCGTCGI-3'. In some embodiments, the polynucleotide of the IMP/MC consists of the sequence 5'-TCGUCG$X_1$-3', 5'-UCGTCG$X_1$-3', or 5'-UCGUCG$X_1$-3', wherein $X_1$ is a nucleotide. In some embodiments, the polynucleotide of the IMP/MC consists of any of the following sequences:

```
5'-TCGUCGA-3';  5'-TCGUCGC-3';  5'-TCGUCGG-3';

5'-TCGUCGT-3';  5'-TCGUCGU-3';  5'-TCGUCGI-3';

5'-UCGTCGA-3';  5'-UCGTCGC-3';  5'-UCGTCGG-3';

5'-UCGTCGT-3';  5'-UCGTCGU-3';  5'-UCGTCGI-3';

5'-UCGUCGA-3';  5'-UCGUCGC-3';  5'-UCGUCGG-3';

5'-UCGUCGT-3';  5'-UCGUCGU-3';  5'-UCGUCGI-3'.
```

In some embodiments, the polynucleotide of the IMP/MC consists of the sequence 5'-T mC G$X_1X_2X_3X_4$-3' or 5'-U mC G$X_1X_2X_3X_4$-3', wherein $X_1$, $X_2$, $X_3$, $X_4$ are nucleotides and wherein mC is a modified cytosine as described herein. In some embodiments, the polynucleotide of the IMP/MC consists of the sequence 5'-X$_1$T mC GX$_2$X$_3$X$_4$-3' or 5'-X$_1$U mC GX$_2$X$_3$X$_4$-3', wherein X$_1$, X$_2$, X$_3$, X$_4$ are nucleotides. In some embodiments, the polynucleotide of the IMP/MC consists of the sequence 5'-X$_1$X$_2$T mC GX$_3$X$_4$-3' or 5'-X$_1$X$_2$U mC GX$_3$X$_4$-3', wherein X$_1$, X$_2$, X$_3$, X$_4$ are nucleotides.

In some embodiments, the polynucleotide of the IMP/MC consists of the sequence 5'-T mC GTCGX$_1$-3', 5'-T mC GUCGX$_1$-3', 5'-U mC GTCGX$_1$-3' or 5'-U mC GUCGX$_1$-3', wherein X$_1$ is a nucleotide. In some embodiments, the polynucleotide of the IMP/MC consists of the sequence 5'-TCGT mC GX$_1$-3', 5'-UCGT mC GX$_1$-3'. 5'-TCGU mC GX$_1$-3' or 5'-UCGU mC GX$_1$-3', wherein X$_1$ is a nucleotide. In some embodiments, the polynucleotide of the IMP/MC consists of the sequence 5'-T mC GT mC GX$_1$-3', 5'-U mC GT mC GX$_1$-3', 5'-T mC GU mC GX$_1$-3' or 5'-U mC GU mC GX$_1$-3', wherein X$_1$ is a nucleotide. As described herein, a modified cytosine (mC) includes addition of an electron-withdrawing moiety to C-5 and/or C-6 of a cytosine, including, but not limited to, C-5 halogenated cytosine, such as 5-bromocytosine.

Thus, in some embodiments, the polynucleotide of the IMP/MC consists of any of the following sequences:

```
5'-TBGTTTT-3'; 5'-TBGAAAA-3'; 5'-TBGCCCC-3';

5'-TBGGGGG-3'; 5'-TBGUUUU-3'; 5'-TBGIIII-3';

5'-TBGTCGA-3'; 5'-TBGTCGC-3'; 5'-TBGTCGG-3';

5'-TBGTCGT-3'; 5'-TBGTCGU-3'; 5'-TBGTCGI-3';

5'-TCGTBGA-3'; 5'-TCGTBGC-3'; 5'-TCGTBGG-3';

5'-TCGTBGT-3'; 5'-TCGTBGU-3'; 5'-TCGTBGI-3';

5'-TBGTBGA-3'; 5'-TBGTBGC-3'; 5'-TBGTBGG-3';

5'-TBGTBGT-3', 5'-TBGTBGU-3'; 5'-TBGTBGI-3';
``` where B is 5-bromocytosine.

An ISS and/or IMP may contain modifications. Modifications of ISS include any known in the art, but are not limited to, modifications of the 3'OH or 5'OH group, modifications of the nucleotide base, modifications of the sugar component, and modifications of the phosphate group. Various such modifications are described below.

It is preferred that cytosines present in the ISS are not methylated, however, in certain embodiments the ISS may contain on or more methylated cytosines. In such embodiments it is preferred that the cytosine of the 5'-CG-3' of the ISS is not methylated at the C-5 position. However, methylation at position N-4 is contemplated in those ISS with methylated cytosines.

An ISS and/or IMP may be single stranded or double stranded DNA, as well as single or double-stranded RNA or other modified polynucleotides. An ISS may or may not include one or more palindromic regions, which may be present in the motifs described above or may extend beyond the motif. An ISS may comprise additional flanking sequences, some of which are described herein. An ISS may contain naturally-occurring or modified, non-naturally occurring bases, and may contain modified sugar, phosphate, and/or termini. For example, phosphate modifications include, but are not limited to, methyl phosphonate, phosphorothioate, phosphoramidate (bridging or non-bridging), phosphotriester and phosphorodithioate and may be used in any combination. Other non-phosphate linkages may also be used. Preferably, oligonucleotides of the present invention comprise phosphodiester and/or phosphorothioate backbones. Sugar modifications known in the field, such as 2'-alkoxy-RNA analogs, 2'-amino-RNA analogs and 2'-alkoxy- or amino-RNA/DNA chimeras and others described herein, may also be made and combined with any phosphate modification. Examples of base modifications include, but are not limited to, addition of an electron-withdrawing moiety to C-5 and/or C-6 of a cytosine of the ISS (e.g., 5-bromocytosine, 5-chlorocytosine, 5-fluorocytosine, 5-iodocytosine). See, for example, International Patent Application No. WO 99/62923.

The ISS and/or IMP can be synthesized using techniques and nucleic acid synthesis equipment which are well known in the art including, but not limited to, enzymatic methods, chemical methods, and the degradation of larger oligonucleotide sequences. See, for example, Ausubel et al. (1987); and Sambrook et al. (1989). When assembled enzymatically, the individual units can be ligated, for example, with a ligase such as T4 DNA or RNA ligase. U.S. Pat. No. 5,124,246. Oligonucleotide degradation can be accomplished through the exposure of an oligonucleotide to a nuclease, as exemplified in U.S. Pat. No. 4,650,675.

The ISS and/or IMP can also be isolated using conventional polynucleotide isolation procedures. Such procedures include, but are not limited to, hybridization of probes to genomic or cDNA libraries to detect shared nucleotide sequences, antibody screening of expression libraries to detect shared structural features and synthesis of particular native sequences by the polymerase chain reaction.

Circular IMP can be isolated, synthesized through recombinant methods, or chemically synthesized. Where the circular IMP is obtained through isolation or through recombinant methods, the IMP will preferably be a plasmid. The chemical synthesis of smaller circular oligonucleotides can be performed using any method described in the literature. See, for instance, Gao et al. (1995) Nucleic Acids Res. 23:2025–2029; and Wang et al. (1994) Nucleic Acids Res. 22:2326–2333.

The techniques for making oligonucleotides and modified oligonucleotides are known in the art. Naturally occurring DNA or RNA, containing phosphodiester linkages, is generally synthesized by sequentially coupling the appropriate nucleoside phosphoramidite to the 5'-hydroxy group of the growing oligonucleotide attached to a solid support at the 3'-end, followed by oxidation of the intermediate phosphite triester to a phosphate triester. Once the desired oligonucleotide sequence has been synthesized, the oligonucleotide is removed from the support, the phosphate triester groups are deprotected to phosphate diesters and the nucleoside bases are deprotected using aqueous ammonia or other bases. See, for example, Beaucage (1993) "Oligodeoxyribonucleotide Synthesis" in Protocols for Oligonucleotides and Analogs, Synthesis and Properties (Agrawal, ed.) Humana Press, Totowa, N.J.; Warner et al. (1984) DNA 3:401 and U.S. Pat. No. 4,458,066.

The ISS and/or IMP can also contain phosphate-modified oligonucleotides. Synthesis of polynucleotides containing modified phosphate linkages or non-phosphate linkages is also know in the art. For a review, see Matteucci (1997) "Oligonucleotide Analogs: an Overview" in Oligonucleotides as Therapeutic Agents, (D. J. Chadwick and G. Cardew, ed.) John Wiley and Sons, New York, N.Y. The phosphorous derivative (or modified phosphate group) which can be attached to the sugar or sugar analog moiety in the oligonucleotides of the present invention can be a monophosphate, diphosphate, triphosphate, alkylphosphonate, phosphorothioate, phosphorodithioate or the like. The preparation of the above-noted phosphate analogs, and their incorporation into nucleotides, modified nucleotides and oligonucleotides, per se, is also known and need not be described here in detail. Peyrottes et al. (1996) Nucleic Acids Res. 24:1841–1848; Chaturvedi et al. (1996) Nucleic Acids Res. 24:2318–2323; and Schultz et al. (1996) Nucleic Acids Res. 24:2966–2973. For example, synthesis of phosphorothioate oligonucleotides is similar to that described above for naturally occurring oligonucleotides except that the oxidation step is replaced by a sulfurization step (Zon (1993) "Oligonucleoside Phosphorothioates" in Protocols for Oligonucleotides and Analogs, Synthesis and Properties (Agrawal, ed.) Humana Press, pp. 165–190). Similarly the synthesis of other phosphate analogs, such as phosphotriester (Miller et al. (1971) JACS 93:6657–6665), non-bridging phosphoramidates (Jager et al. (1988) Biochem. 27:7247–7246), N3' to P5' phosphoramidiates (Nelson et al. (1997) JOC 62:7278–7287) and phosphorodithioates (U.S. Pat. No. 5,453,496) has also been described. Other non-phosphorous based modified oligonucleotides can also be used (Stirchak et al. (1989) Nucleic Acids Res. 17:6129–6141). Oligonucleotides with phosphorothioate backbones can be more immunogenic than those with phosphodiester backbones and appear to be more resistant to degradation after injection into the host. Braun et al. (1988) J. Immunol. 141:2084–2089; and Latimer et al. (1995) Mol. Immunol. 32:1057–1064.

ISS-containing polynucleotides and/or IMPs used in the invention can comprise ribonucleotides (containing ribose as the only or principal sugar component), deoxyribonucleotides (containing deoxyribose as the principal sugar component), or, as is known in the art, modified sugars or sugar analogs can be incorporated in the ISS. Thus, in addition to ribose and deoxyribose, the sugar moiety can be pentose, deoxypentose, hexose, deoxyhexose, glucose, arabinose, xylose, lyxose, and a sugar "analog" cyclopentyl group. The sugar can be in pyranosyl or in a furanosyl form. In the ISS, the sugar moiety is preferably the furanoside of ribose, deoxyribose, arabinose or 2'-0-alkylribose, and the sugar can be attached to the respective heterocyclic bases either in α or β anomeric configuration. Sugar modifications include, but are not limited to, 2'-alkoxy-RNA analogs, 2'-amino-RNA analogs and 2'-alkoxy- or amino-RNA/DNA chimeras. The preparation of these sugars or sugar analogs and the respective "nucleosides" wherein such sugars or analogs are attached to a heterocyclic base (nucleic acid base) per se is known, and need not be described here, except to the extent such preparation can pertain to any specific example. Sugar modifications may also be made and combined with any phosphate modification in the preparation of an ISS and/or IMP.

The heterocyclic bases, or nucleic acid bases, which are incorporated in the ISS and/or IMP can be the naturally-occurring principal purine and pyrimidine bases, (namely uracil, thymine, cytosine, inosine, adenine and guanine, as mentioned above), as well as naturally-occurring and synthetic modifications of said principal bases.

Those skilled in the art will recognize that a large number of "synthetic" non-natural nucleosides comprising various heterocyclic bases and various sugar moieties (and sugar analogs) are available in the art, and that as long as other criteria of the present invention are satisfied, the ISS can include one or several heterocyclic bases other than the principal five base components of naturally-occurring nucleic acids. Preferably, however, the heterocyclic base in the ISS includes, but is not limited to, uracil-5-yl, cytosin-5-yl, adenin-7-yl, adenin-8-yl, guanin-7-yl, guanin-8-yl, 4-aminopyrrolo [2.3-d] pyrimidin-5-yl, 2-amino-4-oxopyrrolo [2,3-d] pyrimidin-5-yl, 2-amino-4-oxopyrrolo [2.3-d] pyrimidin-3-yl groups, where the purines are attached to the sugar moiety of the ISS via the 9-position, the pyrimidines via the 1-position, the pyrrolopyrimidines via the 7-position and the pyrazolopyrimidines via the 1-position.

The ISS and/or IMP may comprise at least one modified base as described, for example, in the commonly owned international application WO 99/62923. As used herein, the term "modified base" is synonymous with "base analog", for example, "modified cytosine" is synonymous with "cytosine analog." Similarly, "modified" nucleosides or nucleotides are herein defined as being synonymous with nucleoside or nucleotide "analogs." Examples of base modifications include, but are not limited to, addition of an electron-withdrawing moiety to C-5 and/or C-6 of a cytosine of the ISS. Preferably, the electron-withdrawing moiety is a halogen. Modified cytosines can include, but are not limited to, azacytosine, 5-bromocytosine, 5-chlorocytosine, chlorinated cytosine, cyclocytosine, cytosine arabinoside, 5-fluorocytosine, fluoropyrimidine, 5,6-dihydrocytosine, 5-iodocytosine, 5-nitrocytosine, 5-hydroxycytosine, and any other pyrimidine analog or modified pyrimidine. Preferred modified uracils are modified at C-5 and/or C-6, preferably with a halogen, and include, but are not limited to, bromouracil such as 5-bromouracil, chlorouracil such as 5-chlorouracil, fluorouracil such as 5-fluorouracil, iodouracil such as 5-iodouracil and hydroxyuracil. Also see, Kandimalla et al., 2001, Bioorg. Med. Chem. 9:807–813. See, for example, International Patent Application No. WO 99/62923. Other examples of base modifications include the addition of one or more thiol groups to the base including, but not limited to, 6-thio-guanine, 4-thio-thymine and 4-thio-uracil. Additionally, some IMPs may comprise modified bases such as 7-deazaguanosine in place of any guanosine residue, or a modified cytosine selected from N4-ethylcytosine or N4-methylcytosine in place of any cytosine residue, including the cytosine of the 5'-CG-3'.

The preparation of base-modified nucleosides, and the synthesis of modified oligonucleotides using said base-modified nucleosides as precursors, has been described, for example, in U.S. Pat. Nos. 4,910,300, 4,948,882, and 5,093,232. These base-modified nucleosides have been designed so that they can be incorporated by chemical synthesis into either terminal or internal positions of an oligonucleotide. Such base-modified nucleosides, present at either terminal or internal positions of an oligonucleotide, can serve as sites for attachment of a peptide or other antigen. Nucleosides modified in their sugar moiety have also been described (including, but not limited to, e.g., U.S. Pat. Nos. 4,849,513, 5,015,733, 5,118,800, 5,118,802) and can be used similarly.

As described herein, an IMP is any length greater than 6 bases or base pairs. Accordingly, in some embodiments, an IMP is less than about any of the following lengths (in bases or base pairs): 10,000; 5,000; 2500; 2000; 1500; 1250; 1000; 750; 500; 300; 250; 200; 175; 150; 125; 100; 75; 50; 25; 10; 8. In some embodiments, an IMP is greater than about any of the following lengths (in bases or base pairs): 6; 7; 8; 10; 15; 20; 25; 30; 40; 50; 60; 75; 100; 125; 150; 175; 200; 250; 300; 350; 400; 500; 750; 1000; 2000; 5000; 7500; 10000; 20000; 50000. Alternately, the ISS can be any of a range of sizes having an upper limit of 10,000; 5,000; 2500; 2000; 1500; 1250; 1000; 750; 500; 300; 250; 200; 175; 150; 125; 100; 75; 50; 25; 10; 8 or 7 and an independently selected lower limit of 7; 8; 10; 15; 20; 25; 30; 40; 50; 60; 75; 100;

125; 150; 175; 200; 250; 300; 350; 400; 500; 750; 1000; 2000; 5000; 7500, wherein the lower limit is less than the upper limit.

ISS have been described in the art and may be readily identified using standard assays which indicate various aspects of the immune response, such as cytokine secretion, antibody production, NK cell activation and T cell proliferation. See, e.g., WO 97/28259; WO 98/16247; WO 99/11275; Krieg et al. (1995) *Nature* 374:546–549; Yamamoto et al. (1992a); Ballas et al. (1996); Klinman et al. (1997); Sato et al. (1996); Pisetsky (1996a); Shimada et al. (1986) *Jpn. J. Cancer Res.* 77:808–816; Cowdery et al. (1996) *J. Immunol.* 156:4570–4575; Roman et al. (1997); and Lipford et al. (1997a). These methods are likewise applicable to assessing immunomodulatory activity of an IMP/MC complex.

One property of an IMP is the "isolated immunomodulatory activity" associated with the nucleotide sequence of the IMP. As noted above, the present inventors have discovered that, surprisingly, IMP/MC complexes exhibit immunomodulatory activity even when the IMP has a sequence that, if presented as a polynucleotide alone, does not exhibit comparable immunomodulatory activity.

In some embodiments, an IMP of an IMP/MC complex does not have "isolated immunomodulatory activity," or has "inferior isolated immunomodulatory activity," (i.e., when compared to the IMP/MC complex), as described below.

The "isolated immunomodulatory activity" of an IMP is determined by measuring the immunomodulatory activity of an isolated polynucleotide having the primary sequence of the IMP, and having the same nucleic acid backbone (e.g., phosphorothioate, phosphodiester, chimeric). To determine the independent immunomodulatory activity of, for example, an IMP in the IMP/MC complex, a test polynucleotide having the same sequence (e.g., 5'-TCGTCGA-3') and same backbone structure (e.g., phosphorothioate) is synthesized using routine methods, and its immunomodulatory activity (if any) is measured. Immunomodulatory activity can be determined using standard assays which indicate various aspects of the immune response, such as those described herein. For example, the human PBMC assay described herein is used. To account for donor variation, typically the assay is carried out in multiple donors. A polynucleotide does not have immunomodulatory activity (and the corresponding IMP does not have "isolated immunomodulatory activity") when the amount of IFN-γ secreted by PBMCs contacted with the polynucleotide is not significantly greater (e.g., less than about 2-fold greater) in the majority of donors than in the absence of the test compound or, (in some embodiments) in the presence of an inactive control compound (e.g., 5'-TGACTGTGAACCTTA-GAGATGA-3' (SEQ ID NO: 10)).

To compare the immunomodulatory activity of an IMP/MC complex and an isolated polynucleotide, immunomodulatory activity is measured, preferably, but not necessarily, using the human PBMC assay. Usually, the activity of two compounds is compared by assaying them in parallel under the same conditions (e.g., using the same cells), usually at a concentration of about 20 µg/ml. Generally, concentration is determined by measuring absorbance at 260 nm and using the conversion 0.5 $OD_{260}$/ml=20 µg/ml. This normalizes the amount of total nucleic acid in the test sample. Alternatively, concentration or weight can be measured by other methods known in the art.

An IMP of an IMP/MC complex is characterized as having "inferior immunomodulatory activity," when the test polynucleotide has less activity than the IMP/MC complex to which it is compared. Preferably the isolated immunomodulatory activity of the test polynucleotide is no more than about 50% of the activity of the IMP/MC complex, more preferably no more than about 20%, most preferably no more than about 10% of the activity of the IMP/MC complex, or in some embodiments, even less.

Microcarriers

Microcarriers useful in the invention are less than about 150, 120 or 100 µm in size, preferably less than about 50–60 µm in size, preferably less than about 10 µm in size, and are insoluble in pure water. Microcarriers may be solid phase (e.g., beads) or liquid phase (e.g., liposomes). Solid phase microcarriers are typically "beads" or other approximately spherical particles, although non-spherical particles are included within the invention. The microcarriers used in the invention are nonbiodegradable. A wide variety of solid phase materials acceptable for use as microcarriers are known in the art, as are formulations and methods for making nonbiodegradable liquid phase micrcaries.

Microcarriers for use in the compositions or methods of the invention are generally less than about 10 µm in size (e.g., have an average diameter of less than about 10 µm, or at least about 97% of the particles pass through a 10 µm screen filter), and include nanocarriers (i.e., carriers of less than about 1 µm size). Preferably, microcarriers are selected having sizes within an upper limit of about 9, 7, 5, 2, or 1 µm or 900, 800, 700, 600, 500, 400, 300, 250, 200, or 100 nm and an independently selected lower limit of about 4, 2, or 1 µm or about 800, 600, 500, 400, 300, 250, 200, 150, 100, 50, 25, or 10 nm, where the lower limit is less than the upper limit. In some embodiments, the microcarriers have a size of about 1.0–1.5 µm, about 1.0–2.0 µm or about 0.9–1.6 µm. In certain preferred embodiments, the microcarriers have a size of about 10 nm to about 5 µm or about 25 nm to about 4.5 µm, about 1 µm, about 1.2 µm, about 1.4 µm, about 1.5 µµm, about 1.6 µm, about 1.8 µm, about 2.0 µm, about 2.5 µm or about 4.5 µm. When the microcarriers are nanocarriers, preferred embodiments include nanocarriers of about 25 to about 300 nm, 50 to about 200 nm, about 50 nm or about 200 nm.

A wide variety of nonbiodegradable materials suitable for manufacturing microcarriers are also known, including, but not limited to, polystyrene, polypropylene, silica, ceramic, polyacrylamide, gold, latex, hydroxyapatite, dextran, and ferromagnetic and paramagnetic materials. Certain embodiments exclude gold, latex, and/or magnetic beads. In certain embodiments, the microcarriers may be made of a first material (e.g., a magnetic material) encapsulated with a second material (e.g., polystyrene).

Physico-chemical characteristics such as mean size, size distribution and surface charge of dried microspheres may be determined. Size characteristics are determined, for example, by a dynamic light scattering technique (preferably used for microcarriers of less than about 1–2 µm in nominal size) or an obscuration technique (preferably used for microcarriers of greater than about 1 µm in nominal size). Surface charge is preferably determined by measuring the zeta potential.

Liquid phase microcarriers include liposomes, micelles, oil droplets and other lipid or oil-based particles. Generally, liquid phase microcarriers incorporate one or more oils or lipids which are nonbiodegradable, such as a mineral oil. One preferred liquid phase microcarrier is oil droplets within an oil-in-water emulsion. In one preferred embodiment, the microcarrier is oil droplets in an oil-in-water emulsion prepared by emulsification of mineral oil, sorbitan trioleate, TWEEN 80® in an aqueous pH buffer.

Antigen

IMP/MC complexes may be prepared which comprise antigen or which are antigen-free, i.e., IMP/MC complexes not linked to an antigen. Any antigen may be used in the preparation of IMP/MC complexes comprising antigen.

In some embodiments, the antigen is an allergen. Examples of recombinant allergens are provided in Table 1. Preparation of many allergens is well-known in the art, including, but not limited to, preparation of ragweed pollen allergen Antigen E (Amb aI) (Rafnar et al. (1991) *J. Biol. Chem.* 266:1229–1236), major dust mite allergens Der pI and Der PII (Chua et al. (1988) *J. Exp. Med.* 167:175–182; Chua et al. (1990) *Int. Arch. Allergy Appl. Immunol.* 91:124–129), white birch pollen Bet vI (Breiteneder et al. (1989) *EMBO J.* 8:1935–1938), domestic cat allergen Fel d I (Rogers et al. (1993) *Mol Immunol.* 30:559–568), and protein antigens from tree pollen (Elsayed et al. (1991) *Scand. J. Clin. Lab. Invest. Suppl.* 204:17–31). As indicated, allergens from trees are known, including allergens from birch, juniper and Japanese cedar. Preparation of protein antigens from grass pollen for in vivo administration has been reported. Malley (1989) *J. Reprod. Immunol.* 16:173–186. As Table 1 indicates, in some embodiments, the allergen is a food allergen such as peanut allergen, for example Ara h I, and in some embodiments, the allergen is a grass allergen such as a rye allergen, for example Lol p 1. Table 1 shows a list of allergens that may be used.

TABLE 1

RECOMBINANT ALLERGENS

| Group | Allergen | Reference |
|---|---|---|
| ANIMALS: CRUSTACEA | | |
| Shrimp/lobster | tropomyosin | Leung et al. (1996) J. Allergy Clin. Immunol. 98: 954–961 |
| | Pan s I | Leung et al. (1998) Mol. Mar. Biol. Biotechnol. 7: 12–20 |
| INSECTS | | |
| Ant | Sol i 2 (venom) | Schmidt et al. J Allergy Clin Immunol., 1996, 98: 82–8 |
| Bee | Phospholipase A2 (PLA) | Muller et al. J Allergy Clin Immunol, 1995, 96: 395–402 |
| | | Forster et al. J Allergy Clin Immunol, 1995, 95: 1229–35 |
| | | Muller et al. Clin Exp Allergy, 1997, 27: 915–20 |
| | Hyaluronidase (Hya) | Soldatova et al. J Allergy Clin Immunol, 1998, 101: 691–8 |
| Cockroach | Bla g Bd9OK | Helm et al. J Allergy Clin Immunol, 1996, 98: 172–180 |
| | Bla g 4 (a calycin) | Vailes et al. J Allergy Clin Immunol, 1998, 101: 274–280 |
| | Glutathione S-transferase | Arruda et al. J Biol Chem, 1997, 272: 20907–12 |
| | Per a 3 | Wu et al. Mol Immunol, 1997, 34: 1–8 |
| Dust mite | Der p 2 (major allergen) | Lynch et al. J Allergy Clin Immunol, 1998, 101: 562–4 |
| | | Hakkaart et al. Clin Exp Allergy, 1998, 28: 169–74 |
| | | Hakkaart et al. Clin Exp Allergy, 1998, 28: 45–52 |
| | | Hakkaart et al. Int Arch Allergy Immunol, 1998, 115 (2): 150–6 |
| | | Mueller et al. J Biol Chem, 1997, 272: 26893–8 |
| | Der p2 variant | Smith et al. J Allergy Clin Immunol, 1998, 101: 423–5 |
| | Der f2 | Yasue et al. Clin Exp Immunol, 1998, 113: 1–9 |
| | | Yasue et al. Cell Immunol, 1997, 181: 30–7 |
| | Der p10 | Asturias et al. Biochim Biophys Acta, 1998, 1397: 27–30 |
| | Tyr p 2 | Eriksson et al. Eur J Biochem, 1998 |
| Hornet | Antigen 5 aka Dol m V (venom) | Tomalski et al. Arch Insect Biochem Physiol, 1993, 22: 303–13 |
| Mosquito | Aed a I (salivary apyrase) | Xu et al. Int Arch Allergy Immunol, 1998, 115: 245–51 |
| Yellow jacket | antigen 5, hyaluronidase and phospholipase (venom) | King et al. J Allergy Clin Immunol, 1996, 98: 588–600 |
| MAMMALS | | |
| Cat | Fel d I | Slunt et al. J Allergy Clin Immunol, 1995, 95: 1221–8 |
| | | Hoffmann et al. (1997) J Allergy Clin Immunol 99: 227–32 |
| | | Hedlin Curr Opin Pediatr, 1995, 7: 676–82 |
| Cow | Bos d 2 (dander; a lipocalin) | Zeiler et al. J Allergy Clin Immunol, 1997, 100: 721–7 |
| | | Rautiainen et al. Biochem Bioph. Res Comm., 1998, 247: 746–50 |
| | β-lactoglobulin (BLG, major cow milk allergen) | Chatel et al. Mol Immunol, 1996, 33: 1113–8 |
| | | Lehrer et al. Crit Rev Food Sci Nutr, 1996, 36: 553–64 |
| Dog | Can f I and Can f 2, salivary lipocalins | Konieczny et al. Immunology, 1997, 92: 577–86 |
| | | Spitzauer et al. J Allergy Clin Immunol, 1994, 93: 614–27 |
| | | Vrtala et al. J Immunol, 1998, 160: 6137–44 |
| Horse | Equ c1 (major allergen, a lipocalin) | Gregoire et al. J Biol Chem, 1996, 271: 32951–9 |
| Mouse | mouse urinary protein (MUP) | Konieczny et al. Immunology, 1997, 92: 577–86 |

TABLE 1-continued

RECOMBINANT ALLERGENS

| Group | Allergen | Reference |
|---|---|---|
| OTHER MAMMALIAN ALLERGENS | | |
| Insulin | | Ganz et al. J Allergy Clin Immunol, 1990, 86: 45–51 |
| | | Grammer et al. J Lab Clin Med, 1987, 109: 141–6 |
| | | Gonzalo et al. Allergy, 1998, 53: 106–7 |
| Interferons | interferon alpha 2c | Detmar et al. Contact Dermatis, 1989, 20: 149–50 |
| MOLLUSCS | topomyosin | Leung et al. J Allergy Clin Immunol, 1996, 98: 954–61 |
| PLANT ALLERGENS: | | |
| Barley | Hor v 9 | Astwood et al. Adv Exp Med Biol, 1996, 409: 269–77 |
| Birch | pollen allergen, Bet v 4 | Twardosz et al. Biochem Bioph. Res Comm., 1997, 239: 197 |
| | rBet v 1 Bet v 2: (profilin) | Pauli et al. J Allergy Clin Immunol, 1996, 97: 1100–9 |
| | | van Neerven et al. Clin Exp Allergy, 1998, 28: 423–33 |
| | | Jahn-Schmid et al. Immunotechnology, 1996, 2: 103–13 |
| | | Breitwieser et al. Biotechniques, 1996, 21: 918–25 |
| | | Fuchs et al. J Allergy Clin Immunol, 1997, 100: 3 56–64 |
| Brazil nut | globulin | Bartolome et al. Allergol Immunopathol, 1997, 25: 135–44 |
| Cherry | Pru a I (major allergen) | Scheurer et al. Mol Immunol, 1997, 34: 619–29 |
| Corn | Zml3 (pollen) | Heiss et al. FEBS Lett, 1996, 381: 217–21 |
| | | Lehrer et al. Int Arch Allergy Immunol, 1997, 113: 122–4 |
| Grass | Phl p 1, Phl p 2, Phl p 5 (timothy grass pollen) | Bufe et al. Am J Respir Crit Care Med, 1998, 157: 1269–76 |
| | | Vrtala et al. J Immunol Jun 15, 1998, 160: 6137–44 |
| | | Niederberger et al. J Allergy Clin Immun., 1998, 101: 258–64 |
| | Hol 1 5 velvet grass pollen | Schramm et al. Eur J Biochem, 1998, 252: 200–6 |
| | Bluegrass allergen | Zhang et al. J Immunol, 1993, 151: 791–9 |
| | Cyn d 7 Bermuda grass | Smith et al. Int Arch Allergy Immunol, 1997, 114: 265–71 |
| | Cyn d 12 (a profilin) | Asturias et al. Clin Exp Allergy, 1997, 27: 1307–13 |
| | | Fuchs et al. J Allergy Clin Immunol, 1997, 100: 356–64 |
| Japanese Cedar | Jun a 2 (*Juniperus ashei*) | Yokoyama et al. Biochem. Biophys. Res. Commun., 2000, 275: 195–202 |
| | Cry j 1, Cry j 2 (*Cryptomeria japonica*) | Kingetsu et al. Immunology, 2000, 99: 625–629 |
| Juniper | Jun o 2 (pollen) | Tinghino et al. J Allergy Clin Immunol, 1998, 101: 772–7 |
| Latex | Hev b 7 | Sowka et al. Eur J Biochem, 1998, 255: 213–9 |
| | | Fuchs et al. J Allergy Clin Immunol, 1997, 100: 3 56–64 |
| Mercurialis | Mer a I (profilin) | Vallverdu et al. J Allergy Clin Immunol, 1998, 101: 3 63–70 |
| Mustard (Yellow) | Sin a I (seed) | Gonzalez de la Pena et al. Biochem Bioph. Res Comm., 1993, 190: 648–53 |
| Oilseed rape | Bra r I pollen allergen | Smith et al. Int Arch Allergy Immunol, 1997, 114: 265–71 |
| Peanut | Ara h I | Stanley et al. Adv Exp Med Biol, 1996, 409: 213–6 |
| | | Burks et al. J Clin Invest, 1995, 96: 1715–21 |
| | | Burks et al. Int Arch Allergy Immunol, 1995, 107: 248–50 |
| *Poa pratensis* | Poa p9 | Parronchi et al. Eur J Immunol, 1996, 26: 697–703 |
| | | Astwood et al. Adv Exp Med Biol, 1996, 409: 269–77 |
| Ragweed | Amb a I | Sun et al. Biotechnology Aug, 1995, 13: 779–86 |
| | | Hirschwehr et al. J Allergy Clin Immunol, 1998, 101: 196–206 |
| | | Casale et al. J Allergy Clin Immunol, 1997, 100: 110–21 |
| Rye | Lol p I | Tamborini et al. Eur J Biochem, 1997, 249: 886–94 |
| Walnut | Jug r I | Teuber et al. J Allergy Clin Immun., 1998, 101: 807–14 |
| Wheat | allergen | Fuchs et al. J Allergy Clin Immunol, 1997, 100: 356–64 |
| | | Donovan et al. Electrophoresis, 1993, 14: 917–22 |
| FUNGI: | | |
| Aspergillus | Asp f 1, Asp f 2, Asp f 3, Asp f 4, rAsp f 6 | Crameri et al. Mycoses, 1998, 41 Suppl 1: 56–60 |
| | | Hemmann et al. Eur J Immunol, 1998, 28: 1155–60 |
| | | Banerjee et al. J Allergy Clin Immunol, 1997, 99: 821–7 |
| | | Crameri Int Arch Allergy Immunol, 1998, 115: 99–114 |
| | | Crameri et al. Adv Exp Med Biol, 1996, 409: 111–6 |
| | | Moser et al. J Allergy Clin Immunol, 1994, 93: 1–11 |
| | Manganese superoxide dismutase (MNSOD) | Mayer et al. Int Arch Allergy Immunol, 1997, 113: 213–5 |
| Blomia | allergen | Caraballo et al. Adv Exp Med Biol, 1996, 409: 81–3 |
| Penicillinium | allergen | Shen et al. Clin Exp Allergy, 1997, 27: 682–90 |
| Psilocybe | Psi c 2 | Horner et al. Int Arch Allergy Immunol, 1995, 107: 298–300 |

In some embodiments, the antigen is from an infectious agent, including protozoan, bacterial, fungal (including unicellular and multicellular), and viral infectious agents. Examples of suitable viral antigens are described herein and are known in the art. Bacteria include *Hemophilus influenza*, *Mycobacterium tuberculosis* and *Bordetella pertussis*. Protozoan infectious agents include malarial plasmodia, *Leishmania* species, *Trypanosoma* species and *Schistosoma* species. Fungi include *Candida albicans*.

In some embodiments, the antigen is a viral antigen. Viral polypeptide antigens include, but are not limited to, HIV proteins such as HIV gag proteins (including, but not limited to, membrane anchoring (MA) protein, core capsid (CA) protein and nucleocapsid (NC) protein), HIV polymerase, influenza virus matrix (M) protein and influenza virus nucleocapsid (NP) protein, hepatitis B surface antigen (HBsAg), hepatitis B core protein (HBcAg), hepatitis e protein (HBeAg), hepatitis B DNA polymerase, hepatitis C antigens, and the like. References discussing influenza vaccination include Scherle and Gerhard (1988) *Proc. Natl. Acad. Sci. USA* 85:4446–4450; Scherle and Gerhard (1986) *J. Exp. Med.* 164:1114–1128; Granoff et al. (1993) *Vaccine* 11:S46–51; Kodihalli et al. (1997) *J. Virol.* 71:3391–3396; Ahmeida et al. (1993) *Vaccine* 11:1302–1309; Chen et al. (1999) *Vaccine* 17:653–659; Govorkova and Smirnov (1997) *Acta Virol.* 41:251–257; Koide et al. (1995) *Vaccine* 13:3–5; Mbawuike et al. (1994) *Vaccine* 12:1340–1348; Tamura et al. (1994) *Vaccine* 12:310–316; Tamura et al. (1992) *Eur. J. Immunol.* 22:477–481; Hirabayashi et al. (1990) *Vaccine* 8:595–599. Other examples of antigen polypeptides are group- or sub-group specific antigens, which are known for a number of infectious agents, including, but not limited to, adenovirus, herpes simplex virus, papilloma virus, respiratory syncytial virus and poxviruses.

Many antigenic peptides and proteins are known, and available in the art; others can be identified using conventional techniques. For immunization against tumor formation or treatment of existing tumors, immunomodulatory peptides can include tumor cells (live or irradiated), tumor cell extracts, or protein subunits of tumor antigens such as Her-2/neu, Mart1, carcinoembryonic antigen (CEA), gangliosides, human milk fat globule (HMFG), mucin (MUC1), MAGE antigens, BAGE antigens, GAGE antigens, gp100, prostate specific antigen (PSA), and tyrosinase. Vaccines for immuno-based contraception can be formed by including sperm proteins administered with ISS. Lea et al. (1996) *Biochim. Biophys. Acta* 1307:263.

Attenuated and inactivated viruses are suitable for use herein as the antigen. Preparation of these viruses is well-known in the art and many are commercially available (see, e.g., Physicians' Desk Reference (1998) 52nd edition, Medical Economics Company, Inc.). For example, polio virus is available as IPOL® (Pasteur Merieux Connaught) and ORIMUNE® (Lederle Laboratories), hepatitis A virus as VAQTA® (Merck), measles virus as ATTENUVAX® (Merck), mumps virus as MUMPSVAX® (Merck) and rubella virus as MERUVAX®II (Merck). Additionally, attenuated and inactivated viruses such as HIV-1, HIV-2, herpes simplex virus, hepatitis B virus, rotavirus, human and non-human papillomavirus and slow brain viruses can provide peptide antigens.

In some embodiments, the antigen comprises a viral vector, such as vaccinia, adenovirus, and canary pox.

Antigens may be isolated from their source using purification techniques known in the art or, more conveniently, may be produced using recombinant methods.

Antigenic peptides can include purified native peptides, synthetic peptides, recombinant proteins, crude protein extracts, attenuated or inactivated viruses, cells, microorganisms, or fragments of such peptides. Immunomodulatory peptides can be native or synthesized chemically or enzymatically. Any method of chemical synthesis known in the art is suitable. Solution phase peptide synthesis can be used to construct peptides of moderate size or, for the chemical construction of peptides, solid phase synthesis can be employed. Atherton et al. (1981) *Hoppe Seylers Z. Physiol. Chem.* 362:833–839. Proteolytic enzymes can also be utilized to couple amino acids to produce peptides. Kullmann (1987) Enzymatic Peptide Synthesis, CRC Press, Inc. Alternatively, the peptide can be obtained by using the biochemical machinery of a cell, or by isolation from a biological source. Recombinant DNA techniques can be employed for the production of peptides. Hames et al. (1987) Transcription and Translation: A Practical Approach, IRL Press. Peptides can also be isolated using standard techniques such as affinity chromatography.

Preferably the antigens are peptides, lipids (e.g., sterols excluding cholesterol, fatty acids, and phospholipids), polysaccharides such as those used in H. influenza vaccines, gangliosides and glycoproteins. These can be obtained through several methods known in the art, including isolation and synthesis using chemical and enzymatic methods. In certain cases, such as for many sterols, fatty acids and phospholipids, the antigenic portions of the molecules are commercially available.

Examples of viral antigens useful in the subject compositions and methods using the compositions include, but are not limited to, HIV antigens. Such antigens include, but are not limited to, those antigens derived from HIV envelope glycoproteins including, but not limited to, gp160, gp120 and gp41. Numerous sequences for HIV genes and antigens are known. For example, the Los Alamos National Laboratory HIV Sequence Database collects, curates and annotates HIV nucleotide and amino acid sequences. This database is accessible via the internet, at http://hiv-web.lanl.gov/, and in a yearly publication, see Human Retroviruses and AIDS Compendium (for example, 1998 edition).

Antigens derived from infectious agents may be obtained using methods known in the art, for example, from native viral or bacterial extracts, from cells infected with the infectious agent, from purified polypeptides, from recombinantly produced polypeptides and/or as synthetic peptides.

IMP/MC complex formulations may be prepared with other immunotherapeutic agents including, but not limited to, cytokine, adjuvants and antibodies, such as anti-tumor antibodies and derivatives thereof. These IMP/MC complex formulations may be prepared with or without antigen.

IMP/MC Complexes

IMP/MC complexes comprise an IMP bound to the surface of, or inserted into, a microcarrier (i.e., the IMP is not encapsulated in the MC), and preferably comprise multiple molecules of IMP bound to each microcarrier. In certain embodiments, a mixture of different IMPs may be complexed with a microcarrier, such that the microcarrier is bound to more than one IMP species. The bond between the IMP and MC may be covalent or non-covalent. As will be understood by one of skill in the art, the IMP may be modified or derivatized and the composition of the microcarrier may be selected and/or modified to accommodate the desired type of binding desired for IMP/MC complex formation.

The instant invention provides methods of making IMP/MC complexes, as well as the products of such methods.

IMP/MC complexes are made by combining an IMP and an MC to form a complex. The specific process for combining the IMP and MC to form a complex will, of course, depend on the type and features of the MC as well as the mode of conjugation of the IMP and MC. When the MC is a solid phase MC, the IMP/MC complex is preferably made by contacting the IMP and the MC under conditions which promote complex formation (which will depend on the type of linkage used in the complex). When the MC is liquid phase, the IMP may be combined with a preformed MC under conditions which promote complex formation or be combined with the components of the MC prior to formation of the MC. In the situation where the IMP is combined with the components of a liquid phase MC, the process of making the MC may incorporate the IMP, thus resulting in the simultaneous creation of IMP/MC complexes, or when it does not, the process will involve an additional step under conditions which promote complex formation.

IMP/MC complexes in accordance with the invention are insoluble in pure water, and IMP/MC complex compositions are preferably free of acetonitrile, dichloroethane, toluene, and methylene chloride (dichlormethane).

Covalently bonded IMP/MC complexes may be linked using any covalent crosslinking technology known in the art. Typically, the IMP portion will be modified, either to incorporate an additional moiety (e.g., a free amine, carboxyl or sulfhydryl group) or incorporate modified (e.g., phosphorothioate) nucleotide bases to provide a site at which the IMP portion may be linked to the microcarrier. The link between the IMP and MC portions of the complex can be made at the 3' or 5' end of the IMP, or at a suitably modified base at an internal position in the IMP. The microcarrier is generally also modified to incorporate moieties through which a covalent link may be formed, although functional groups normally present on the microcarrier may also be utilized. The IMP/MC is formed by incubating the IMP with a microcarrier under conditions which permit the formation of a covalent complex (e.g., in the presence of a crosslinking agent or by use of an activated microcarrier comprising an activated moiety which will form a covalent bond with the IMP).

A wide variety of crosslinking technologies are known in the art, and include crosslinkers reactive with amino, carboxyl and sulfhydryl groups. As will be apparent to one of skill in the art, the selection of a crosslinking agent and crosslinking protocol will depend on the configuration of the IMP and the microcarrier as well as the desired final configuration of the IMP/MC complex. The crosslinker may be either homobifunctional or heterobifunctional. When a homobifunctional crosslinker is used, the crosslinker exploits the same moiety on the IMP and MC (e.g., an aldehyde crosslinker may be used to covalently link an IMP and MC where both the IMP and MC comprise one or more free amines). Heterobifunctional crosslinkers utilize different moieties on the IMP and MC, (e.g., a maleimido-N-hydroxysuccinimide ester may be used to covalently link a free sulfhydryl on the IMP and a free amine on the MC), and are preferred to minimize formation of inter-microcarrier bonds. In most cases, it is preferable to crosslink through a first crosslinking moiety on the microcarrier and a second crosslinking moiety on the IMP, where the second crosslinking moiety is not present on the microcarrier. One preferred method of producing the IMP/MC complex is by 'activating' the microcarrier by incubating with a heterobifunctional crosslinking agent, then forming the IMP/MC complex by incubating the IMP and activated MC under conditions appropriate for reaction. The crosslinker may incorporate a "spacer" arm between the reactive moieties, or the two reactive moieties in the crosslinker may be directly linked.

In one preferred embodiment, the IMP portion comprises at least one free sulfhydryl (e.g., provided by a 5'-thiol modified base or linker) for crosslinking to the microcarrier, while the microcarrier comprises free amine groups. A heterobifunctional crosslinker reactive with these two groups (e.g., a crosslinker comprising a maleimide group and a NHS-ester), such as succinimidyl 4-(N-maleimidomethyl)cyclohexane-1-carboxylate is used to activate the MC, then covalently crosslink the IMP to form the IMP/MC complex.

Non-covalent IMP/MC complexes may be linked by any non-covalent binding or interaction, including ionic (electrostatic) bonds, hydrophobic interactions, hydrogen bonds, van der Waals attractions, or a combination of two or more different interactions, as is normally the case when a binding pair is to link the IMP and MC.

Preferred non-covalent IMP/MC complexes are typically complexed by hydrophobic or electrostatic (ionic) interactions, or a combination thereof, (e.g., through base pairing between an IMP and a polynucleotide bound to an MC use of a binding pair). Due to the hydrophilic nature of the backbone of polynucleotides, IMP/MC complexes which rely on hydrophobic interactions to form the complex generally require modification of the IMP portion of the complex to incorporate a highly hydrophobic moiety. Preferably, the hydrophobic moiety is biocompatible, nonimmunogenic, and is naturally occurring in the individual for whom the composition is intended (e.g., is found in mammals, particularly humans). Examples of preferred hydrophobic moieties include lipids, steroids, sterols such as cholesterol, and terpenes. The method of linking the hydrophobic moiety to the IMP will, of course, depend on the configuration of the IMP and the identity of the hydrophobic moiety. The hydrophobic moiety may be added at any convenient site in the IMP, preferably at either the 5' or 3' end; in the case of addition of a cholesterol moiety to an IMP, the cholesterol moiety is preferably added to the 5' end of the IMP, using conventional chemical reactions (see, for example, Godard et al. (1995) *Eur. J. Biochem.* 232:404–410). Preferably, microcarriers for use in IMP/MC complexes linked by hydrophobic bonding are made from hydrophobic materials, such as oil droplets or hydrophobic polymers, although hydrophilic materials modified to incorporate hydrophobic moieties may be utilized as well. When the microcarrier is a liposome or other liquid phase microcarrier comprising a lumen, the IMP/MC complex is formed by mixing the IMP and the MC after preparation of the MC, in order to avoid encapsulation of the IMP during the MC preparation process.

Non-covalent IMP/MC complexes bound by electrostatic binding typically exploit the highly negative charge of the polynucleotide backbone. Accordingly, microcarriers for use in non-covalently bound IMP/MC complexes are generally positively charged (e.g., cationic) at physiological pH (e.g., about pH 6.8–7.4). The microcarrier may intrinsically possess a positive charge, but microcarriers made from compounds not normally possessing a positive charge may be derivatized or otherwise modified to become positively charged (e.g. cationic). For example, the polymer used to make the microcarrier may be derivatized to add positively charged groups, such as primary amines. Alternately, positively charged compounds may be incorporated in the formulation of the microcarrier during manufacture. Thus, microcarriers may comprise a positively charged moiety.

Generally, IMP/MC complexes can be preformed by adsorption onto cationic microspheres by incubation of IMP and the particles, preferably in an aqueous admixture. Such incubation may be carried out under any desired conditions, including ambient (room) temperature (e.g., approximately 20° C.) or under refrigeration (e.g., 4° C.). Because cationic microspheres and IMPs associate relatively quickly, the incubation may be for any convenient time period, such as 5, 10, 15 minutes or more, including overnight and longer incubations. However, because cationic microspheres and oligonucleotides spontaneously associate, the IMP/MC complex can be formed by simple co-administration of the oligonucleotide and the MC. Microspheres may be characterized for size and surface charge before and after IMP association. Selected batches may then evaluated for activity against suitable controls in, for example, established human peripheral blood mononuclear cell (PBMC) and mouse splenocyte assays, as described herein. The formulations may also evaluated in suitable animal models.

Non-covalent IMP/MC complexes linked by nucleotide base pairing may be produced using conventional methodologies. Generally, base-paired IMP/MC complexes are produced using a microcarrier comprising a bound, preferably a covalently bound, polynucleotide (the "capture polynucleotide") that is at least partially complementary to the IMP. The segment of complementarity between the IMP and the capture nucleotide is preferably at least 6, 8, 10 or 15 contiguous base pairs, more preferably at least 20 contiguous base pairs. The capture nucleotide may be bound to the MC by any method known in the art, and is preferably covalently abound to the IMP at the 5' or 3' end.

In other embodiments, a binding pair may be used to link the IMP and MC in an IMP/MC complex. The binding pair may be a receptor and ligand, an antibody and antigen (or epitope), or any other binding pair which binds at high affinity (e.g., $K_d$ less than about $10^{-8}$). One type of preferred binding pair is biotin and streptavidin or biotin and avidin, which form very tight complexes, although in certain embodiments this form of linkage may be excluded. When using a binding pair to mediate IMP/MC complex binding, the IMP is derivatized, typically by a covalent linkage, with one member of the binding pair, and the MC is derivatized with the other member of the binding pair. Mixture of the two derivatized compounds results in IMP/MC complex formation.

Many IMP/MC complex embodiments do not include an antigen, and certain embodiments exclude antigen(s) associated with the disease or disorder which is the object of the IMP/MC complex therapy. In further embodiments, the IMP is also bound to one or more antigen molecules. Antigen may be coupled with the IMP portion of an IMP/MC complex in a variety of ways, including covalent and/or non-covalent interactions, as described, for example, in WO 98/16247. Alternately, the antigen may be linked to the microcarrier (either directly or indirectly). Linkage of the antigen to the microcarrier can be accomplished by any of a large number of methods known in the art, including, but not limited to, direct covalent linkage, covalent conjugation via a crosslinker moiety (which may include a spacer arm), noncovalent conjugation via a specific binding pair (e.g., biotin and avidin), and noncovalent conjugation via electrostatic or hydrophobic bonding.

The link between the antigen and the IMP in IMP/MC complexes comprising an antigen bound to the IMP can be made at the 3' or 5' end of the IMP, or at a suitably modified base at an internal position in the IMP. If the antigen is a peptide and contains a suitable reactive group (e.g., an N-hydroxysuccinimide ester) it can be reacted directly with the $N^4$ amino group of cytosine residues. Depending on the number and location of cytosine residues in the IMP, specific coupling at one or more residues can be achieved.

Alternatively, modified nucleosides or nucleotides, such as are known in the art, can be incorporated at either terminus, or at internal positions in the IMP. These can contain blocked functional groups which, when deblocked, are reactive with a variety of functional groups which can be present on, or attached to, the antigen of interest.

Where the antigen is a peptide, this portion of the conjugate can be attached to the 3'-end of the IMP through solid support chemistry. For example, the IMP portion can be added to a polypeptide portion that has been pre-synthesized on a support. Haralambidis et al. (1990a) *Nucleic Acids Res.* 18:493–499; and Haralambidis et al. (1990b) *Nucleic Acids Res.* 18:501–505. Alternatively, the IMP can be synthesized such that it is connected to a solid support through a cleavable linker extending from the 3'-end. Upon chemical cleavage of the IMP from the support, a terminal thiol group is left at the 3'-end of the oligonucleotide (Zuckermann et al. (1987) *Nucleic Acids Res.* 15:5305–5321; and Corey et al. (1987) *Science* 238:1401–1403) or a terminal amino group is left at the 3'-end of the oligonucleotide (Nelson et al. (1989) *Nucleic Acids Res.* 17:1781–1794). Conjugation of the amino-modified IMP to amino groups of the peptide can be performed as described in Benoit et al. (1987) *Neuromethods* 6:43–72. Conjugation of the thiol-modified IMP to carboxyl groups of the peptide can be performed as described in Sinha et al. (1991), pp. 185–210, Oligonucleotide Analogues: A Practical Approach, IRL Press. Coupling of an oligonucleotide carrying an appended maleimide to the thiol side chain of a cysteine residue of a peptide has also been described. Tung et al. (1991) *Bioconjug. Chem.* 2:464–465.

The peptide portion of the conjugate can be attached to the 5'-end of the IMP through an amine, thiol, or carboxyl group that has been incorporated into the oligonucleotide during its synthesis. Preferably, while the oligonucleotide is fixed to the solid support, a linking group comprising a protected amine, thiol, or carboxyl at one end, and a phosphoramidite at the other, is covalently attached to the 5'-hydroxyl. Agrawal et al. (1986) *Nucleic Acids Res.* 14:6227–6245; Connolly (1985) *Nucleic Acids Res.* 13:4485–4502; Kremsky et al. (1987) *Nucleic Acids Res.* 15:2891–2909; Connolly (1987) *Nucleic Acids Res.* 15:3131–3139; Bischoff et al. (1987) *Anal. Biochem.* 164:336–344; Blanks et al. (1988) *Nucleic Acids Res.* 16:10283–10299; and U.S. Pat. Nos. 4,849,513, 5,015,733, 5,118,800, and 5,118,802. Subsequent to deprotection, the amine, thiol, and carboxyl functionalities can be used to covalently attach the oligonucleotide to a peptide. Benoit et al. (1987); and Sinha et al. (1991).

An IMP-antigen conjugate can also be formed through non-covalent interactions, such as ionic bonds, hydrophobic interactions, hydrogen bonds and/or van der Waals attractions.

Non-covalently linked conjugates can include a non-covalent interaction such as a biotin-streptavidin complex. A biotinyl group can be attached, for example, to a modified base of an ISS. Roget et al. (1989) *Nucleic Acids Res.* 17:7643–7651. Incorporation of a streptavidin moiety into the peptide portion allows formation of a non-covalently bound complex of the streptavidin conjugated peptide and the biotinylated oligonucleotide.

Non-covalent associations can also occur through ionic interactions involving an IMP and residues within the antigen, such as charged amino acids, or through the use of a linker portion comprising charged residues that can interact with both the oligonucleotide and the antigen. For example, non-covalent conjugation can occur between a generally negatively-charged ISS and positively-charged amino acid residues of a peptide, e.g., polylysine, polyarginine and polyhistidine residues.

Non-covalent conjugation between IMP and antigens can occur through DNA binding motifs of molecules that interact with DNA as their natural ligands. For example, such DNA binding motifs can be found in transcription factors and anti-DNA antibodies.

The linkage of the IMP to a lipid can be formed using standard methods. These methods include, but are not limited to, the synthesis of oligonucleotide-phospholipid conjugates (Yanagawa et al. (1988) *Nucleic Acids Symp. Ser.* 19:189–192), oligonucleotide-fatty acid conjugates (Grabarek et al. (1990) *Anal. Biochem.* 185:131–135; and Staros et al. (1986) *Anal. Biochem.* 156:220–222), and oligonucleotide-sterol conjugates. Boujrad et al. (1993) *Proc. Natl. Acad. Sci. USA* 90:5728–5731.

The linkage of the IMP to an oligosaccharide can be formed using standard known methods. These methods include, but are not limited to, the synthesis of oligonucleotide-oligosaccharide conjugates, wherein the oligosaccharide is a moiety of an immunoglobulin. O'Shannessy et al. (1985) *J. Applied Biochem.* 7:347–355.

The linkage of a circular IMP to a peptide or antigen can be formed in several ways. Where the circular IMP is synthesized using recombinant or chemical methods, a modified nucleoside is suitable. Ruth (1991), pp. 255–282, in Oligonucleotides and Analogues: A Practical Approach, IRL Press. Standard linking technology can then be used to connect the circular IMP to the antigen or other peptide. Goodchild (1990) *Bioconjug. Chem.* 1:165. Where the circular IMP is isolated, or synthesized using recombinant or chemical methods, the linkage can be formed by chemically activating, or photoactivating, a reactive group (e.g. carbene, radical) that has been incorporated into the antigen or other peptide.

Additional methods for the attachment of peptides and other molecules to oligonucleotides can be found in U.S. Pat. No. 5,391,723; Kessler (1992) "Nonradioactive labeling methods for nucleic acids" in Kricka (ed.) Nonisotopic DNA Probe Techniques, Academic Press; and Geoghegan et al. (1992) *Bioconjug. Chem.* 3:138–146.

METHODS OF THE INVENTION

The invention provides methods of modulating an immune response in an individual, preferably a mammal, more preferably a human, comprising administering to the individual an IMP/MC complex (typically in a composition comprising the complex and a pharmaceutically acceptable excipient) such that the desired modulation of the immune response is achieved. Immunomodulation may include stimulating a Th1-type immune response and/or inhibiting or reducing a Th2-type immune response. As described herein, modulation of an immune response may be humoral and/or cellular, and is measured using standard techniques in the art and as described herein.

In some embodiments, the immune modulation comprises stimulating a (i.e., one or more) Th1-associated cytokine, such as IFN-$\gamma$, IL-12 and/or IFN-$\alpha$. In some embodiments, the immune modulation comprises suppressing production of a (i.e., one or more) Th2-associated cytokine, such as IL-4 and/or IL-5. Measuring these parameters uses methods standard in the art and has been discussed herein.

As described herein, administration of IMP/MC may further comprise administration of one or more additional immunotherapeutic agents (i.e., an agent which acts via the immune system and/or is derived from the immune system) including, but not limited to, cytokine, adjuvants and antibodies. Examples of therapeutic antibodies include those used in the cancer context (e.g., anti-tumor antibodies). Administration of such additional immunotherapeutic agents applies to all the methods described herein.

In certain embodiments, the individual suffers from a disorder associated with a Th2-type immune response, such as allergies or allergy-induced asthma. Administration of an IMP/MC complex results in immunomodulation, increasing levels of one or more Th1-type response associated cytokines, which may result in a reduction of the Th2-type response features associated with the individual's response to the allergen. Immunomodulation of individuals with Th2-type response associated disorders results in a reduction or improvement in one or more of the symptoms of the disorder. Where the disorder is allergy or allergy-induced asthma, improvement in one or more of the symptoms includes a reduction one or more of the following: rhinitis, allergic conjunctivitis, circulating levels of IgE, circulating levels of histamine and/or requirement for 'rescue' inhaler therapy (e.g., inhaled albuterol administered by metered dose inhaler or nebulizer).

In further embodiments, the individual subject to the immunomodulatory therapy of the invention is an individual receiving a vaccine. The vaccine may be a prophylactic vaccine or a therapeutic vaccine. A prophylactic vaccine comprises one or more epitopes associated with a disorder for which the individual may be at risk (e.g., *M. tuberculosis* antigens as a vaccine for prevention of *tuberculosis*). Therapeutic vaccines comprise one or more epitopes associated with a particular disorder affecting the individual, such as *M. tuberculosis* or *M. bovis* surface antigens in tuberculosis patients, antigens to which the individual is allergic (i.e., allergy desensitization therapy) in individuals subject to allergies, tumor cells from an individual with cancer (e.g., as described in U.S. Pat. No. 5,484,596), or tumor associated antigens in cancer patients. The IMP/MC complex may be given in conjunction with the vaccine (e.g., in the same injection or a contemporaneous, but separate, injection) or the IMP/MC complex may be administered separately (e.g., at least 12 hours before or after administration of the vaccine). In certain embodiments, the antigen(s) of the vaccine is part of the IMP/MC complex, by either covalent or non-covalent linkage to the IMP/MC complex. Administration of IMP/MC complex therapy to an individual receiving a vaccine results in an immune response to the vaccine that is shifted towards a Th1-type response as compared to individuals which receive vaccine without IMP/MC complex. Shifting towards a Th1-type response may be recognized by a delayed-type hypersensitivity (DTH) response to the antigen(s) in the vaccine, increased IFN-$\gamma$ and other Th1-type response associated cytokines, increased IFN-$\alpha$, production of CTLs specific for the antigen(s) of the vaccine, low or reduced levels of IgE specific for the antigen(s) of the vaccine, a reduction in Th2-associated antibodies specific for the antigen(s) of the vaccine, and/or an increase in Th1-associated antibodies specific for the antigen(s) of the vaccine. In the case of therapeutic vaccines, administration of IMP/MC complex and vaccine also results in amelioration of the symptoms of the disorder which the vaccine is intended to treat. As will be apparent to one of skill in the art, the exact symptoms and manner of their improvement will depend on the disorder sought to be treated. For example, where the therapeutic vaccine is for tuberculosis, IMP/MC complex treatment with vaccine results in reduced coughing, pleural or chest wall pain, fever, and/or other symptoms known in the art. Where the vaccine is an allergen used in allergy desensitization therapy, the treatment results in a reduction in one or more symptoms of allergy (e.g., reduction in rhinitis, allergic conjunctivitis, circulating levels of IgE, and/or circulating levels of histamine).

Other embodiments of the invention relate to immunomodulatory therapy of individuals having a pre-existing disease or disorder, such as cancer or an infectious disease. Cancer is an attractive target for immunomodulation because most cancers express tumor-associated and/or tumor specific antigens which are not found on other cells in the body. Stimulation of a Th1-type response against tumor cells results in direct and/or bystander killing of tumor cells by the immune system, leading to a reduction in cancer cells and a reduction in symptoms. Administration of an IMP/MC complex to an individual having cancer results in stimulation of a Th1-type immune response against the tumor cells. Such an immune response can kill tumor cells, either by direct action of cellular immune system cells (e.g., CTLs) or components of the humoral immune system, or by bystander effects on cells proximal to cells targeted by the immune system. In the cancer context, administration of IMP/MC complex may further comprise administration of one or more additional therapeutic agents such as, for example, anti-tumor antibodies, chemotherapy regimens and/or radiation treatments. Anti-tumor antibodies, including, but not limited to anti-tumor antibody fragments and/or derivatives thereof, and monoclonal anti-tumor antibodies, fragments and/or derivatives thereof, are known in the art as is administration of such antibody reagents in cancer therapy (e.g., Rituxan® (rituximab); Herceptin® (trastuzumab)). Administration of one or more additional therapeutic agents may occur before, after and/or concurrent with administration of the IMP/MC complexes.

Immunomodulatory therapy in accordance with the invention is also useful for individuals with infectious diseases, particularly infectious diseases which are resistant to humoral immune responses (e.g., diseases caused by mycobacterial infections and intracellular pathogens). Immunomodulatory therapy may be used for the treatment of infectious diseases caused by cellular pathogens (e.g., bacteria or protozoans) or by subcellular pathogens (e.g., viruses). IMP/MC complex therapy may be administered to individuals suffering from mycobacterial diseases such as tuberculosis (e.g., *M. tuberculosis* and/or *M. bovis* infections), leprosy (i.e., *M. leprae* infections), or *M. marinum* or *M. ulcerans* infections. IMP/MC complex therapy is also useful for the treatment of viral infections, including infections by influenza virus, respiratory syncytial virus (RSV), hepatitis virus B, hepatitis virus C, herpes viruses, particularly herpes simplex viruses, and papilloma viruses. Diseases caused by intracellular parasites such as malaria (e.g., infection by *Plasmodium vivax, P. ovale, P. falciparum* and/or *P. malariae*), leishmaniasis (e.g., infection by *Leishmania donovani, L. tropica, L. mexicana, L. braziliensis, L. peruviana, L. infantum, L. chagasi,* and/or *L. aethiopica*), and toxoplasmosis (i.e., infection by *Toxoplasmosis gondii*) also benefit from IMP/MC complex therapy. IMP/MC therapy is also useful for treatment of parasitic diseases such as schistosomiasis (i.e., infection by blood flukes of the genus *Schistosoma* such as *S. haematobium, S. mansoni, S. japonicum,* and *S. mekongi*) and clonorchiasis (i.e., infection by *Clonorchis sinensis*). Administration of an IMP/MC complex to an individual suffering from an infectious disease results in an amelioration of one or more symptoms of the infectious disease. In some embodiments, the infectious disease is not a viral disease.

The invention further provides methods of increasing at least one Th1-associated cytokine in an individual, including IL-2, IL-12, TNF-β, and IFN-γ. In certain embodiments, the invention provides methods of increasing IFN-γ in an individual, particularly in an individual in need of increased IFN-γ levels, by administering an effective amount of an IMP/MC complex to the individual. Individuals in need of increased IFN-γ are those having disorders which respond to the administration of IFN-γ. Such disorders include a number of inflammatory disorders including, but not limited to, ulcerative colitis. Such disorders also include a number of fibrotic disorders, including, but not limited to, idiopathic pulmonary fibrosis (IPF), scleroderma, cutaneous radiation-induced fibrosis, hepatic fibrosis including schistosomiasis-induced hepatic fibrosis, renal fibrosis as well as other conditions which may be improved by administration of IFN-γ. Administration of IMP/MC complex in accordance with the invention results in an increase in IFN-γ levels, and results in amelioration of one or more symptoms, stabilization of one or more symptoms, or prevention of progression (e.g., reduction or elimination of additional lesions or symptoms) of the disorder which responds to IFN-γ. The methods of the invention may be practiced in combination with other therapies which make up the standard of care for the disorder, such as administration of anti-inflammatory agents such as systemic corticosteroid therapy (e.g., cortisone) in IPF.

In certain embodiments, the invention provides methods of increasing IFN-α in an individual, particularly in an individual in need of increased IFN-α levels, by administering an effective amount of an IMP/MC complex to the individual such that IFN-α levels are increased. Individuals in need of increased IFN-α are those having disorders which respond to the administration of IFN-α, including recombinant IFN-α, including, but not limited to, viral infections and cancer. Accordingly, administration of an IMP/MC complex in accordance with the invention results in an increase in IFN-α levels, and results in amelioration of one or more symptoms, stabilization of one or more symptoms, and/or prevention of progression (e.g., reduction or elimination of additional lesions or symptoms) of the disorder which responds to IFN-α. The methods of the invention may be practiced in combination with other therapies which make up the standard of care for the disorder, such as administration of anti-viral agents for viral infections.

Also provided are methods of reducing levels, particularly serum levels, of IgE in an individual having an IgE-related disorder by administering an effective amount of an IMP/MC complex to the individual such that levels of IgE are reduced. Reduction in IgE results in an amelioration of symptoms of the IgE-related disorder. Such symptoms include allergy symptoms such as rhinitis, conjunctivitis, in decreased sensitivity to allergens, a reduction in the symptoms of allergy in an individual with allergies, or a reduction in severity of a allergic response.

As will be apparent to one of skill in the art, the methods of the invention may be practiced in combination with other therapies for the particular indication for which the IMP/MC complex is administered. For example, IMP/MC complex therapy may be administered in conjunction with anti-malarial drugs such as chloroquine for malaria patients, in conjunction with leishmanicidal drugs such as pentamidine and/or allopurinol for leishmaniasis patients, in conjunction with anti-mycobacterial drugs such as isoniazid, rifampin and/or ethambutol in tuberculosis patients, or in conjunction with allergen desensitization therapy for atopic (allergy) patients.

Administration and Assessment of the Immune Response

The IMP/MC complex can be administered in combination with other pharmaceutical and/or immunogenic and/or immunostimulatory agents and can be combined with a physiologically acceptable carrier thereof.

Accordingly, the IMP/MC complex can be administered in conjunction with other immunotherapeutic agents including, but not limited to, cytokine, adjuvants and antibodies.

The ISS-containing polynucleotide may be any of those described above. As indicated in SEQ ID NO: 1, preferably, the ISS-containing polynucleotide administered comprises the sequence 5'-T, C, G-3'. Preferably, the ISS-containing polynucleotide administered comprises the formula 5' purine, purine, C, G, pyrimidine, pyrimidine, C, G-3'; more preferably, 5'-A, A, C, G, T, T, C, G-3'. Another preferred embodiment uses a polynucleotide comprising the sequence 5'-CG-3' and further comprising the sequence 5'-TCG-3'. Another preferred embodiment uses SEQ ID NO:1. Another preferred embodiment uses a polynucleotide comprising or, alternatively, consisting of, the sequence selected from the group consisting of 5'-TCGX$_1$X$_2$X$_3$X$_4$-3', 5'-X$_1$TCGX$_2$X$_3$X$_4$-3' and 5'-X$_1$X$_2$TCGX$_3$X$_4$-3', wherein X$_1$, X$_2$, X$_3$, X$_4$ are nucleotides.

The IMP/MC complex may comprise any combination of the IMPs and MCs described above, so long as the IMP/MC is active. Generally, in some embodiments, an IMP/MC complex will be considered active if it has an activity (i.e., affects a measurable immune response as measured in vitro, in vivo and/or ex vivo) of at least about two times, preferably at least about three times, more preferably at least about five times, even more preferably at least about ten times the activity of a negative control in at least one assay of activity. Methods of assessing a measurable immune response are well known in the art, and include the human PBMC assay disclosed herein.

As with all immunogenic compositions, the immunologically effective amounts and method of administration of the particular IMP/MC complex formulation can vary based on the individual, what condition is to be treated and other factors evident to one skilled in the art. Factors to be considered include the antigenicity, whether or not the IMP/MC complex will be administered with or covalently attached to an adjuvant or delivery molecule, route of administration and the number of immunizing doses to be administered. Such factors are known in the art and it is well within the skill of those in the art to make such determinations without undue experimentation. A suitable dosage range is one that provides the desired modulation of immune response to the antigen. Generally, dosage is determined by the amount of IMP administered to the patient, rather than the overall quantity of IMP/MC complex. Useful dosage ranges of the IMP/MC complex, given in amounts of IMP delivered, may be, for example, from about any of the following: 0.1 to 100 µg/kg, 0.1 to 50 µg/kg, 0.1 to 25 µg/kg, 0.1 to 10 µg/kg, 1 to 500 µg/kg, 100 to 400 µg/kg, 200 to 300 µg/kg, 1 to 100 µg/kg, 100 to 200 µg/kg, 300 to 400 µg/kg, 400 to 500 µg/kg. Alternatively, the doses can be about any of the following: 0.1 µg, 0.25 µg, 0.5 µg, 1.0 µg, 2.0 µg, 5.0 µg, 10 µg, 25 µg, 50 µg, 75 µg, 100 µg. Accordingly, dose ranges can be those with a lower limit about any of the following: 0.1 µg, 0.25 µg, 0.5 µg and 1.0 µg; and with an upper limit of about any of the following: 25 µg, 50 µg and 100 µg. The absolute amount given to each patient depends on pharmacological properties such as bioavailability, clearance rate and route of administration.

The effective amount and method of administration of the particular IMP/MC complex formulation can vary based on the individual patient and the stage of the disease and other factors evident to one skilled in the art. The route(s) of administration useful in a particular application are apparent to one of skill in the art. Routes of administration include but are not limited to topical, dermal, transdermal, transmucosal, epidermal, parenteral, gastrointestinal, and naso-pharyngeal and pulmonary, including transbronchial and transalveolar. A suitable dosage range is one that provides sufficient ISS-containing composition to attain a tissue concentration of about 1–10 µM as measured by blood levels. The absolute amount given to each patient depends on pharmacological properties such as bioavailability, clearance rate and route of administration.

As described herein, APCs and tissues with high concentration of APCs are preferred targets for the IMP/MC complexes. Thus, administration of IMP/MC complex to mammalian skin and/or mucosa, where APCs are present in relatively high concentration, is preferred.

The present invention provides IMP/MC complex formulations suitable for topical application including, but not limited to, physiologically acceptable implants, ointments, creams, rinses and gels. Topical administration is, for instance, by a dressing or bandage having dispersed therein a delivery system, by direct administration of a delivery system into incisions or open wounds, or by transdermal administration device directed at a site of interest. Creams, rinses, gels or ointments having dispersed therein an IMP/MC complex are suitable for use as topical ointments or wound filling agents.

Preferred routes of dermal administration are those which are least invasive. Preferred among these means are transdermal transmission, epidermal administration and subcutaneous injection. Of these means, epidermal administration is preferred for the greater concentrations of APCs expected to be in intradermal tissue.

Transdermal administration is accomplished by application of a cream, rinse, gel, etc. capable of allowing the IMP/MC complex to penetrate the skin and enter the blood stream. Compositions suitable for transdermal administration include, but are not limited to, pharmaceutically acceptable suspensions, oils, creams and ointments applied directly to the skin or incorporated into a protective carrier such as a transdermal device (so-called "patch"). Examples of suitable creams, ointments etc. can be found, for instance, in the Physician's Desk Reference.

For transdermal transmission, iontophoresis is a suitable method. Iontophoretic transmission can be accomplished using commercially available patches which deliver their product continuously through unbroken skin for periods of several days or more. Use of this method allows for controlled transmission of pharmaceutical compositions in relatively great concentrations, permits infusion of combination drugs and allows for contemporaneous use of an absorption promoter.

An exemplary patch product for use in this method is the LECTRO PATCH trademarked product of General Medical Company of Los Angeles, Calif. This product electronically maintains reservoir electrodes at neutral pH and can be adapted to provide dosages of differing concentrations, to dose continuously and/or periodically. Preparation and use of the patch should be performed according to the manufacturer's printed instructions which accompany the LEC- TRO PATCH product; those instructions are incorporated herein by this reference. Other occlusive patch systems are also suitable.

For transdermal transmission, low-frequency ultrasonic delivery is also a suitable method. Mitragotri et al. (1995) Science 269:850–853. Application of low-frequency ultrasonic frequencies (about 1 MHz) allows the general controlled delivery of therapeutic compositions, including those of high molecular weight.

Epidermal administration essentially involves mechanically or chemically irritating the outermost layer of the epidermis sufficiently to provoke an immune response to the irritant. Specifically, the irritation should be sufficient to attract APCs to the site of irritation.

An exemplary mechanical irritant means employs a multiplicity of very narrow diameter, short tines which can be used to irritate the skin and attract APCs to the site of irritation, to take up IMP/MC complex transferred from the end of the tines. For example, the MONO-VACC old tuberculin test manufactured by Pasteur Merieux of Lyon, France contains a device suitable for introduction of IMP/MC complex-containing compositions.

The device (which is distributed in the U.S. by Connaught Laboratories, Inc. of Swiftwater, Pa.) consists of a plastic container having a syringe plunger at one end and a tine disk at the other. The tine disk supports a multiplicity of narrow diameter tines of a length which will just scratch the outermost layer of epidermal cells. Each of the tines in the MONO-VACC kit is coated with old tuberculin; in the present invention, each needle is coated with a pharmaceutical composition of IMP/MC complex formulation. Use of the device is preferably according to the manufacturer's written instructions included with the device product. Similar devices which can also be used in this embodiment are those which are currently used to perform allergy tests.

Another suitable approach to epidermal administration of IMP/MC complex is by use of a chemical which irritates the outermost cells of the epidermis, thus provoking a sufficient immune response to attract APCs to the area. An example is a keratinolytic agent, such as the salicylic acid used in the commercially available topical depilatory creme sold by Noxema Corporation under the trademark NAIR. This approach can also be used to achieve epithelial administration in the mucosa. The chemical irritant can also be applied in conjunction with the mechanical irritant (as, for example, would occur if the MONO-VACC type tine were also coated with the chemical irritant). The IMP/MC complex can be suspended in a carrier which also contains the chemical irritant or coadministered therewith.

Parenteral routes of administration include but are not limited to electrical (iontophoresis) or direct injection such as direct injection into a central venous line, intravenous, intramuscular, intraperitoneal, intradermal, or subcutaneous injection. IMP/MC formulations suitable for parenteral administration are generally formulated in USP water or water for injection and may further comprise pH buffers, salts bulking agents, preservatives, and other pharmaceutically acceptable excipients. IMP/MC complexes for parenteral injection may be formulated in pharmaceutically acceptable sterile isotonic solutions such as saline and phosphate buffered saline for injection.

Gastrointestinal routes of administration include, but are not limited to, ingestion and rectal. The invention includes IMP/MC complex formulations suitable for gastrointestinal administration including, but not limited to, pharmaceutically acceptable powders, pills or liquids for ingestion and suppositories for rectal administration. As will be apparent to one of skill in the art, pills or suppositories will further comprise pharmaceutically acceptable solids, such as starch, to provide bulk for the composition.

Naso-pharyngeal and pulmonary administration include are accomplished by inhalation, and include delivery routes such as intranasal, transbronchial and transalveolar routes. The invention includes IMP/MC complex formulations suitable for administration by inhalation including, but not limited to, liquid suspensions for forming aerosols as well as powder forms for dry powder inhalation delivery systems. Devices suitable for administration by inhalation of IMP/MC complex formulations include, but are not limited to, atomizers, vaporizers, nebulizers, and dry powder inhalation delivery devices.

The choice of delivery routes can be used to modulate the immune response elicited. For example, IgG titers and CTL activities were identical when an influenza virus vector was administered via intramuscular or epidermal (gene gun) routes; however, the muscular inoculation yielded primarily IgG2a, while the epidermal route yielded mostly IgG1. Pertmer et al. (1996) *J. Virol.* 70:6119–6125. Thus, one skilled in the art can take advantage of slight differences in immunogenicity elicited by different routes of administering the immunomodulatory oligonucleotides of the present invention.

The above-mentioned compositions and methods of administration are meant to describe but not limit the methods of administering the IMP/MC complex formulations of the invention. The methods of producing the various compositions and devices are within the ability of one skilled in the art and are not described in detail here.

Analysis (both qualitative and quantitative) of the immune response to IMP/MC complex formulations can be by any method known in the art, including, but not limited to, measuring antigen-specific antibody production (including measuring specific antibody subclasses), activation of specific populations of lymphocytes such as CD4+ T cells or NK cells, production of cytokines such as IFN-γ, IFN-α, IL-2, IL-4, IL-5, IL-10 or IL-12 and/or release of histamine. Methods for measuring specific antibody responses include enzyme-linked immunosorbent assay (ELISA) and are well known in the art. Measurement of numbers of specific types of lymphocytes such as CD4+ T cells can be achieved, for example, with fluorescence-activated cell sorting (FACS). Cytotoxicity assays can be performed for instance as described in Raz et al. (1994) *Proc. Natl. Acad. Sci. USA* 91:9519–9523. Cytokine concentrations can be measured, for example, by ELISA. These and other assays to evaluate the immune response to an immunogen are well known in the art. See, for example, Selected Methods in Cellular Immunology (1980) Mishell and Shiigi, eds., W. H. Freeman and Co.

Preferably, a Th1-type response is stimulated, i.e., elicited and/or enhanced. With reference to the invention, stimulating a Th1-type immune response can be determined in vitro or ex vivo by measuring cytokine production from cells treated with ISS as compared to those treated without ISS. Methods to determine the cytokine production of cells include those methods described herein and any known in the art. The type of cytokines produced in response to ISS treatment indicate a Th1-type or a Th2-type biased immune response by the cells. As used herein, the term "Th1-type biased" cytokine production refers to the measurable increased production of cytokines associated with a Th1-type immune response in the presence of a stimulator as compared to production of such cytokines in the absence of stimulation. Examples of such Th1-type biased cytokines include, but are not limited to, IL-2, IL-12, and IFN-γ. In contrast, "Th2-type biased cytokines" refers to those associated with a Th2-type immune response, and include, but are not limited to, IL-4, IL-5, and IL-13. Cells useful for the determination of ISS activity include cells of the immune system, primary cells isolated from a host and/or cell lines, preferably APCs and lymphocytes, even more preferably macrophages and T cells.

Stimulating a Th1-type immune response can also be measured in a host treated with an IMP/MC complex formulation can be determined by any method known in the art including, but not limited to: (1) a reduction in levels of IL-4 or IL-5 measured before and after antigen-challenge; or detection of lower (or even absent) levels of IL-4 or IL-5 in an IMP/MC complex treated host as compared to an antigen-primed, or primed and challenged, control treated without ISS; (2) an increase in levels of IL-12, IL-18 and/or IFN (α, β or γ) before and after antigen challenge; or detection of higher levels of IL-12, IL-18 and/or IFN (α, β or γ) in an IMP/MC complex treated host as compared to an antigen-primed or, primed and challenged, control treated without ISS; (3) "Th1-type biased" antibody production in an IMP/MC complex treated host as compared to a control treated without ISS; and/or (4) a reduction in levels of antigen-specific IgE as measured before and after antigen challenge; or detection of lower (or even absent) levels of antigen-specific IgE in an IMP/MC complex treated host as compared to an antigen-primed, or primed and challenged, control treated without ISS. A variety of these determinations can be made by measuring cytokines made by APCs and/or lymphocytes, preferably macrophages and/or T cells, in vitro or ex vivo using methods described herein or any known in the art. Some of these determinations can be made by measuring the class and/or subclass of antigen-specific antibodies using methods described herein or any known in the art.

The class and/or subclass of antigen-specific antibodies produced in response to IMP/MC complex treatment indicate a Th1-type or a Th2-type biased immune response by the cells. As used herein, the term "Th1-type biased" antibody production refers to the measurable increased production of antibodies associated with a Th1-type immune response (i.e., Th1-associated antibodies). One or more Th1 associated antibodies may be measured. Examples of such Th1-type biased antibodies include, but are not limited to, human IgG1 and/or IgG3 (see, e.g., Widhe et al. (1998) Scand. J. Immunol. 47:575–581 and de Martino et al. (1999) Ann. Allergy Asthma Immunol. 83:160–164) and murine IgG2a. In contrast, "Th2-type biased antibodies" refers to those associated with a Th2-type immune response, and include, but are not limited to, human IgG2, IgG4 and/or IgE (see, e.g., Widhe et al. (1998) and de Martino et al. (1999)) and murine IgG1 and/or IgE.

The Th1-type biased cytokine induction which occurs as a result of IMP/MC complex administration produces enhanced cellular immune responses, such as those performed by NK cells, cytotoxic killer cells, Th1 helper and memory cells. These responses are particularly beneficial for use in protective or therapeutic vaccination against viruses, fungi, protozoan parasites, bacteria, allergic diseases and asthma, as well as tumors.

In some embodiments, a Th2 response is suppressed. Suppression of a Th2 response may be determined by, for example, reduction in levels of Th2-associated cytokines, such as IL-4 and IL-5, as well as IgE reduction and reduction in histamine release in response to allergen.

KITS OF THE INVENTION

The invention provides kits for use in the methods of the invention. In certain embodiments, the kits of the invention comprise one or more containers comprising an IMP/MC complex and, optionally, a set of instructions, generally written instructions, relating to the use of the IMP/MC complex for the intended treatment (e.g., immunomodulation, ameliorating one or more symptoms of an infectious disease, increasing IFN-γ levels, increasing IFN-α levels, or ameliorating an IgE-related disorder). In further embodiments, the kits of the invention comprise containers of materials for producing IMP/MC, instructions for producing IMP/MC complex, and optionally instructions relating to the use of the IMP/MC complex for the intended treatment.

Kits which comprise preformed IMP/MC complex comprise IMP/MC complex packaged in any convenient, appropriate packaging. For example, if the IMP/MC complex is a dry formulation (e.g., freeze dried or a dry powder), a vial with a resilient stopper is normally used, so that the IMP/MC complex may be easily resuspended by injecting fluid through the resilient stopper. Ampoules with non-resilient, removable closures (e.g., sealed glass) or resilient stoppers are most conveniently used for liquid formulations of IMP/MC complex. Also contemplated are packages for use in combination with a specific device, such as an inhaler, nasal administration device (e.g., an atomizer) or an infusion device such as a minipump.

Kits which comprise materials for production of IMP/MC complex generally include separate containers of IMP and MC, although in certain embodiments materials for producing the MC are supplied rather than preformed MC. The IMP and MC are preferably supplied in a form which allows formation of IMP/MC complex upon mixing of the supplied IMP and MC. This configuration is preferred when the IMP/MC complex is linked by non-covalent bonding. This configuration is also preferred when the IMP and MC are to be crosslinked via a heterobifunctional crosslinker; either IMP or the MC is supplied in an "activated" form (e.g., linked to the heterobifunctional crosslinker such that a moiety reactive with the IMP is available).

Kits for IMP/MC complexes comprising a liquid phase MC preferably comprise one or more containers including materials for producing liquid phase MC. For example, an IMP/MC kit for oil-in-water emulsion MC may comprise one or more containers containing an oil phase and an aqueous phase. The contents of the container are emulsified to produce the MC, which may be then mixed with the IMP, preferably an IMP which has been modified to incorporate a hydrophobic moiety. Such materials include oil and water, for production of oil-in-water emulsions, or containers of lyophilized liposome components (e.g., a mixture of phospholipid, cholesterol and a surfactant) plus one or more containers of an aqueous phase (e.g., a pharmaceutically-acceptable aqueous buffer).

The instructions relating to the use of IMP/MC complex for the intended treatment generally include information as to dosage, dosing schedule, and route of administration for the intended treatment. The containers of ISS may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The following Examples are provided to illustrate, but not limit, the invention.

EXAMPLES

Example 1

Production of Non-covalent, Liquid Phase IMP/MC Complexes

IMP/MC complex comprising a modified IMP and a liquid phase MC were produced and tested for complex formation.

An IMP (phosphorothioate oligodeoxynucleotide 5'-TGACTGTGAACGTTCGAGATGA-3') (SEQ ID NO:1) was modified by addition of a cholesterol molecule to the 5' end of the IMP using phosphoramidite chemistry. An oil-in-water emulsion was produced by homogenization of a mixture of 4.5% (w/v) squalene, 0.5% (w/v) sorbitan trioleate, 0.5% (w/v) TWEEN® 80 and 10 mM sodium citrate, pH 6.5, using a microfluidizer. Examination of the emulsion found that the oil droplets in the emulsion had an average diameter of approximately 160 nm.

The emulsion was mixed with the cholesterol-modified IMP or an unmodified version of the same IMP, then centrifuged to separate the oil and water phases. RP-HPLC was performed on samples from each phase to determine nucleotide content. Approximately 75% of the cholesterol-modified IMP was found in the oil phase, while 100% of the unmodified IMP was found in the aqueous phase.

Example 2

Immunomodulation with IMP/MC Mixtures

Mixtures of an IMP (phosphorothioate oligodeoxynucleotide 5'-TGACTGTGAACGTTCGAGATGA-3') (SEQ ID NO:1) or a control oligonucleotide (phosphorothioate oligodeoxynucleotide 5'-TGACTGTGAAGGTTAGAGATGA-3') (SEQ ID NO:9) were mixed with sulphate-derivatized polycarbonate microparticles or nanoparticles (Polysciences, Inc.) and assayed for immunomodulatory activity on mouse splenocytes.

Fragments of BALB/c mouse spleen were digested with collagenase/dispase (0.1 U/mL/0.8U/mL) dissolved in phosphate buffered saline (PBS) for 45 minutes at 37° C., then mechanically dispersed by forcing the digested fragments through metal screens. The dispersed splenocytes were pelleted by centrifugation, then resuspended in fresh medium (RPMI 1640 with 10% fetal calf serum, plus 50 units/mL penicillin, 50 μg/mL streptomycin, 2 mM glutamine, and 0.05 mM β-mercaptoethanol).

$4 \times 10^5$ mouse splenocytes were dispensed into wells of 96 well plates and incubated for one hour at 37° C. 100 μL of 2× concentration test sample or control was added and the cells were incubated a further 24 hours. The cells were incubated with DNA doses of 5 μg/ml, 1 μg/ml and 0.1 μg/ml. Medium was harvested from each well and tested for cytokine concentrations by ELISA.

IFN-γ was assayed using a sandwich-format ELISA. Medium from the mouse splenocyte assay was incubated in microtiter plates coated with anti-IFN-γ monoclonal antibody (Nunc). Bound IFN-γ was detected using a biotinylated anti-IFN-γ antibody and streptavidin-horseradish peroxidase conjugated secondary antibody, developed with the chromogenic peroxidase substrate 3,3',5,5'-tetramethylbenzidine (TMB) in the presence of peroxidase, and quantitated by measuring absorbance at 450 nm using a Emax precision microplate reader (Molecular Devices). IL-6 and IL-12 were assayed with the same method using anti-IL-6 antibody and anti-IL-12 antibody, respectively.

200 nm beads mixed with IMP substantially increased IL-12, IL-6 and IFN-γ secretion by mouse splenocytes, and 50 nm beads mixed with IMP increased IL-12 and IL-6 production. Some nonspecific activity was associated with 200 nm beads mixed with the control oligonucleotide, although this was insufficient to account for the increase in stimulation as compared to IMP alone. Additionally, microcarriers of 1 μm and 4.5 μm also increased cytokine secretion. Tables 2–4 summarize assay results for IL-12, IL-6 and IFN-γ, respectively.

TABLE 2

| Test Material | DNA dose | | |
|---|---|---|---|
| | 5 μg/ml | 1 μg/ml | 0.1 μg/ml |
| IMP | IL-12 (pg/mL) | | |
| alone | 6046 | 4737 | 915 |
| IMP + 50 nm | 8582 | 4934 | 364 |
| IMP + 200 nm | 7377 | 8393 | 984 |
| IMP + 500 nm | 3680 | 4260 | 833 |
| IMP + 1 μm | 5082 | 4652 | 613 |
| IMP + 4.5 μm | 2253 | 2306 | 838 |
| control | | | |
| alone | 79 | 91 | 65 |
| control + 50 | 100 | 100 | 91 |
| control + 200 | 661 | 108 | 127 |
| control + 500 | 48 | 82 | 82 |
| control + 1000 | 72 | 101 | 147 |
| control + 4500 | 101 | 104 | 141 |

TABLE 3

| Test Material | DNA dose | |
|---|---|---|
| | 5 μg/ml | 0.1 μg/ml |
| IMP | IL-6 (pg/mL) | |
| alone | 5290 | 1872 |
| IMP + 50 nm | >18000 | 2127 |
| IMP + 200 nm | 6946 | 3574 |
| IMP + 500 nm | 345 | 2133 |
| IMP + 1 μm | 3812 | 2107 |
| IMP + 4.5 μm | 3277 | 1846 |
| control | | |
| alone | 24 | 24 |
| control + 50 | 24 | 24 |
| control + 200 | 1842 | 232 |
| control + 500 | 24 | 24 |
| control + 1000 | 24 | 24 |
| control + 4500 | 30 | 24 |

TABLE 4

| Test Material | DNA dose | |
|---|---|---|
| | 5 μg/ml | 0.1 μg/ml |
| IMP | IFN-γ (pg/mL) | |
| alone | 575 | 244 |
| IMP + 50 nm | 411 | 232 |
| IMP + 200 nm | 3548 | 3150 |
| IMP + 500 nm | 48 | 426 |
| IMP + 1 μm | 252 | 685 |
| IMP + 4.5 μm | 1072 | 2739 |

TABLE 4-continued

| Test Material | DNA dose | |
|---|---|---|
| | 5 µg/ml | 0.1 µg/ml |
| control | | |
| alone | 48 | 48 |
| control + 50 | 48 | 48 |
| control + 200 | 1907 | 101 |
| control + 500 | 48 | 48 |
| control + 1000 | 48 | 48 |
| control + 4500 | 50 | 48 |

Example 3

Immunomodulation of Mouse Cells by IMP/NC Complexes

IMPs covalently linked to polystyrene beads (200 nm design size) were tested for immunomodulatory activity on mouse splenocytes.

Phosphorothioate IMPs were synthesized with a disulfide linker on the 5'-end to facilitate linkage to the microcarrier. The C6 disulfide linker with a 4,4'-O-dimethoxytrityl group on one end and a cyanoethylphosphoramidite on the other end (Glen Research) was dissolved to a concentration of 0.1 M in acetonitrile. The linker was coupled to the 5'-end of the oligonucleotide and the resulting oligonucleotide was purified and isolated as described herein. The disulfide group on the oligonucleotide was reduced to a thiol before linkage to the microcarriers. The disulfideoligonucleotide was dissolved to a concentration of 25 mg/ml in 100 mM sodium phosphate/150 mM sodium chloride/1 mM ethylenediamine tetraacetic acid (EDTA)/pH 7.5 buffer. Then 5 equivalents of the hydrochloride salt of tris(carboxyethyl)phosphine (TCEP; Pierce) were added and the solution was heated to 40° C. for 2 hours. The thiol-containing IMPs were purified from the small molecule by-products by size exclusion chromatography and either used immediately or stored at −80° C. until use.

Amine-derivatized polystyrene beads were obtained from Molecular Probes, Inc., and Polysciences, Inc. Three types of beads were utilized: amine-derivatized beads (Polysciences, Inc., Catalog No. 15699), amine-derivatized beads linked to a fluorophore with excitation/emission maxima of 580 and 605 nm ("Red Beads", Molecular Probes, Inc., Catalog No. F8763), and amine-derivatized beads linked to a fluorophore with excitation/emission maxima of 505 and 515 nm ("Yellow Beads", Molecular Probes, Inc., Catalog No. F8764) were activated with sulfo-SMCC (sulfosuccinimidyl 4-(N-maleimidomethyl)cyclopentane-1-carboxylate, Pierce Chemical Co.) according to the manufacturer's instructions. The beads were then linked to thiol-modified IMP, a control phosphorothioate oligonucleotide (5'-TGACTGTGAAGGTTAGAGATGA-3' (control A) (SEQ ID NO: 9), 5'-TGACTGTGAACCTTAGAGATGA-3' (control B) (SEQ ID NO:10), or 5'-TCACTCTCTTCCT-TACTCTTCT-3' (control C) (SEQ ID NO:11), or treated to quench the free maleimide group for use as a NC only control. The IMP/MC complexes were isolated by centrifugation and washed three time with phosphate buffered saline to remove excess oligonucleotide.

Immunomodulatory effects of the IMP/NC complexes were assayed using mouse splenocytes as described above in Example 2. IMP/NC complexes demonstrated immunomodulation on the mouse splenocytes, as shown by increased secretion of IL-12, IL-6 and/or IFN-γ, while control oligonucleotides complexed with NC did not stimulate cytokine secretion. Data for IFN-γ secretion is summarized in Table 5.

TABLE 5

| | IFN-γ (pg/mL) | |
|---|---|---|
| Sample | 5 µg/ml dose | 1 µg/ml dose |
| White Beads | | |
| NC alone | 48 | 48 |
| IMP/NC | 903 | 77 |
| Red Beads | | |
| NC alone | 48 | 48 |
| IMP/NC | 319 | 63 |
| control A/NC | 48 | 48 |
| control B/NC | 48 | 48 |
| sulfo-SMCC activated NC | 2869 | 2147 |
| Yellow Beads | | |
| NC alone-lot 7781-2 | 1224 | 147 |
| 145-57A: IMP/NC-lot 145-57A | 3437 | 2335 |
| 145-57B: IMP/NC-lot 145-57B | 4556 | 5497 |
| 145-146: IMP/NC-lot 145-146C | 11444 | 7091 |
| 135-171A: IMP/NC-135-171A | 4493 | 2359 |
| 135-171B: control A/NC | 147 | 147 |
| 145-148: control B/NC | 147 | 147 |
| sulfo-SMCC activated NC, BME-inactivated | 3163 | 3723 |
| sulfo-SMCC activated NC, cysteine inactivated | 3392 | 3090 |
| sulfo-SMCC activated NC | 3583 | 4108 |
| IMP Controls | | |
| IMP | 558 | 577 |
| control C | 48 | 48 |

Example 4

Immunomodulation of Human Cells by IMP/NC Complexes

IMPs covalently linked to polystyrene beads (200 nm design size) were tested for immunomodulatory activity on human peripheral blood mononuclear cells (PBMCs).

Peripheral blood was collected from volunteers by venipuncture using heparinized syringes. Blood was layered onto FICOLL® (Amersham Pharmacia Biotech) cushion and centrifuged. PBMCs, located at the FICOLL® interface, were collected, then washed twice with cold phosphate buffered saline (PBS). The cells were resuspended and cultured in 24 or 48 well plates at $2 \times 10^6$ cells/mL in RPMI 1640 with 10% heat-inactivated human AB serum plus 50 units/mL penicillin, 50 µg/mL streptomycin, 300 µg/mL glutamine, 1 mM sodium pyruvate, and 1×MEM non-essential amino acids (NEAA).

The cells were cultured in the presence of test samples (IMP/NC formulations or controls) for 24 hours, then cell-free medium was collected from each well and assayed for IFN-γ concentration. IFN-γ was assayed using a CYTO-SCREEN™ ELISA kit from BioSource International, Inc., according to the manufacturer's instructions.

IMP/NC complexes stimulated IFN-γ secretion by human PBMCs. The results are summarized in Table 6.

TABLE 6

| Sample | IFN-γ (pg/mL) | | | |
|---|---|---|---|---|
| | Experiment 1 | | Experiment 2 | |
| | 5 μg/ml | 20 μg/ml | 5 μg/ml | 10 μg/ml |
| White Beads | | | | |
| NC alone | n/a | n/a | | |
| IMP/NC | 5 | 3 | | |
| Red Beads | | | | |
| NC alone | 2 | 8 | | |
| IMP/NC | 39 | 431 | | |
| control A/NC | 2 | 5 | | |
| control B/NC | 3 | 14 | | |
| sulfo-SMCC activated NC | 15 | n/a | | |
| Yellow Beads - Old | | | | |
| NC alone-lot 7781-2 | 12 | 56 | 8 | 19 |
| NC alone-lot 6991-1 | 7 | n/a | | |
| IMP/NC-lot 145-57A | 187 | n/a | | |
| IMP/NC-lot 145-57B | 777 | n/a | | |
| IMP/NC-lot 145-57C | 536 | 7752 | 6356 | 6413 |
| IMP/NC-lot 145-57D | 156 | 1861 | | |
| IMP/NC-lot 145-57E | 283 | 1385 | | |
| IMP/NC-lot 145-57F | 140 | n/a | | |
| IMP/NC-lot 145-146 | | | 934 | 6519 |
| IMP/NC-lot 135-171A | 123 | 2400 | | |
| control A/NC | 12 | 446 | | |
| control B/NC | | | 24 | 165 |
| sulfo-SMCC activated NC, BME-inactivated | | | 4 | 8 |
| sulfo-SMCC activated NC, cysteine inactivated | | | 7 | 15 |
| sulfo-SMCC activated NC | | | 7 | 14 |
| IMP Controls | | | | |
| IMP | <10 | <10 | | |

Example 5

Synthesis of 7-mer Oligonucleotides

The 7-mer oligonucleotide with the sequence 5'-TCGTCGA-3' with phosphorothioate linkages, was synthesized on a Perseptive Biosystems Expedite 8909 automated DNA synthesizer. The manufacturer's protocol for 15 μmol phosphorothioate DNA was used with the following changes: 1.6 ml of 3% dichloroacetic acid in dichloromethane over 2.5 minutes was used for the detritylation step; and 3.0 ml of 0.02 M 3-amino-1,2,4-dithiazole-5-thione (ADTT) in 9:1 acetonitrile:pyridine over 1.1 minutes followed by a 1.0 ml delivery over 1.0 minutes was used for the sulfurization step. The nucleoside phosphoramidite monomers were dissolved in anhydrous acetonitrile to a concentration of 0.1 M. The instrument was programmed to add the nucleotide monomers in the desired order, with the synthesis occurring in the 3' to 5' direction. The synthesis cycle consisted of a detritylation step, a coupling step (phosphoramidite monomer plus 1H-tetrazole), a capping step, a sulfurization step, and a final capping step.

At the completion of the assembly, the 'trityl-on' oligonucleotide was cleaved from the controlled-pore glass and the bases were deprotected with concentrated aqueous ammonia at 58° C. for 16 hours.

The 7-mer oligonucleotide was purified by RP-HPLC on a Polymer Labs PLRP-S column using an increasing gradient of acetonitrile in 0.1 M triethylammonium acetate. The purified oligonucleotide was concentrated to dryness, the 4,4'-dimethoxytrityl group was removed with 80% aqueous acetic acid, and then the compound was precipitated two times from 0.6 M aqueous sodium acetate/pH 5.0 with 3 volumes of isopropanol. The 7-mer oligonucleotide was dissolved in Milli Q water and the yield was determined from the absorbance at 260 nm. Finally, the oligonucleotide was lyophilized to a powder.

The 7-mer oligonucleotide was characterized by capillary gel electrophoresis, electrospray mass spectrometry, and RP-HPLC to confirm composition and purity. An endotoxin content assay (LAL assay, Bio Whittaker) was also conducted, showing endotoxin levels were <5 EU/mg oligonucleotide.

Other 7-mer phosphorothioate oligonucleotides were synthesized using the same methods including 5'-ACGTTCG-3', 5'-ATCTCGA-3', 5'-AGATGAT-3', 5'-TCGTTTT-3', 5'-TCGAAAA-3', 5'-TCGCCCC-3' and 5'-TCGGGGG-3'.

The 7-mer phosphorothioate oligonucleotide with the sequence 5'-TCGTCGA-3' was also synthesized with a disulfide linker on the 5'-end to facilitate linkage to the microcarrier. The C6 disulfide linker with a 4,4'-O-dimethoxytrityl group on one end and a cyanoethylphosphoramidite on the other end (Glen Research) was dissolved to a concentration of 0.1 M in acetonitrile. The linker was coupled to the 5'-end of the oligonucleotide and the resulting oligonucleotide was purified and isolated as described above.

The disulfide group on the oligonucleotide was reduced to a thiol before linkage to the microcarriers. The disulfide-oligonucleotide was dissolved to a concentration of 25 mg/ml in 100 mM sodium phosphate/50 mM sodium chloride/1mM ethylenediamine tetraacetic acid (EDTA)/pH 7.5 buffer. Then 5 equivalents of the hydrochloride salt of tris(carboxyethyl)phosphine (TCEP; Pierce) were added and the solution was heated to 40° C. for 2 hours. The thiol-containing oligonucleotide was purified from the small molecule by-products by size exclusion chromatography and either used immediately or stored at −80° C. until use.

Example 6

Immunomodulation with IMP/MC Mixtures with 7-mer Oligonucleotides Nonbiodegradable Microcarriers Mixtures of a heptameric oligonucleotide containing the sequence 5'-CG-3' or a control oligonucleotide (without the sequence 5'-CG-3') are mixed with sulphate-derivatized polycarbonate microparticles or nanoparticles (Polysciences, Inc.) and assayed for immunomodulatory activity on mouse splenocytes. Tested particles include those 50 nm, 200 nm, 500 nm, 1 µm and 4.5 µm in size.

Splenocytes are prepared as described in Example 2.4× $10^5$ mouse splenocytes are dispensed into wells of 96 well plates and incubated for one hour at 37° C. The cells are incubated with oligonucleotide doses of 5 µg/ml, 1 µg/ml and 0.1 µg/ml. 100 µL of 2× concentration test sample or control is added and the cells are incubated a further 24 hours. Medium is harvested from each well and tested for cytokine concentrations by ELISA. IFN-γ, IL-6 and IL-12 are assayed as described in Example 2. Immunomodulatory activity is assessed by detection of IL-12, IL-6 and/or IFN-γ in response to IMP/MC complexes.

Example 7

Immunomodulation of Mouse Cells by IMP/MC Complexes

Oligonucleotides covalently linked to nonbiodegradable polystyrene beads (200 nm design size) are tested for immunomodulatory activity on mouse splenocytes.

Amine-derivatized polystyrene beads are obtained from Molecular Probes, Inc., and Polysciences, Inc. Three types of beads are utilized: amine-derivatized beads (Polysciences, Inc., Catalog No. 15699), amine-derivatized beads linked to a fluorophore with excitation/emission maxima of 580 and 605 nm ("Red Beads", Molecular Probes, Inc., Catalog No. F8763), and amine-derivatized beads linked to a fluorophore with excitation/emission maxima of 505 and 515 nm ("Yellow Beads", Molecular Probes, Inc., Catalog No. F8764) are activated with sulfo-SMCC (sulfosuccinimidyl 4-(N-maleimidomethyl)cyclopentane-1-carboxylate, Pierce Chemical Co.) according to the manufacturer's instructions. The beads were then linked to thiol-modified oligonucleotides, or treated to quench the free maleimide group for use as a MC only control. The IMP/MC complexes are isolated by centrifugation and washed three time with phosphate buffered saline to remove excess oligonucleotide.

Immunomodulatory effects of the IMP/MC complexes were assayed using mouse splenocytes as described above in Example 2. The cells are incubated with oligonucleotide doses of 20 µg/ml, 5 µg/ml and 1 µg/ml. Immunomodulatory activity is assessed by detection of IL-12, IL-6 and/or IFN-γ in response to IMP/MC complexes.

Example 8

Immunomodulation of Human Cells by IMP/MC Complexes with Nonbiodegradable Microcarriers 7-mer oligonucleotides covalently linked to nonbiodegradable polystyrene beads (200 nm design size) are tested for immunomodulatory activity in the human PBMC assay. The complexes are made and the human PBMC assay is performed as described in Example 4. The cells are incubated with DNA doses of 20 µg/ml, 10 µg/ml and 2 µg/ml. Samples are assayed in PBMCs collected from two healthy donors in duplicate. IFN-γ and IFN-α are assayed using CYTOSCREEN™ ELISA kits from BioSource International, Inc., according to the manufacturer's instructions. Immunomodulatory activity is assessed by detection of IFN-γ and/or IFN-α in response to IMP/MC complexes.

Example 9

Effects of IMP/MC Complexes in Cell Proliferation Assay

Human PBMC are isolated from heparanized blood from two normal subjects as described in Example 4. Some PBMCs are held in reserve while the remainder are incubated with CD19+ MACS beads from Miltenyi. These cells are then passed through a magnet, separating out the CD19+ B cells through positive selection. The percentage of CD19+ cells in this population is determined through FACS analysis. B cells are then cultured at $1\times10^5/200$ µl/well in 96-well round-bottomed plates. PBMCs are also cultured, but at $2\times10^5/200$ µl/well. Cells are stimulated in triplicate with oligonucleotide either alone or with oligonucleotide linked to microcarriers. The culture period is 48 hours at 37° C. At the end of the culture period, the plates are pulsed with $^3$H-thymidine, 1 µCi/well, and incubated for an additional 8 hours. Then the plates are harvested using standard liquid scintillation techniques and data collected in counts per minutes (cpm). Cell proliferation is indicated by incorporation of the $^3$H-thymidine into the cell population.

Although the foregoing invention has been described in some detail by way of illustration and example for purposes of clarity and understanding, it will be apparent to those skilled in the art that certain changes and modifications may be practiced. Therefore, descriptions and examples should not be construed as limiting the scope of the invention, which is delineated by the appended claims.

What is claimed is:

1. A composition, comprising:
   an immunomodulatory polynucleotide/microcarrier (IMP/MC) complex, said complex comprising a polynucleotide comprising an immunostimulatory sequence (ISS) linked to a nonbiodegradable microcarrier (MC), wherein the ISS comprises a sequence selected from the group consisting of 5'-TCGAAAA-3', 5'-TCGCCCC-3', 5'-TCGGGGG-3', 5'-TCGTTTT-3' and 5'-TCGTCGX$_1$-3', wherein X$_1$ is a nucleotide, and wherein the polynucleotide is less than about 200 nucleotides in length; and
   a pharmaceutically acceptable excipient.

2. The composition of claim 1, wherein said polynucleotide is covalently linked to said microcarrier.

3. The composition of claim 1, wherein said polynucleotide is non-covalently linked to said microcarrier.

4. The composition of claim 1, wherein said microcarrier is a liquid phase microcarrier.

5. The composition of claim 1, wherein said microcarrier is a solid phase microcarrier.

6. The composition of claim 1, wherein said microcarrier is from 10 nm to 10 µm in size.

7. The composition of claim 6, wherein said microcarrier is from 25 nm to 5 µm in size.

8. The composition of claim 1, wherein said complex is antigen-free.

9. The composition of claim 1, wherein the ISS comprises the sequence 5'-TCGTCGA-3'.

10. The composition of claim 1, or 9, wherein said complex further comprises an antigen.

11. The composition of claim 10, wherein said antigen is an allergen.

12. The composition of claim 1, wherein said polynucleotide comprises a phosphate backbone modification.

13. The composition of claim 12, wherein said phosphate backbone modification is a phosphorothioate.

14. An immunomodulatory polynucleotide/microcarrier (IMP/MC) complex, comprising:
   a polynucleotide linked to a nonbiodegradable microcarrier (MC), wherein the polynucleotide comprises the sequence 5'-TCG-3' and wherein the polynucleotide is 7 nucleotides in length.

15. The IMP/MC complex of claim 14, wherein the polynucleotide consists of the sequence 5'-TCGX$_1$X$_2$X$_3$X$_4$-3' or the sequence 5'-X$_1$TCGX$_2$X$_3$X$_4$-3', wherein X$_1$, X$_2$, X$_3$, X$_4$ are nucleotides.

16. The IMP/MC complex of claim 15, wherein the polynucleotide consists of the sequence 5'-TCGTCGX$_1$-3', wherein X$_1$ is a nucleotide.

17. The IMP/MC complex of claim 15, wherein the polynucleotide consists of a sequence selected from the group consisting of 5'-TCGTCGA-3', 5'-TCGAAAA-3', 5'-TCGCCCC-3', 5'-TCGGGGG-3' and 5'-TCGTTTT-3'.

18. The IMP/MC complex of claim 14, wherein said polynucleotide comprises two copies of the sequence 5'-TCG-3'.

19. The IMP/MC complex of claim 14, wherein said complex further comprises an antigen.

20. The IMP/MC complex of claim 19, wherein said antigen is an allergen.

21. The IMP/MC complex of claim 14, wherein said polynucleotide comprises a phosphate backbone modification.

22. The IMP/MC complex of claim 21, wherein said phosphate backbone modification is a phosphorothioate.

23. A kit, comprising:
   an immunomodulatory polynucleotide/microcarrier (IMP/MC) complex, said complex comprising a polynucleotide linked to a nonbiodegradable microcarrier (MC), wherein said polynucleotide comprises a sequence selected from the group consisting of 5'-TCGAAAA-3', 5'-TCGCCCC-3', 5'-TCGGGGG-3', 5'-TCGTTTT-3' and 5'-TCGTCGX$_1$-3', wherein X$_1$ is a nucleotide, and wherein the polynucleotide is less than about 200 nucleotides in length; and
   instructions for use of IMP/MC complex in immunomodulation of an individual.

24. The kit of claim 23, wherein said polynucleotide is covalently linked to said microcarrier.

25. The kit of claim 23, wherein said polynucleotide is non-covalently linked to said microcarrier.

26. The kit of claim 23, wherein said microcarrier is a liquid phase microcarrier.

27. The kit of claim 23, wherein said microcarrier is a solid phase microcarrier.

28. The kit of claim 23, wherein said microcarrier is from 10 nm to 10 µm in size.

29. The kit of claim 28, wherein said microcarrier is from 25 nm to 5 µm in size.

30. The kit of claim 23, wherein said complex is antigen-free.

31. The kit of claim 23, wherein the polynucleotide comprises the sequence 5'-TCGTCGA-3'.

32. The kit of claims 23 or 31, further comprising an antigen.

33. The kit of claim 32, wherein said antigen is an allergen.

34. The kit of claim 23, wherein said polynucleotide comprises a phosphate backbone modification.

35. The kit of claim 34, wherein said phosphate backbone modification is a phosphorothioate.

36. A kit, comprising:
the IMP/MC complex of any of claims 14, 15, 16, and 17; and
instructions for use of IMP/MC complex in immunomodulation of an individual.

37. A composition comprising the IMP/MC complex of claim 14 and a pharmaceutically acceptable excipient.

38. A composition according to claim 37, wherein the composition is antigen-free.

39. A composition according to claim 37, wherein the composition further comprises an antigen.

40. A composition according to claim 39, wherein the antigen is an allergen.

41. The kit of claim 23 or claim 36, further comprising a pharmaceutically acceptable excipient.

* * * * *

SEQUENCE LISTING

<160> NUMBER OF SEQ ID NOS: 14

<210> SEQ ID NO 1
<211> LENGTH: 22
<212> TYPE: DNA
<213> ORGANISM: Artificial Sequence

```
<220> FEATURE:
<223> OTHER INFORMATION: Polynucleotide containing CG

<400> SEQUENCE: 1
tgactgtgaa cgttcgagat ga                                              22

<210> SEQ ID NO 2
<211> LENGTH: 22
<212> TYPE: DNA
<213> ORGANISM: Artificial Sequence
<220> FEATURE:
<223> OTHER INFORMATION: Polynucleotide containing CG

<400> SEQUENCE: 2
tgaccgtgaa cgttcgagat ga                                              22

<210> SEQ ID NO 3
<211> LENGTH: 23
<212> TYPE: DNA
<213> ORGANISM: Artificial Sequence
<220> FEATURE:
<223> OTHER INFORMATION: Polynucleotide containing CG

<400> SEQUENCE: 3
tcatctcgaa cgttccacag tca                                             23

<210> SEQ ID NO 4
<211> LENGTH: 22
<212> TYPE: DNA
<213> ORGANISM: Artificial Sequence
<220> FEATURE:
<223> OTHER INFORMATION: Polynucleotide containing CG

<400> SEQUENCE: 4
tgactgtgaa cgttccagat ga                                              22

<210> SEQ ID NO 5
<211> LENGTH: 26
<212> TYPE: DNA
<213> ORGANISM: Artificial Sequence
<220> FEATURE:
<223> OTHER INFORMATION: Polynucleotide containing CG

<400> SEQUENCE: 5
tccataacgt tcgcctaacg ttcgtc                                          26

<210> SEQ ID NO 6
<211> LENGTH: 22
<212> TYPE: DNA
<213> ORGANISM: Artificial Sequence
<220> FEATURE:
<223> OTHER INFORMATION: Polynucleotide containing (5-bromocytosine) G
<221> NAME/KEY: misc_feature
<222> LOCATION: 11
<223> OTHER INFORMATION: n= 5-bromocytosine

<400> SEQUENCE: 6
tgactgtgaa ngttccagat ga                                              22

<210> SEQ ID NO 7
<211> LENGTH: 22
<212> TYPE: DNA
<213> ORGANISM: Artificial Sequence
<220> FEATURE:
<223> OTHER INFORMATION: Polynucleotide containing (5-bromocytosine) G
<221> NAME/KEY: misc_feature
<222> LOCATION: 11
```

<223> OTHER INFORMATION: n= 5-bromocytosine

<400> SEQUENCE: 7
tgactgtgaa ngttcgagat ga                                                    22

<210> SEQ ID NO 8
<211> LENGTH: 22
<212> TYPE: DNA
<213> ORGANISM: Artificial Sequence
<220> FEATURE:
<223> OTHER INFORMATION: Polynucleotide containing (5-bromocytosine) G
<221> NAME/KEY: misc_feature
<222> LOCATION: 11, 15
<223> OTHER INFORMATION: n= 5-bromocytosine

<400> SEQUENCE: 8
tgactgtgaa ngttngagat ga                                                    22

<210> SEQ ID NO 9
<211> LENGTH: 22
<212> TYPE: DNA
<213> ORGANISM: Artificial Sequence
<220> FEATURE:
<223> OTHER INFORMATION: Polynucleotide not containing CG

<400> SEQUENCE: 9
tgactgtgaa ggttagagat ga                                                    22

<210> SEQ ID NO 10
<211> LENGTH: 22
<212> TYPE: DNA
<213> ORGANISM: Artificial Sequence
<220> FEATURE:
<223> OTHER INFORMATION: Polynucleotide not containing CG

<400> SEQUENCE: 10
tgactgtgaa ccttagagat ga                                                    22

<210> SEQ ID NO 11
<211> LENGTH: 22
<212> TYPE: DNA
<213> ORGANISM: Artificial Sequence
<220> FEATURE:
<223> OTHER INFORMATION: Polynucleotide not containing CG

<400> SEQUENCE: 11
tcactctctt ccttactctt ct                                                    22

<210> SEQ ID NO 12
<211> LENGTH: 11
<212> TYPE: DNA
<213> ORGANISM: Artificial Sequence
<220> FEATURE:
<223> OTHER INFORMATION: Polynucleotide containing CG

<400> SEQUENCE: 12
tcgagcgttc t                                                                11

<210> SEQ ID NO 13
<211> LENGTH: 20
<212> TYPE: DNA
<213> ORGANISM: Artificial Sequence
<220> FEATURE:
<223> OTHER INFORMATION: Polynucleotide containing CG

<400> SEQUENCE: 13

```
atcgactctc gagcgttctc                                              20

<210> SEQ ID NO 14
<211> LENGTH: 24
<212> TYPE: DNA
<213> ORGANISM: Artificial Sequence
<220> FEATURE:
<223> OTHER INFORMATION: Polynucleotide containing CG

<400> SEQUENCE: 14
tcgtcgtttt gtcgttttgt cgtt                                         24
```